United States Patent
Dejima

(10) Patent No.: US 10,595,715 B2
(45) Date of Patent: *Mar. 24, 2020

(54) ENDOSCOPIC SURGICAL DEVICE AND OUTER SLEEVE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,421

(22) Filed: Nov. 14, 2018

(65) Prior Publication Data

US 2019/0076004 A1    Mar. 14, 2019

Related U.S. Application Data

(63) Continuation of application No. 15/059,279, filed on Mar. 2, 2016, now Pat. No. 10,165,933, which is a continuation of application No. PCT/JP2014/072993, filed on Sep. 2, 2014.

(60) Provisional application No. 61/873,231, filed on Sep. 3, 2013.

(51) Int. Cl.
*A61B 1/018* (2006.01)
*A61B 1/00* (2006.01)
*A61B 1/01* (2006.01)
*A61B 17/34* (2006.01)
(Continued)

(52) U.S. Cl.
CPC .......... *A61B 1/018* (2013.01); *A61B 1/00135* (2013.01); *A61B 1/00154* (2013.01); *A61B 1/01* (2013.01); *A61B 1/015* (2013.01); *A61B 17/3421* (2013.01);
(Continued)

(58) Field of Classification Search
CPC .. A61B 1/00135; A61B 1/00142; A61B 1/015
See application file for complete search history.

(56) References Cited

U.S. PATENT DOCUMENTS

| | | |
|---|---|---|
| 3,432,085 A | 3/1969 | Lock |
| 4,040,413 A | 8/1977 | Ohshiro |
| 4,066,070 A | 1/1978 | Utsugi |

(Continued)

FOREIGN PATENT DOCUMENTS

| | | |
|---|---|---|
| JP | H10075958 | 3/1998 |
| JP | H11169342 | 6/1999 |

(Continued)

OTHER PUBLICATIONS

"Written Opinion of the International Searching Authority (Form PCT/ISA/237)" of PCT/JP2014/072989, dated Oct. 28, 2014, with English translation thereof, pp. 1-10.

(Continued)

*Primary Examiner* — Aaron B Fairchild
(74) *Attorney, Agent, or Firm* — JCIPRNET

(57) ABSTRACT

The overtube includes an interlocking member which is configured to be movable forward and backward inside an overtube body—and has an endoscope-coupled part and a treatment tool-coupled part. A side hole that is formed to pass through a side wall of the overtube body in communication with a passage in the overtube body for sending a fluid into a body cavity, and a side wall is configured to be openable and closable by the forward and backward movement of the interlocking member.

19 Claims, 30 Drawing Sheets

(51) Int. Cl.
*A61B 1/015* (2006.01)
*A61B 17/00* (2006.01)

(52) U.S. Cl.
CPC .............. *A61B 2017/00477* (2013.01); *A61B 2017/3409* (2013.01); *A61B 2017/3445* (2013.01)

(56) References Cited

U.S. PATENT DOCUMENTS

| | | | |
|---|---|---|---|
| 4,538,594 A * | 9/1985 | Boebel | A61B 1/31 600/102 |
| 5,569,205 A | 10/1996 | Hart et al. | |
| 5,634,911 A | 6/1997 | Hermann et al. | |
| 5,697,913 A | 12/1997 | Sierocuk et al. | |
| 6,004,302 A | 12/1999 | Brierley | |
| 6,142,931 A | 11/2000 | Kaji | |
| 6,315,714 B1 | 11/2001 | Akiba | |
| 2001/0049497 A1 | 12/2001 | Kalloo et al. | |
| 2003/0055437 A1 | 3/2003 | Yasunaga | |
| 2003/0135091 A1 | 7/2003 | Nakazawa et al. | |
| 2004/0147941 A1 * | 7/2004 | Takemoto | A61B 17/0467 606/144 |
| 2005/0065543 A1 | 3/2005 | Kahle et al. | |
| 2005/0119525 A1 | 6/2005 | Takemoto | |
| 2005/0119685 A1 | 6/2005 | Smith | |
| 2005/0222495 A1 | 10/2005 | Okada et al. | |
| 2007/0106319 A1 | 5/2007 | Au et al. | |
| 2008/0287963 A1 | 11/2008 | Rogers et al. | |
| 2009/0093752 A1 | 4/2009 | Richard et al. | |
| 2009/0259172 A1 * | 10/2009 | Yamaoka | A61B 1/00078 604/26 |
| 2009/0326463 A1 | 12/2009 | Ross | |
| 2010/0016659 A1 | 1/2010 | Weitzner | |
| 2010/0198006 A1 | 8/2010 | Greenburg et al. | |
| 2010/0256447 A1 | 10/2010 | Dubi et al. | |
| 2011/0124960 A1 | 5/2011 | St. Onge et al. | |
| 2011/0184231 A1 | 7/2011 | Page et al. | |
| 2011/0230713 A1 | 9/2011 | Kleemann et al. | |
| 2011/0282155 A1 | 11/2011 | Kase et al. | |
| 2015/0080650 A1 | 3/2015 | Dejima et al. | |
| 2016/0174825 A1 | 6/2016 | Dejima | |
| 2016/0174826 A1 | 6/2016 | Dejima | |

FOREIGN PATENT DOCUMENTS

| | | |
|---|---|---|
| JP | 2002-330928 | 11/2002 |
| JP | 2003-088532 | 3/2003 |
| JP | 2003061970 | 3/2003 |
| JP | 2003-325436 | 11/2003 |
| JP | 2004-041580 | 2/2004 |
| JP | 2004-141486 | 5/2004 |
| JP | 2004-180858 | 7/2004 |
| JP | 2005152416 | 6/2005 |
| JP | 2005-192707 | 7/2005 |
| JP | 2005-287963 | 10/2005 |
| JP | 2007521846 | 8/2007 |
| JP | 2009514651 | 4/2009 |
| JP | 2010005385 | 1/2010 |
| JP | 2011-528576 | 11/2011 |
| JP | 2012-501695 | 1/2012 |
| JP | 2012-505055 | 3/2012 |
| JP | 2012135650 | 7/2012 |
| WO | 2010042913 | 4/2010 |
| WO | 2011014711 | 2/2011 |
| WO | 2013176167 | 11/2013 |
| WO | 2015033909 | 3/2015 |
| WO | 2015033908 | 3/2017 |

OTHER PUBLICATIONS

"Office Action of Co-pending U.S. Appl No. 15/058,164," dated Sep. 29, 2016, p. 1-p. 15, in which the listed reference was cited.
"Office Action of Co-pending U.S. Appl. No. 15/058,164," dated Apr. 24, 2017, p. 1-p. 32.
"Office Action of Co-pending U.S. Appl. No. 15/058,164, " dated Dec. 19, 2017, p. 1-p. 17, in which the listed references were cited.
"Written Opinion of the International Searching Authority of PCT/JP2014/072992", this report contains the following items: Form PCT/ISA237 (cover sheet), PCT/ISA237 (Box No. I), PCT/ISA237 (Box No. III),PCT/ISA237 (Box No. V) and PCT/ISA237 (Box No. VI), dated Oct. 14, 2014, with English translation thereof, pp. 1-10.
"Office Action of Co-pending U.S. Appl. No. 15/059,277," dated Oct. 6, 2016, p. 1-p. 22, in which the listed references were cited.
"Office Action of Co-pending U.S. Appl. No. 15/059,277," dated May 18, 2017, p. 1-p. 33, in which the listed reference was cited.
"Office Action of Co-pending U.S. Appl. No. 15/059,277," dated Dec. 22, 2017, p. 1-p. 23.
"Office Action of Co-pending U.S. Appl. No. 15/058,111," dated Sep. 27, 2016, p. 1-p. 19, in which the listed references were cited.
"Written Opinion of the International Searching Authority of PCT/JP2014/072991", this report contains the following items: Form PCT/ISA237(cover sheet), PCT/ISA237(Box No. I), PCT/ISA237(Box No. V) and PCT/ISA237(Box No. VI), dated Oct. 14, 2014, which is English translation of "Written Opinion of the International Searching Authority", pp. 1-8.
"Office Action of Co-pending U.S. Appl. No. 15/058,111," dated May 5, 2017, p. 1-p. 32, in which the listed reference was cited.
"Office Action of Co-pending U.S. Appl. No. 15/058,111," dated Dec. 21, 2017, p. 1-p. 19, in which the listed reference was cited.
"Office Action of Japan Counterpart Application," with machine English translation thereof, dated Apr. 16, 2018, p. 1-p. 8, in which the listed references were cited.
"Office Action of Japan Related Application, application No. 2016195766", with English translation thereof, dated May 24, 2017, p. 1-p. 6.
"Written Opinion of the International Searching Authority of PCT/JP2014/072988", dated Oct. 28, 2014, with a partial English translation thereof, pp. 1-8.
"Office Action of Co-pending U.S. Appl. No. 15/058,176," dated Aug. 8, 2018, p. 1-p. 19.
"Office Action of Co-pending U.S. Appl. No. 15/058,176," dated Sep. 27, 2016, p. 1-p. 14.
"Office Action of Co-pending U.S. Appl. No. 15/058,176," dated May 3, 2017, p. 1-p. 28.
"Office Action of Co-pending U.S. Appl. No. 15/058,176," dated Dec. 20, 2017, p. 1-p. 15.
"Office Action of Co-pending U.S. Appl. No. 15/058,164," dated Aug. 8, 2018, p. 1-p. 11.
"Written Opinion of the International Searching Authority (Form PCT/ISA/237) of PCT/JP2014/072990," dated Oct. 28, 2014, with English translation thereof, pp. 1-8.
"Office Action of Japan Counterpart Application" dated Apr. 27, 2018, with English translation thereof, p. 1-p. 9.
"Written Opinion of the International Searching Authority (Form PCT/ISA/237) of PCT/JP2014/072993," dated Oct. 14, 2014, with English translation thereof, pp. 1-10.
"Office Action of Co-pending U.S. Appl. No. 15/059,279" dated Apr. 5, 2018, p. 1-p. 13.
"Office Action of Co-pending U.S. Appl. No. 16/120,455" dated Jun. 14, 2019, p. 1-p. 9.
"Office Action of Co-pending U.S. Appl. No. 16/290,971" dated Jun. 3, 2019, p. 1-p. 18.

* cited by examiner

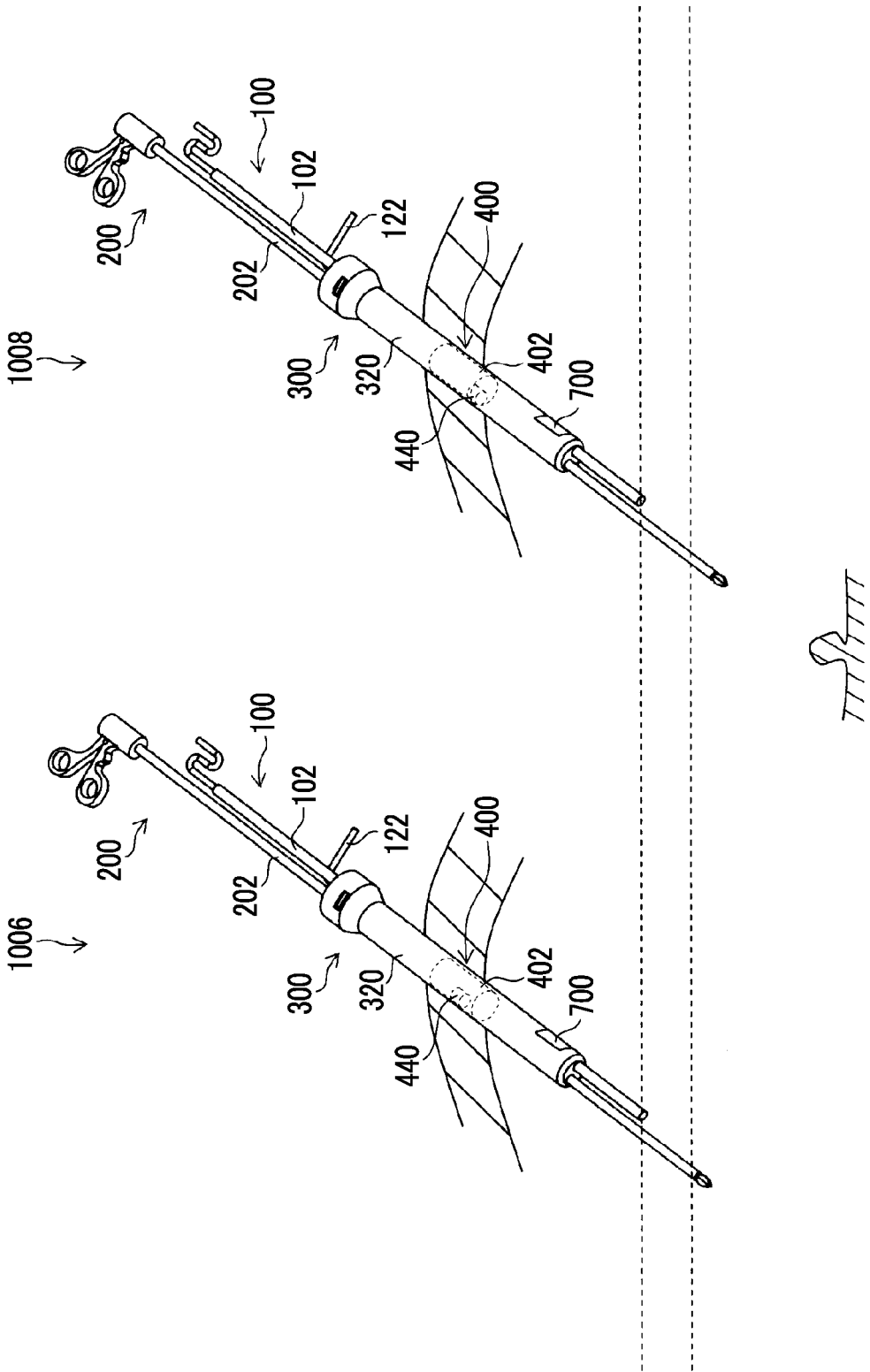

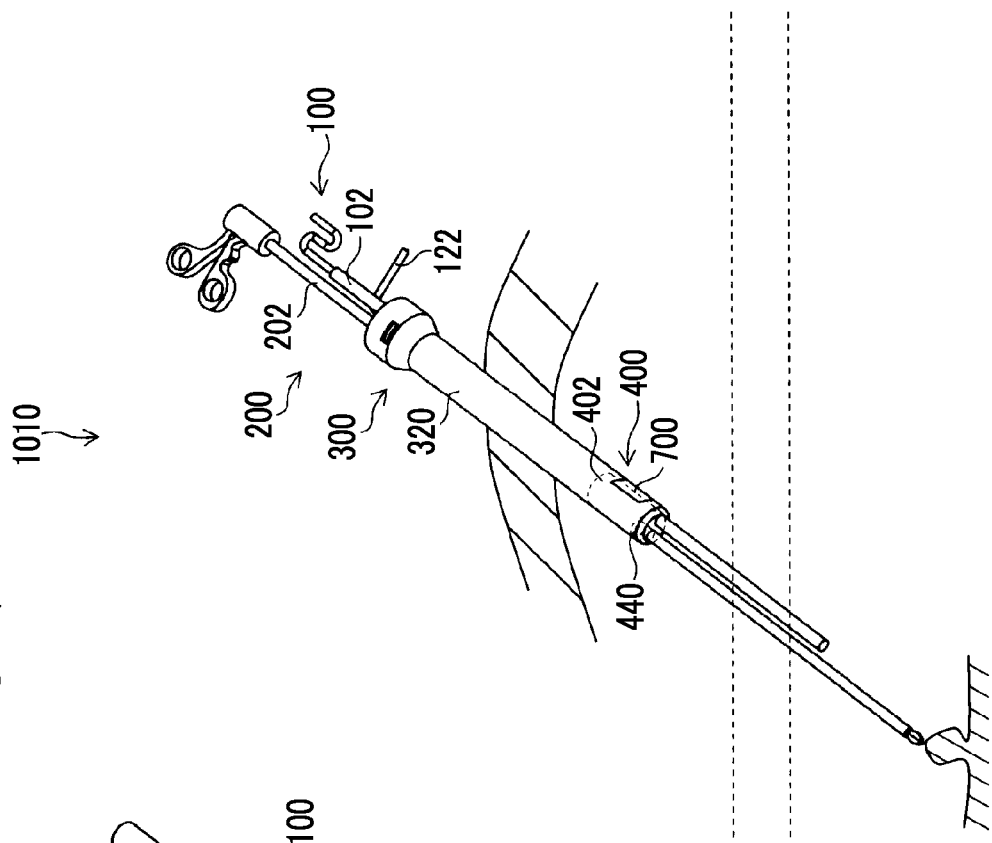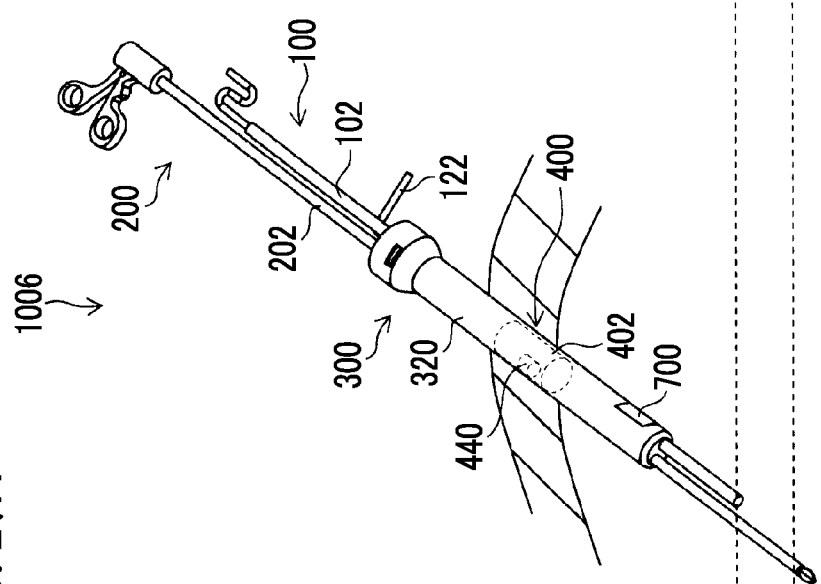

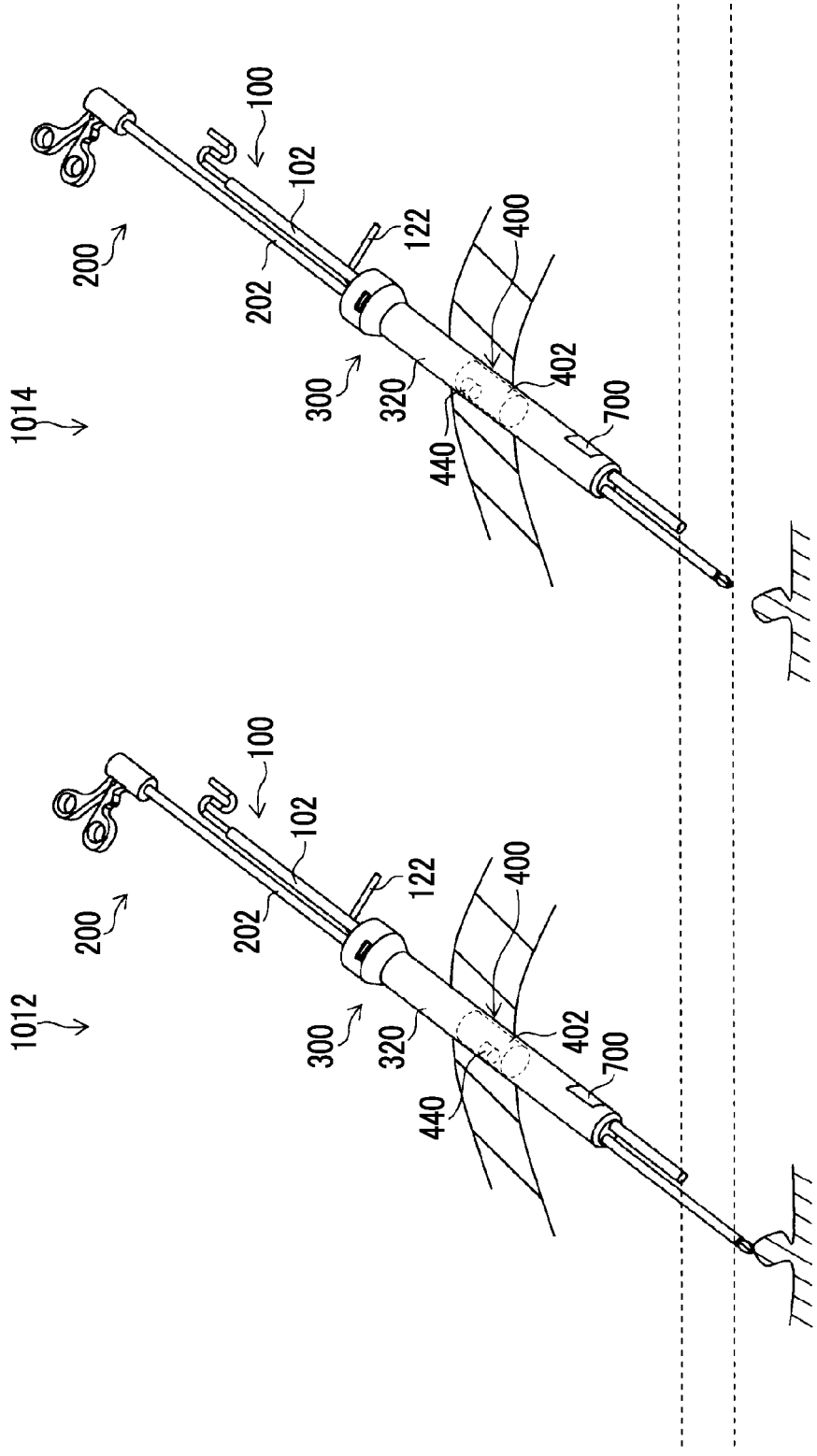
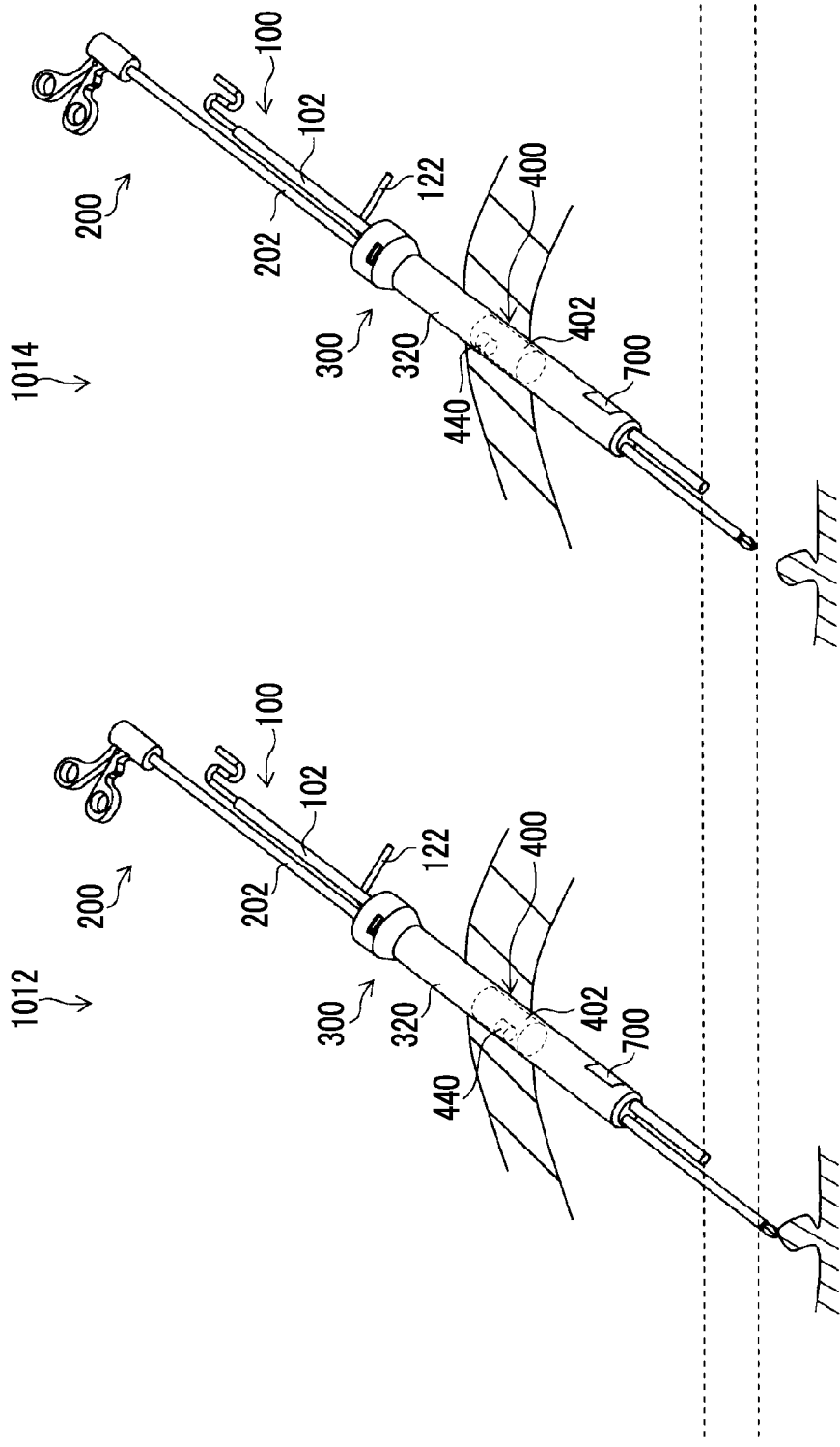

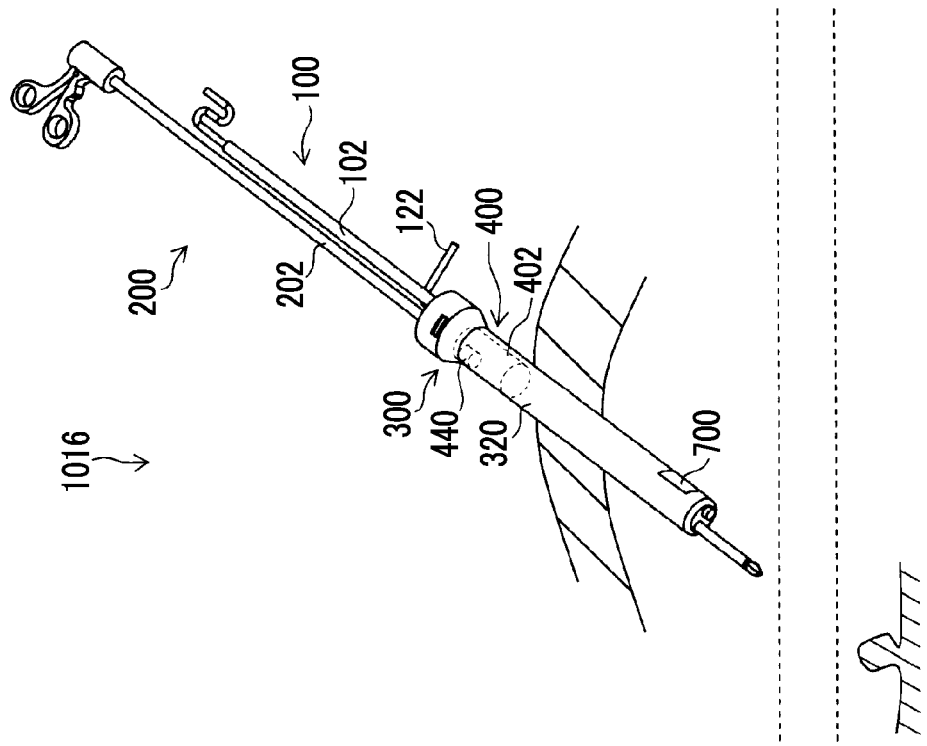
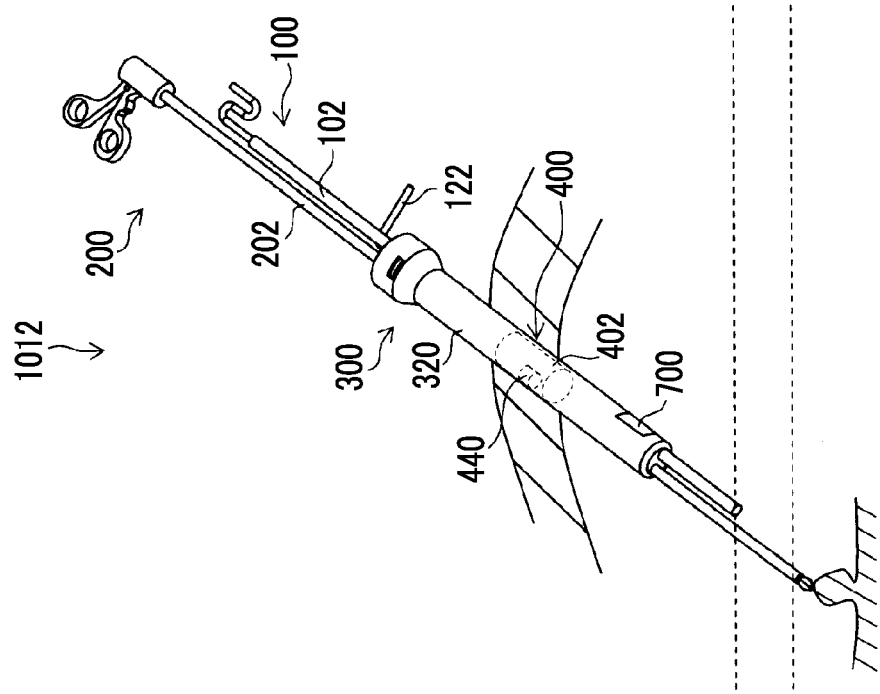

ENDOSCOPIC SURGICAL DEVICE AND OUTER SLEEVE

CROSS-REFERENCE TO RELATED APPLICATIONS

The present application is a continuation of and claims the priority benefit of a prior application Ser. No. 15/059,279, filed on Mar. 2, 2016, now allowed. The prior application Ser. No. 15/059,279 is a Continuation of PCT International Application No. PCT/JP2014/072993 filed on Sep. 2, 2014 claiming priority under 35 U.S.C. § 119(a) of U.S. Provisional Application No. 61/873,231 filed on Sep. 3, 2013. Each of the above applications is hereby expressly incorporated by reference, in their entirety, into the present application.

BACKGROUND OF THE INVENTION

1. Field of the Invention

The present invention relates to an endoscopic surgical device and an overtube (outer sleeve), and particularly, relates to an endoscopic surgical device and an overtube that can operate in a state where an endoscope and a treatment tool inserted into a body cavity are interlocked with each other.

2. Description of the Related Art

In the related art, the endoscopic surgery of inserting a treatment tool and an endoscope into a patient's body cavity and performing treatment work while observing, using the endoscope, the treatment state of an affected part using the treatment tool inserted into the body cavity has been known. In this surgery, in order for a surgeon to obtain a visual field where surgery is easy, the operation of changing the observation position of the endoscope is performed when necessary.

Generally, in the endoscopic surgery, a surgeon's hand is blocked due to the operation of the treatment tool, and the operation of changing the observation position of the endoscope is performed by an assistant called a scopist (endoscopic technician). For this reason, when the observation position of the endoscope is changed, the surgeon should serially give instructions to the assistant. Therefore, the work of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant should operate the endoscope so as not to interfere with a surgeon's procedure, and the operation is likely to become complicated.

In contrast, various techniques of interlocking the endoscope and the treatment tool have been suggested up to now (for example, refer to JP2004-141486A and JP2003-325436A).

An endoscopic surgery system that moves the treatment tool while following the fluctuation of the visual field of the endoscope is disclosed in JP2004-141486A. In this endoscopic surgery system, a treatment part of the treatment tool is kept from deviating from the visual field of the endoscope by detecting the movement distance (the rotational angle and the amount of insertion and extraction) of the endoscope in a state where the endoscope and the treatment tool are inserted into an integral sheath (guide member), and controlling the movement distance (the rotational angle and the amount of insertion and extraction) of the treatment tool with respect to the sheath on the basis of the detection result.

Additionally, an endoscopic surgery device that changes the visual field of the endoscope while following the movement of the treatment tool inserted into the body cavity during the endoscopic surgery is disclosed in JP2003-325436A. This endoscopic surgery device is provided by mechanically coupling the treatment tool to a distal end part of the endoscope to integrally move the treatment tool and the distal end part of the endoscope to move the observation optical axis of the endoscope in a direction in which the treatment tool moves.

Additionally, in overtubes that guide the endoscope or the treatment tool into the body cavity, an overtube in which an opening for sending pneumoperitoneum gas into the body cavity is provided in a side wall part is known (for example, refer to JP2012-135650A, JP2010-5385A, and JP1999-169342A (JP-H11-169342A)).

SUMMARY OF THE INVENTION

Under the above background, in the endoscopic surgery, it is desired that the visual field of the endoscope can be easily changed while the surgeon operates the treatment tool without asking for an assistant's help.

However, the endoscopic surgery system disclosed in JP2004-141486A does not mechanically interlock the endoscope with the treatment tool, and has a problem in which a mechanism for performing interlocking control of the endoscope and the treatment tool is easily enlarged and complicated. Additionally, this endoscopic surgery system moves the treatment tool while following the movement of the endoscope, and does not move the endoscope while following the movement of the treatment tool. For this reason, there are problems in that it is necessary to ask for an assistant's help in order to change the visual field of the endoscope, the operation for changing the observation position of the endoscope as intended by a surgeon easily becomes complicated, and the surgery time is easily prolonged.

Additionally, since the endoscopic surgery device disclosed in JP2003-325436A has a configuration in which the endoscope and the treatment tool are mechanically coupled and always move integrally, the visual field of the endoscope also changes minutely in an interlocking manner with minute movement of the treatment tool. For this reason, there is a problem in that an observation image obtained by the endoscope moves minutely and is hardly seen. Particularly when the endoscope and the treatment tool are inserted into the body cavity in a parallel state, there is a problem in which the size of an object to be observed changes in an interlocking manner with the minute movement of the treatment tool, and a sense of perspective cannot be easily held.

Additionally, as disclosed in JP2012-135650A, JP2010-5385A, and JP1999-169342A (JP-H11-169342A), in a configuration in which the opening is provided in the side wall part of the overtube, the flow rate of the pneumoperitoneum gas sent into the body cavity can be increased. However, when the overtube is inserted into the body cavity through the body wall, there is a problem in that tissue or blood easily enters the inside of the overtube through the opening from the body wall.

Regarding this problem, a configuration in which a valve capable of opening and closing the opening is disclosed in JP2012-135650A, and a configuration in which an overtube has a double sheath structure consisting of an outer sheath and an inner sheath and an opening (treatment window) is made openable and closable is disclosed in JP1999-169342A (JP-H11-169342A). However, in any of these configurations, a new mechanism for opening and closing the opening is required. As a result, since this becomes a factor that causes an increase in cost and an increase in the size, this is not preferable. In addition, the configuration for solving the above problem is neither disclosed nor suggested in JP2010-5385A.

In this way, in any of the related-art techniques, there are various problems in order to smoothly perform the endoscopic surgery, and it cannot be said that the techniques of interlocking the endoscope and the treatment tool inserted into the body cavity are sufficient.

The invention has been made in view of such a situation and an object thereof is to provide an endoscopic surgical device and an overtube with which a fluid can be supplied into a body cavity while preventing entry of tissue or blood in a body wall into the overtube, without causing an increase in cost and an increase in size, and a surgeon can easily obtain a desired image with simple operation without increasing a burden on the surgeon.

In order to achieve the above object, an endoscopic surgical device related to a first aspect of the invention is an endoscopic surgical device including an endoscope that observes the inside of a body cavity; a treatment tool that inspects or treats an affected part within the body cavity; and an overtube that guides the endoscope and the treatment tool into the body cavity. The overtube includes an overtube body that passes through a body wall and is inserted into the body cavity, an endoscope insertion passage that is provided inside the overtube body and allows the endoscope to be inserted therethrough so as to be movable forward and backward, a treatment tool insertion passage that is provided inside the overtube body and allows the treatment tool to be inserted therethrough so as to be movable forward and backward, an interlocking member which is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, and a side surface opening that is formed to pass through a side wall of the overtube body in communication with a passage in the overtube body and is configured to send a fluid into the body cavity. The side surface opening is configured to be openable and closable by the forward and backward movement of the interlocking member.

In the first aspect of the invention, it is preferable that the endoscopic surgical device further includes an inner needle that includes a first elongated shaft part inserted through the endoscope insertion passage and a second elongated shaft part inserted through the treatment tool insertion passage, and that is assembled into the overtube body in a state where respective distal end parts of the first shaft part and the second shaft part are made to protrude from the overtube body when being inserted into the body cavity, the interlocking member is positioned at a position that faces the side surface opening in a state where the inner needle has been assembled into the overtube body, and the side surface opening is closed by one wall surface of the interlocking member.

Additionally, in the first aspect of the invention, it is preferable that the first shaft part or the second shaft part is provided with an engagement part that engages with the interlocking member, and the interlocking member is positioned at a position that faces the side surface opening by the engagement part of the first shaft part or the second shaft part being engaged therewith, in a state where the inner needle has been assembled into the overtube body.

Additionally, in the first aspect of the invention, it is preferable that the inner needle includes a head part that links a base end of the first shaft part and a base end of the second shaft part, and a fixing mechanism that is provided at the head part and detachably fixes the head part to the overtube, and the interlocking member is arranged at a position that faces the side surface opening when the head part has been fixed to the overtube by the fixing mechanism.

Additionally, in the first aspect of the invention, it is preferable that the first shaft part or the second shaft part includes a smaller-diameter part that is arranged on a distal end side, and a larger-diameter part that is connected to a base end side of the smaller-diameter part, the engagement part is constituted by a stepped part formed at a boundary position between the smaller-diameter part and the larger-diameter part, and the interlocking member includes a hole that is larger than the external diameter of the smaller-diameter part and is smaller than the external diameter of the larger-diameter part, and an abutment part that is a peripheral part of the hole and against which the stepped part abuts.

Additionally, in the first aspect of the invention, it is preferable that the engagement part includes a frictional engagement part that frictionally engages with the interlocking member.

Additionally, in the first aspect of the invention, it is preferable that the side surface opening is provided on a distal end side of the overtube body, and is closed by one wall surface of the interlocking member when the interlocking member has moved to a foremost position of a movable range thereof.

Additionally, in the first aspect of the invention, it is preferable that the interlocking member includes a slider member that is coupled to the endoscope and moves forward and backward integrally with the endoscope, and a sleeve member that is coupled to the treatment tool and moves forward and backward integrally with the treatment tool, and a range where the sleeve member is movable forward and backward with respect to the slider member is limited.

Additionally, in the first aspect of the invention, it is preferable that the following formula is satisfied when a fixing force for fixing the endoscope-coupled part to the endoscope is defined as F1 and a fixing force for the treatment tool-coupled part to the treatment tool is defined as F2.

$$F1 > F2$$

Additionally, in the first aspect of the invention, it is preferable that the endoscopic surgical device further includes a first valve member that is provided in the endoscope insertion passage and secures airtightness within the body cavity; and a second valve member that is provided in the treatment tool insertion passage and secures airtightness within the body cavity, and the following formulas are satisfied when a fixing force for fixing the endoscope-coupled part to the endoscope is defined as F1, a fixing force for fixing the treatment tool-coupled part to the treatment tool is defined as F2, and a frictional force that the endoscope receives from the first valve member when the endoscope moves forward and backward is defined as F3.

$$F1 > F3$$

$$F2 > F3$$

Additionally, an endoscopic surgical device related to a second aspect of the invention is an endoscopic surgical device including an inner needle and an overtube that guides the inner needle into the body cavity, wherein the inner needle that includes a first elongated shaft part and a second elongated shaft part, and that is assembled into the overtube body in a state where respective distal end parts of the first shaft part and the second shaft part are made to protrude from the overtube body when being inserted into the body cavity. The overtube includes an overtube body that passes through a body wall and is inserted into the body cavity, a first insertion passage that is provided inside the overtube body and allows the first shaft part to be inserted therethrough so as to be movable forward and backward, a second insertion passage that is provided inside the overtube body and allows the second shaft part to be inserted therethrough so as to be movable forward and backward, an interlocking member which is configured to be movable forward and backward inside the overtube body, couplable to the first shaft part inserted through the first insertion passage and a the second shaft part inserted through the second insertion passage, a side surface opening that is formed to pass through a side wall of the overtube body, in communication with a passage in the overtube body and is configured to send a fluid into the body cavity and a shutter member that is arranged inside the overtube body, is movable in engagement with the inner needle, and is movable between an open position where the side surface opening is open and a closed position where the side surface opening is closed.

Additionally, in the second aspect of the invention, it is preferable that the inner needle includes a head part that links a base end of the first shaft part and a base end of the second shaft part, and a fixing mechanism that is provided at the head part and detachably fixes the head part to the overtube, and the shutter member is located at the closed position when the head part has been fixed to the overtube by the fixing mechanism.

Additionally, an overtube related to a third aspect of the invention is an overtube including an overtube body that passes through a body wall and is inserted into a body cavity; an endoscope insertion passage that is provided inside the overtube body and allows an endoscope for observing the inside of the body cavity to be inserted therethrough so as to be movable forward and backward; a treatment tool insertion passage that is provided inside the overtube body and allows a treatment tool for inspecting or treating an affected part within the body cavity to be inserted therethrough so as to be movable forward and backward; an interlocking member which is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage; and a side surface opening that is formed to pass through a side wall of the overtube body in communication with a passage in the overtube body, and is configured to send a fluid into the body cavity. The side surface opening is configured to be openable and closable by the forward and backward movement of the interlocking member.

Additionally, in the third aspect of the invention, it is preferable that the endoscopic surgical device further includes an inner needle that includes a first elongated shaft part inserted through the endoscope insertion passage and a second elongated shaft part inserted through the treatment tool insertion passage, and that is assembled into the overtube body in a state where respective distal end parts of the first shaft part and the second shaft part are made to protrude from the overtube body when being inserted into the body cavity, the interlocking member is positioned at a position that faces the side surface opening in a state where the inner needle has been assembled into the overtube body, and the side surface opening is closed by one wall surface of the interlocking member.

Additionally, in the third aspect of the invention, it is preferable that the first shaft part or the second shaft part is provided with an engagement part that engages with the interlocking member, and the interlocking member is positioned at a position that faces the side surface opening by the engagement part of the first shaft part or the second shaft part being engaged therewith, in a state where the inner needle has been assembled into the overtube body.

Additionally, in the third aspect of the invention, it is preferable that the inner needle includes a head part that links a base end of the first shaft part and a base end of the second shaft part, and a fixing mechanism that is provided at the head part and detachably fixes the head part to the overtube, and the interlocking member is arranged at a position that faces the side surface opening when the head part has been fixed to the overtube by the fixing mechanism.

Additionally, in the third aspect of the invention, it is preferable that the first shaft part or the second shaft part includes a smaller-diameter part that is arranged on a distal end side, and a larger-diameter part that is connected to a base end side of the smaller-diameter part, the engagement part is constituted by a stepped part formed at a boundary position between the smaller-diameter part and the larger-diameter part, and the interlocking member includes a hole that is larger than the external diameter of the smaller-diameter part and is smaller than the external diameter of the larger-diameter part, and an abutment part that is a peripheral part of the hole and against which the stepped part abuts.

Additionally, in the third aspect of the invention, it is preferable that the engagement part includes a frictional engagement part that frictionally engages with the interlocking member.

Additionally, in the third aspect of the invention, it is preferable that the side surface opening is provided on a distal end side of the overtube body, and is closed by one wall surface of the interlocking member when the interlocking member has moved to a foremost position of a movable range thereof.

Additionally, an overtube related to a fourth aspect of the invention is an overtube including an overtube body that passes through a body wall and is inserted into the body cavity; a first insertion passage that is provided inside the overtube body and allows a first shaft part for observing the inside of the body cavity to be inserted therethrough so as to be movable forward and backward; a second insertion passage that is provided inside the overtube body and allows a second shaft part for inspecting or treating an affected part within the body cavity to be inserted therethrough so as to be movable forward and backward; an interlocking member which is configured to be movable forward and backward inside the overtube body, couplable to the first shaft part inserted through the first insertion passage and the second shaft part inserted through the second insertion passage, a side surface opening that is formed to pass through a side wall of the overtube body, in communication with a passage in the overtube body, and is configured to send a fluid into the body cavity; an inner needle that includes a first elongated shaft part and a second elongated shaft part, and that is assembled into the overtube body in a state where respective distal end parts of the first shaft part and the second shaft part are made to protrude from the overtube body when being inserted into the body cavity; and a shutter member that is arranged inside the overtube body, is movable in engagement with the inner needle, and is movable between an open position where the side surface opening is open and a closed position where the side surface opening is closed.

Additionally, in the fourth aspect of the invention, it is preferable that the inner needle includes a head part that links a base end of the first shaft part and a base end of the second shaft part, and a fixing mechanism that is provided at the head part and detachably fixes the head part to the overtube, and the shutter member is located at the closed position when the head part has been fixed to the overtube by the fixing mechanism.

According to the invention, the endoscope moves forward and backward with play with respect to the forward and backward movement of the treatment tool. Thus, when the treatment tool has been minutely displaced in the axial direction (when a forward and backward movement of a small amplitude has been performed), the size of an object to be observed can be prevented from fluctuating, a sense of perspective can be suitably maintained, and a stable observation image can be provided. Additionally, when the treatment tool has been largely displaced in the axial direction (when a forward and backward movement of a large amplitude has been performed), the range of an observation image obtained by the endoscope is changed in an interlocking manner. Thus, the size of an object to be observed changes according to the operation of the treatment tool, and it is possible to simply obtain an image desired by a surgeon, and operability improves. Additionally, the side surface opening provided in the side wall of the overtube (overtube body) is configured to be openable and closable by the forward and backward movement of the interlocking member that interlocks the treatment tool and the endoscope. Thus, the fluid can be efficiently sent into the body cavity with a compact structure without causing an increase in cost and an increase in size, and it is possible to effectively prevent tissue or blood in the body wall from entering the overtube.

BRIEF DESCRIPTION OF THE DRAWINGS

FIGS. 28A and 28B are views illustrating a situation in which the treatment tool insertion part is pushed into the affected part side within the body cavity from the hand side.

FIGS. 29A and 29B are views illustrating a situation in which the treatment tool insertion part is pushed into the affected part side within the body cavity from the hand side.

FIGS. 30A and 30B are views illustrating a situation in which the treatment tool insertion part is pulled to the hand side from the affected part side within the body cavity.

FIGS. 31A and 31B are views illustrating a situation in which the treatment tool insertion part is pulled to the hand side from the affected part side within the body cavity.

DESCRIPTION OF THE PREFERRED EMBODIMENTS

A preferred embodiment of the invention will be described below in detail according to the accompanying drawings. In addition, any drawing may illustrate main parts in an exaggerated manner for description, and may have dimensions different from actual dimensions. Additionally, in the following, characteristic parts of the invention will be described in detail after the basic configuration of an endoscope surgical device (endoscopic surgical device) is first described.

Configuration of Endoscopic Surgical Device

Figure 1:
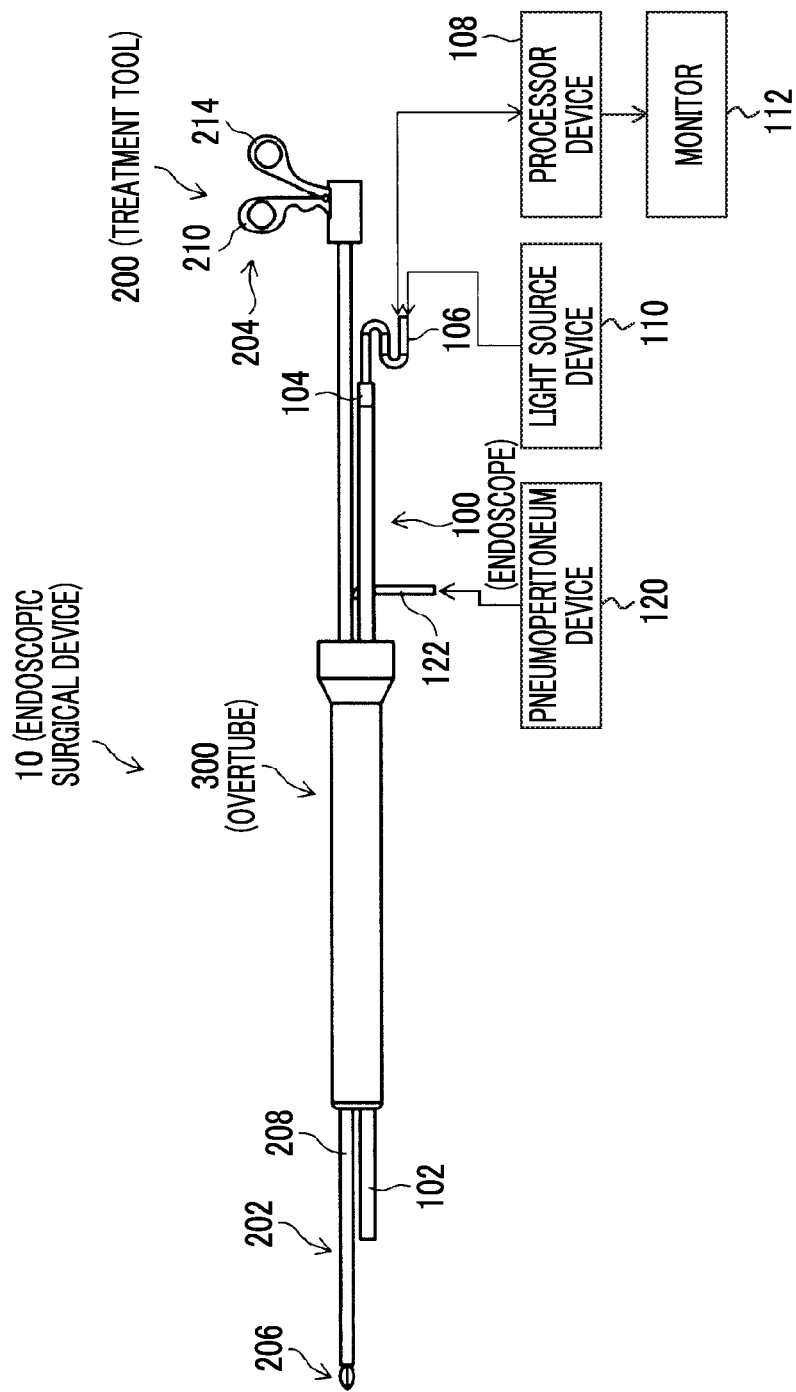
FIG. 1 is a schematic configuration diagram illustrating the basic configuration of an endoscopic surgical device.

FIG. 1 is a schematic configuration diagram illustrating the basic configuration of the endoscopic surgical device. As illustrated in FIG. 1, an endoscopic surgical device 10 includes an endoscope 100 that observes the inside of a patient's body cavity, a treatment tool 200 for inspecting or treating an affected part within the patient's body cavity, and an overtube 300 (guide member) that guides the endoscope 100 and the treatment tool 200 into the body cavity.

Configuration of Endoscope

The endoscope 100 includes an elongated insertion part (hereinafter referred to as "endoscope insertion part") 102 that is, for example, a hard endoscope, such as a laparoscope, and that is inserted into a body cavity, and an operating part 104 that is provided continuously with a base end side of the endoscope insertion part 102. A universal cable 106 is connected to the operating part 104, and each of a processor device 108 and a light source device 110 is detachably connected to a distal end part of the universal cable 106 via a connector (not illustrated). Additionally, the processor device 108 is connected to a monitor 112 via a cable.

Figure 2:
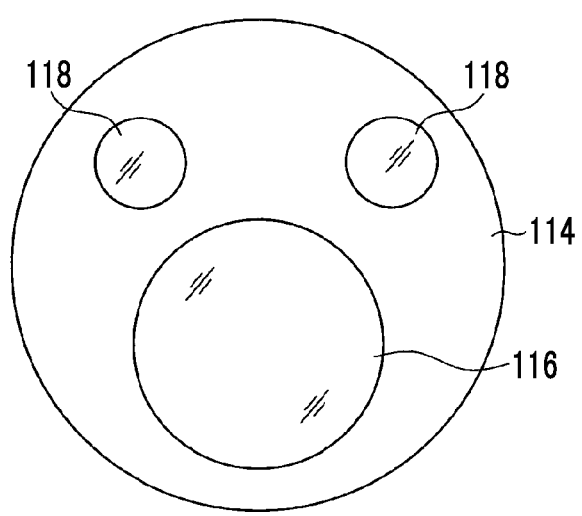
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

An objective lens of an observation optical system, and image pick-up elements, such as a charge-coupled device (CCD) and a complementary metal-oxide semiconductor (CMOS), which are arranged at an image pick-up position of the objective lens, are disposed behind the observation window 116. A signal cable (not illustrated) is connected to a substrate that supports the image pick-up element. The signal cable is inserted through the endoscope insertion part 102, the operating part 104, and the universal cable 106, and the like of FIG. 1, is provided to extend up to the connector (not illustrated), and is connected to the processor device 108. An observation image picked up by the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of a light guide (not illustrated) is disposed behind the illumination windows 118 and 118 of FIG. 2. The light guide is inserted through the endoscope insertion part 102, the operating part 104, and the universal cable 106 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of the illumination windows 118 is not limited, and the number thereof may be one or three or more.

Configuration of Treatment Tool

As illustrated in FIG. 1, the treatment tool 200 consists of, for example, forceps, and includes an elongated insertion part (hereinafter referred to as a "treatment tool insertion part") 202 that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is rotatably coupled to the fixed handle 210 via a turning pin. A base end part of the operating shaft is coupled to the movable handle 214.

The treatment part 206 is provided with a pair of gripping members capable of being openable and closable. The gripping members are coupled to a distal end part of the operating shaft via a driving mechanism (not illustrated). With the rotational operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

Configuration of Overtube

Figure 3:
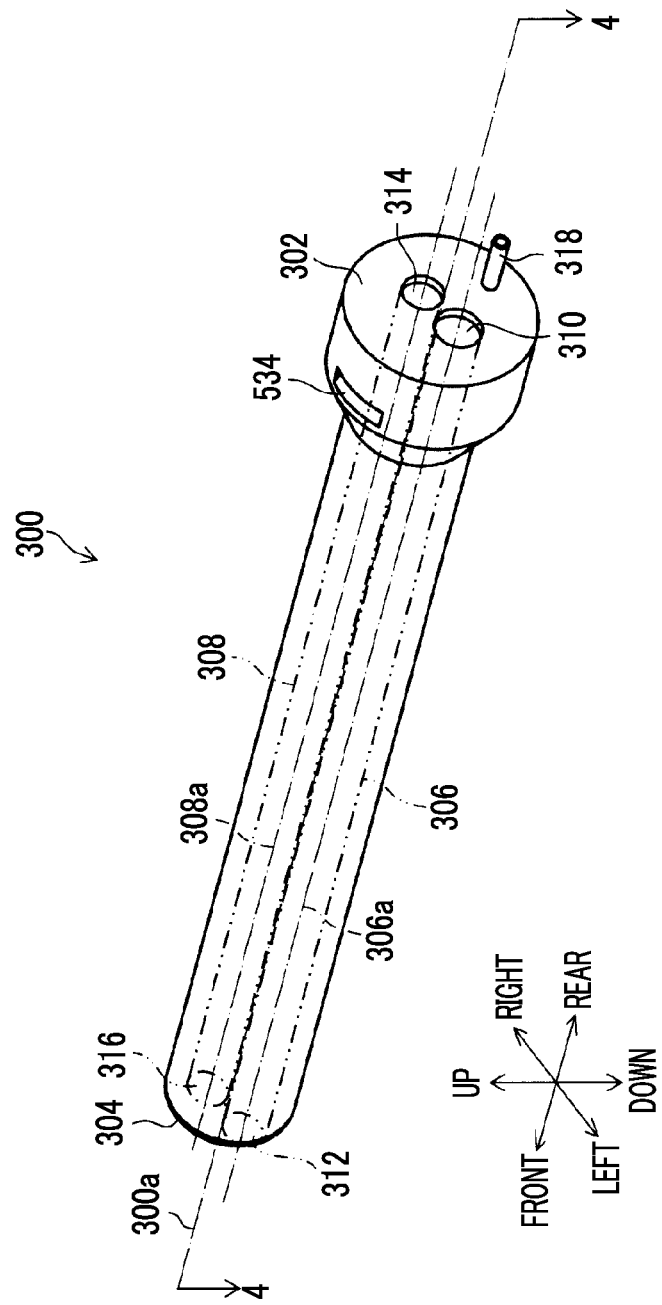
FIG. 3 is an external appearance perspective view illustrating an overtube from the rear upper left.

FIG. 3 is an external appearance perspective view illustrating the overtube 300 from the rear upper left.

As illustrated in this drawing, the overtube 300 has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward.

The endoscope insertion passage 306 has a diameter such that at least the endoscope insertion part 102 is capable of being inserted therethrough, using an endoscope insertion axis 306a, which is parallel to a reference axis 300a (longitudinal axis) indicating a central axis of the entire overtube 300, as a central axis, and indicates a space portion within the overtube 300 that penetrates from a base end surface 302 of the overtube 300 to a distal end surface 304 thereof. The endoscope insertion axis 306a is equivalent to the position of the axis (central axis) of the endoscope insertion part 102 that is inserted through the endoscope insertion passage 306.

The base end surface 302 is provided with an endoscope insertion opening 310 for allowing the endoscope insertion part 102 to be inserted into the endoscope insertion passage 306 therethrough, and the distal end surface 304 is provided with an endoscope delivery opening 312 for allowing the endoscope insertion part 102 inserted into the endoscope insertion passage 306 to be delivered to the outside therethrough.

The treatment tool insertion passage 308 has a diameter such that at least the treatment tool insertion part 202 is capable of being inserted therethrough, using a treatment tool insertion axis 308a parallel to the reference axis 300a as a central axis, and indicates a space portion within the overtube 300 that penetrates from the base end surface 302 of the overtube 300 to the distal end surface 304. The treatment tool insertion axis 308a is equivalent to the position of the axis (central axis) of the treatment tool insertion part 202 that is inserted through the treatment tool insertion passage 308.

The base end surface 302 is provided with a treatment tool insertion opening 314 for allowing the treatment tool insertion part 202 to be inserted into the treatment tool insertion passage 308 therethrough, and the distal end surface 304 is provided with a treatment tool delivery opening 316 for allowing the treatment tool insertion part 202 inserted into the treatment tool insertion passage 308 to be delivered to the outside therethrough.

Additionally, the overtube 300 has an air supply connector 318 (fluid-supplying connector) on the base end surface 302. The air supply connector 318 is provided at the end part of an air supply pipe line that communicates with the endoscope insertion passage 306 and the treatment tool insertion passage 308 inside the overtube 300.

One end part of an air supply tube 122 (tube member) illustrated in FIG. 1 is connected to the air supply connector 318, and the other end part of the air supply tube 122 is connected to a pneumoperitoneum device 120. Therefore, if pneumoperitoneum gas (gas for pneumoperitoneum), such as carbon dioxide gas, is supplied from the pneumoperitoneum device 120 to the air supply tube 122, the pneumoperitoneum gas is sent from the air supply connector 318 to the inside of the overtube 300, and is delivered from the endoscope delivery opening 312 and the treatment tool delivery opening 316 of the distal end surface 304 through the inside of the overtube 300 to the outside of the overtube 300.

In addition, regarding the position and orientation of a space where the overtube 300 has been arranged, terms called front, rear, left, right, up, and down are used with the orientation from the base end surface 302 in a direction along the reference axis 300a to the distal end surface 304 defined as the front and with the orientation from the reference axis 300a to the endoscope insertion axis 306a defined as the left.

(Internal Structure of Overtube)

Figure 4:
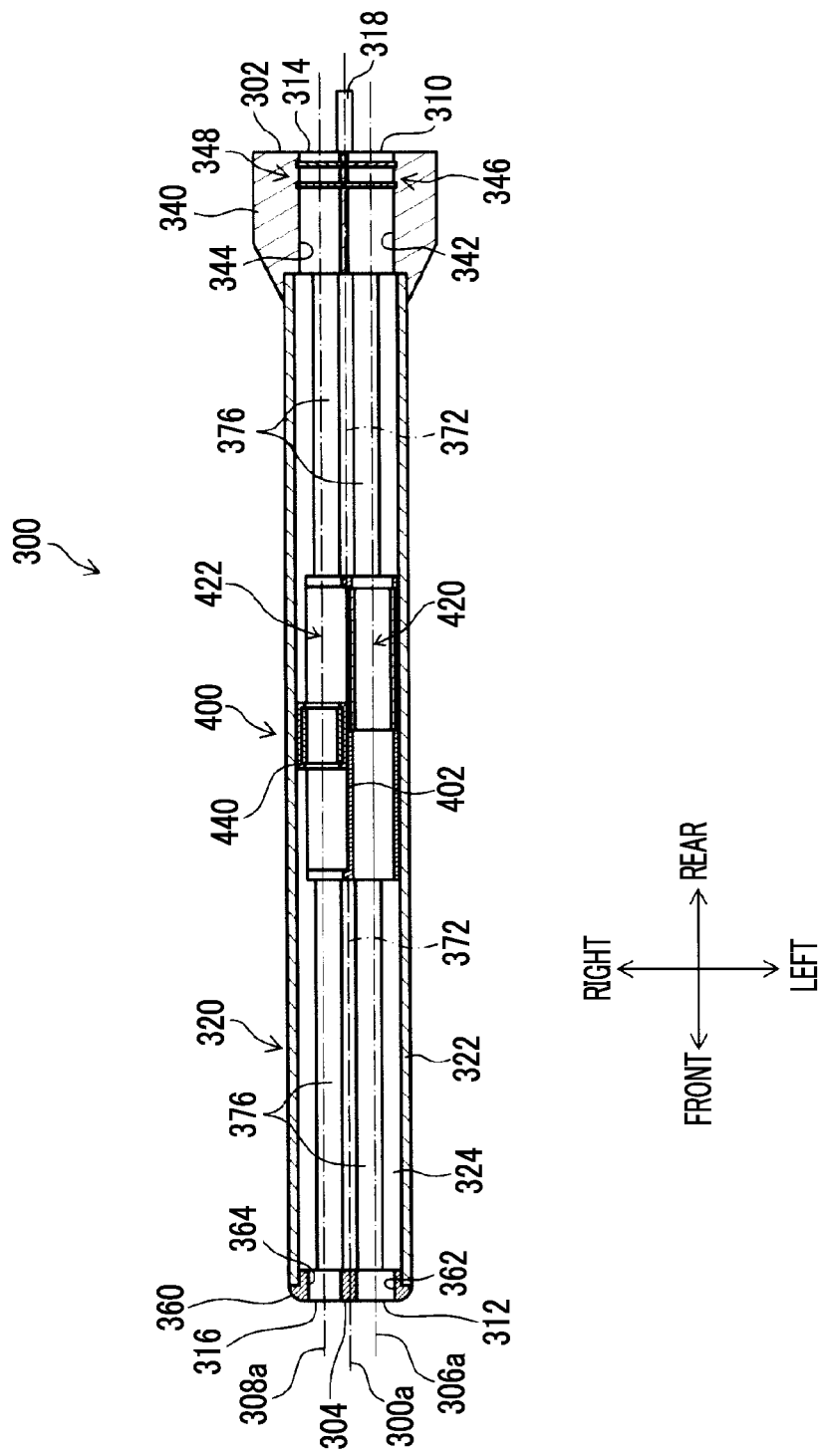
FIG. 4 is a sectional view, as seen from arrow 4-4 of FIG. 3, illustrating the internal structure of the overtube.

The specific configuration of the overtube 300 will be described. FIG. 4 is a sectional view (a sectional view as seen arrow 4-4 of FIG. 3) illustrating the internal structure of the overtube 300, and illustrates a section cut in a plane that includes the reference axis 300a and orthogonal to an upward-downward direction. In the present specification, when a drawing is simply called a sectional view, the drawing illustrates a sectional view cut by the same plane as FIG. 4.

As illustrated in this drawing, the overtube 300 has an overtube body 320 that occupies substantially the entire area in a forward-rearward direction, a base end cap 340 that is arranged at a rear part of the overtube 300, a distal end cap 360 that is arranged at a distal end part, and a slider 400 (interlocking member) that is arranged inside the overtube 300. In addition, the base end cap 340 and the distal end cap 360 are some of the constituent elements of the overtube body of the invention, and may be formed separately from or formed integrally with the overtube body 320.

(Description of Overtube Body)

The overtube body 320 is formed in an elongated cylindrical shape having the reference axis 300a as a central axis using hard resin, metal, or the like, and has an outer wall 322 that surrounds an outer periphery, and a lumen 324 that penetrates from a base end of the overtube body 320 to a distal end thereof.

The lumen 324 has the endoscope insertion axis 306a and the treatment tool insertion axis 308a inserted therethrough, and is provided with a space that serves as the endoscope insertion passage 306 and the treatment tool insertion passage 308.

Additionally, the lumen 324 serves as the air supply pipe line through which the pneumoperitoneum gas sent in from the air supply connector 318 passes.

The base end cap 340 is attached to the base end of the overtube body 320, and is formed in a columnar shape made to have a larger diameter than the external diameter of the overtube body 320, using hard resin, metal, or the like. The base end cap 340 has a flat rear end surface serving as the base end surface 302 of the overtube 300 on the rear side thereof, and has through-holes 342 and 344 that penetrate from the base end surface 302 to the lumen 324 of the overtube body 320.

The through-hole 342 has a central axis arranged coaxially with the endoscope insertion axis 306a, and forms a portion of the endoscope insertion passage 306. An opening of the through-hole 342 in the base end surface 302 is equivalent to the above-described endoscope insertion opening 310.

The through-hole 344 has a central axis arranged coaxially with the treatment tool insertion axis 308a, and forms a portion of the treatment tool insertion passage 308. An opening of the through-hole 344 in the base end surface 302 is equivalent to the above-described treatment tool insertion opening 314.

Valve members 346 and 348 (a first valve member 346, a second valve member 348) are respectively arranged in the through-hole 342 and the through-hole 344. Although the detailed description of the valve members 346 and 348 is omitted, the valve members have, for example, slits that open only when being inserted through the endoscope insertion part 102 and the treatment tool insertion part 202 and that come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of the pneumoperitoneum gas injected into the body cavity to the outside of the body.

In addition, the valve members 346 and 348 are not limited to those with the specific configuration, and valve members with widely-known arbitrary configurations can be used. Although FIG. 4 illustrates a configuration in which the two valve members are respectively arranged in the through-hole 342 and the through-hole 344, a configuration in which one valve member or three or more valve members are arranged may be adopted.

(Description of Air Supply Connector)

Figure 5:
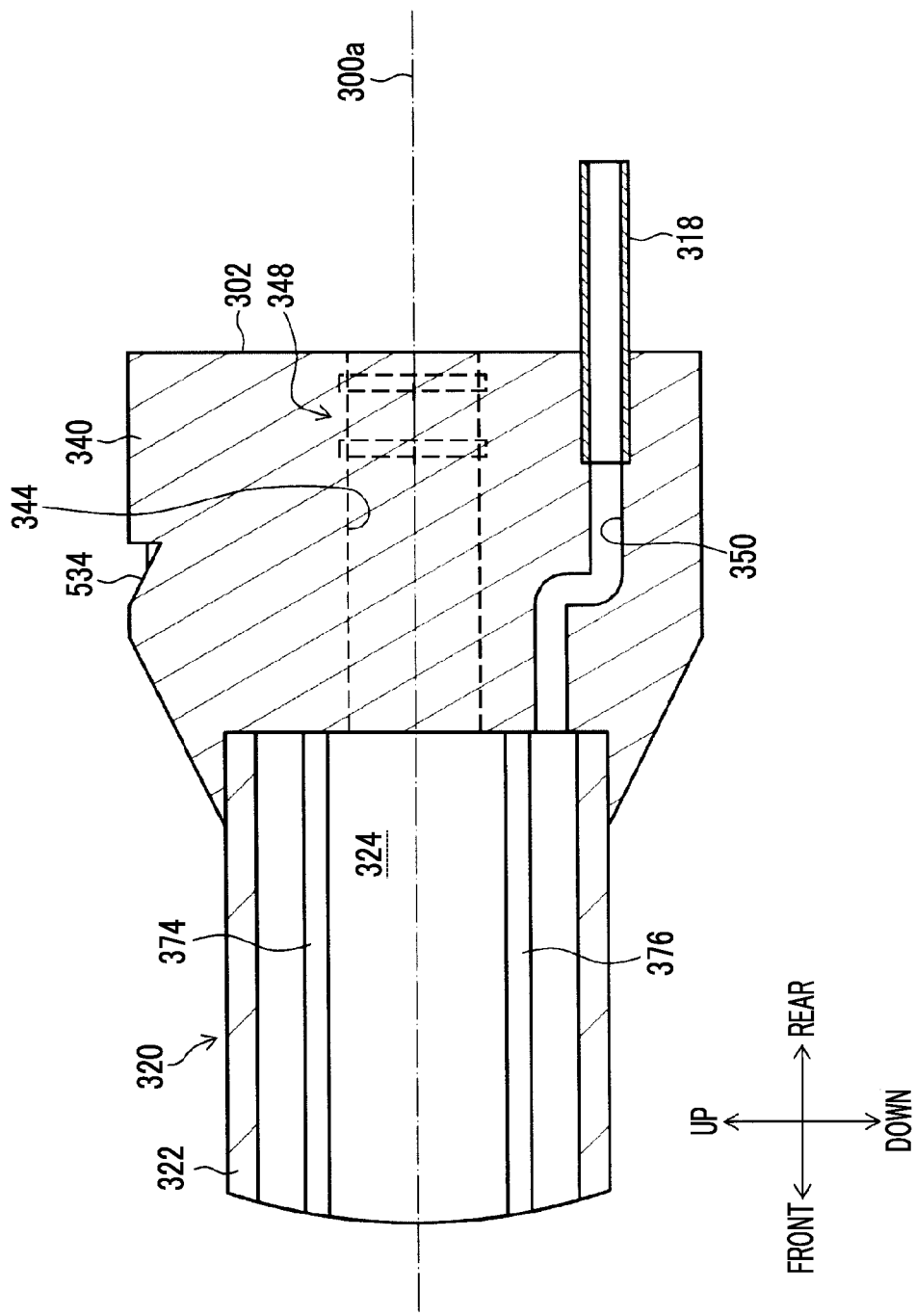
FIG. 5 is a sectional view of the periphery of a base end cap cut in a plane orthogonal to a paper surface of FIG. 4.

Additionally, FIG. 5 is a sectional view of the periphery of the base end cap 340 when the overtube 300 is cut in a plane that includes the reference axis 300a and is orthogonal to the paper surface of FIG. 4. As illustrated in this drawing, the base end cap 340 has a through-hole 350 that penetrates from the base end surface 302 to the lumen 324 of the overtube body 320.

The through-hole 350 is a portion of the air supply pipe line that allows the pneumoperitoneum gas to flow therethrough, and has a rear end part formed at a position below the reference axis 300a. The rear end part is provided with the above-described air supply connector 318 to which the air supply tube 122 (refer to FIG. 1) from the pneumoperitoneum device 120 is connected.

The air supply connector 318 is formed in an elongated cylindrical shape, and has a part buried and fixed inside the through-hole 350. Accordingly, at a position below the reference axis 300a in the base end surface 302, the axis (central axis) of the air supply connector 318 is arranged so as to be substantially orthogonal to the base end surface 302 (arranged parallel to the reference axis 300a), and the air supply connector 318 is provided to protrude rearward from the base end surface 302.

The air supply tube 122 is connected to the air supply connector 318 by fitting the air supply tube 122 to the outer periphery of the air supply connector 318. Then, if the pneumoperitoneum gas is delivered from the pneumoperitoneum device 120 to the air supply tube 122, the pneumoperitoneum gas is sent into the lumen 324 of the overtube body 320 from the air supply connector 318.

(Merits Based on Arrangement of Air Supply Connector on Base End Surface)

Here, in an overtube that guides one medical instrument into a body cavity, it is general that the air supply connector is provided not on a base end surface of the overtube but on a side surface thereof.

This is because the air supply connector may interfere with an inner needle supposing that the air supply connector is provided on the base end surface, and because the overtube can be rotated around the axis so as to prevent the interference of the air supply connector and the air supply tube with a body wall without influencing the position of the medical instrument inserted through the overtube even if the air supply connector is provided on the side surface.

On the other hand, in the overtube 300 of the present embodiment, if the overtube 300 is rotated around the axis, the position of the endoscope insertion part 102 and the treatment tool insertion part 202 changes. Therefore, a case where it is difficult to avoid any interference of the air supply connector 318 and the air supply tube 122 with the body wall while maintaining the positions of the endoscope insertion part 102 and the treatment tool insertion part 202 within the body cavity at positions desired by a surgeon may occur.

Thus, in the overtube 300 of the present embodiment, interference of the air supply connector 318 and the air supply tube 122 with the body wall is prevented by arranging the air supply connector 318 on the base end surface 302 of the overtube 300, and the interference of the air supply tube with the inner needle is avoided by devising the configuration of the inner needle as will be described below.

In addition, the air supply pipe line within the air supply connector 318 and the overtube 300 may be provided in order to supply fluids other than the pneumoperitoneum gas into a body cavity.

The distal end cap 360 illustrated in FIG. 4 is attached to the distal end of the overtube body 320, and is formed of hard resin, metal, or the like. The distal end cap 360 has a front surface serving as the distal end surface 304 of the overtube 300 on a front side thereof, and has through-holes 362 and 364 that penetrate from the lumen 324 of the overtube body 320 to the distal end surface 304.

The through-hole 362 has a central axis arranged coaxially with the endoscope insertion axis 306a, and forms a portion of the endoscope insertion passage 306. An opening of the through-hole 362 in the distal end surface 304 is equivalent to the above-described endoscope delivery opening 312.

The through-hole 364 has a central axis arranged coaxially with the treatment tool insertion axis 308a, and forms a portion of the treatment tool insertion passage 308. An opening of the through-hole 364 in the distal end surface 304 is equivalent to the above-described treatment tool delivery opening 316.

Additionally, as described above, the pneumoperitoneum gas sent into the lumen 324 of the overtube body 320 via the air supply tube 122, the air supply connector 318 of the base end cap 340, and the through-hole 350 from the pneumoperitoneum device 120 is delivered to the outside (the inside of a body cavity) via the through-hole 362 and the through-hole 364.

Although the overtube body 320, the base end cap 340, and the distal end cap 360 above form the outer wall of the overtube 300, the outer wall of the overtube 300 may not necessarily be constituted of these separated members.

The air supply pipe line of the overtube body 320 through which the pneumoperitoneum gas passes may be a lumen that is provided separately from the lumen 324.

(Description of Slider)

Next, the slider 400 will be described.

The slider 400 illustrated in FIG. 4 is housed within the lumen 324 of the overtube body 320, and is supported so as to be movable forward and backward in the direction of the reference axis 300a.

The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part or the treatment tool insertion part in the forward-rearward direction (axial direction) does not interlock with the movement of the other and a sensing zone where the forward and backward movement of either the endoscope insertion part or the treatment tool insertion part interlocks with the movement of the other.

That is, the endoscope insertion part 102 is adapted to interlock with the forward and backward movement of the treatment tool insertion part 202 in the axial direction with play.

Accordingly, when a surgeon has moved the treatment tool insertion part 202 forward and backward in the axial direction and when the axial displacement of the treatment tool insertion part 202 is large (when a forward and backward movement of a large amplitude has been performed), the endoscope insertion part 102 also moves in an interlocking manner forward, backward, upward, downward, rightward, and leftward. Thus, the visual field, orientation, and the like of the endoscope 100 can be changed as intended by a surgeon. Additionally, the visual field is always given to pick up an image of a treatment tool distal end, and consequently, an image that is optimal for treatment is automatically provided. When it is desired to check places other than the treatment part, the checking can be performed by moving forceps, and a surgeon can perform operations as desired. Therefore, an assistant (scopist) who operates the endoscope 100 apart from the surgeon can be made unnecessary, and a troublesome condition in which the surgeon should instruct an assistant about the visual field, orientation, and the like of the endoscope serially can be eliminated.

Additionally, when the axial displacement of the treatment tool insertion part 202 is small (when a forward and backward movement of a small amplitude has been performed), the endoscope insertion part 102 does not interlock. Therefore, the size of an object to be observed within an observation image can be prevented from fluctuating unnecessarily, a sense of perspective can be suitably maintained, and a stable observation image can be provided.

(Internal Structure of Slider)

The internal structure of the slider 400 will be described.

Figure 6:
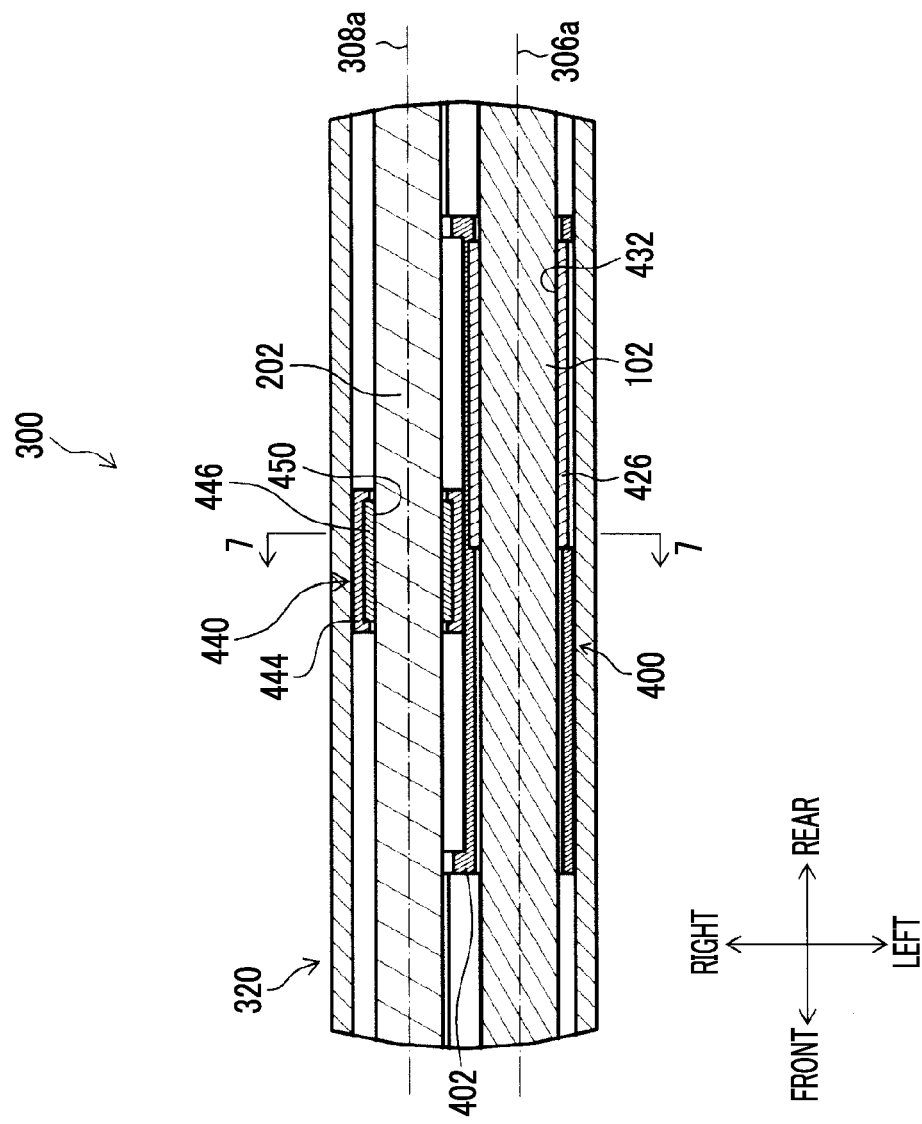
FIG. 6 is an enlarged sectional view illustrating a portion of FIG. 4 in an enlarged manner.

FIG. 6 is an enlarged sectional view illustrating a portion, in which the slider 400 is arranged in FIG. 4, in an enlarged manner, and illustrates a state where the endoscope insertion part 102 and the treatment tool insertion part 202 are inserted through the endoscope insertion passage 306 and the treatment tool insertion passage 308, respectively.

Figure 7:
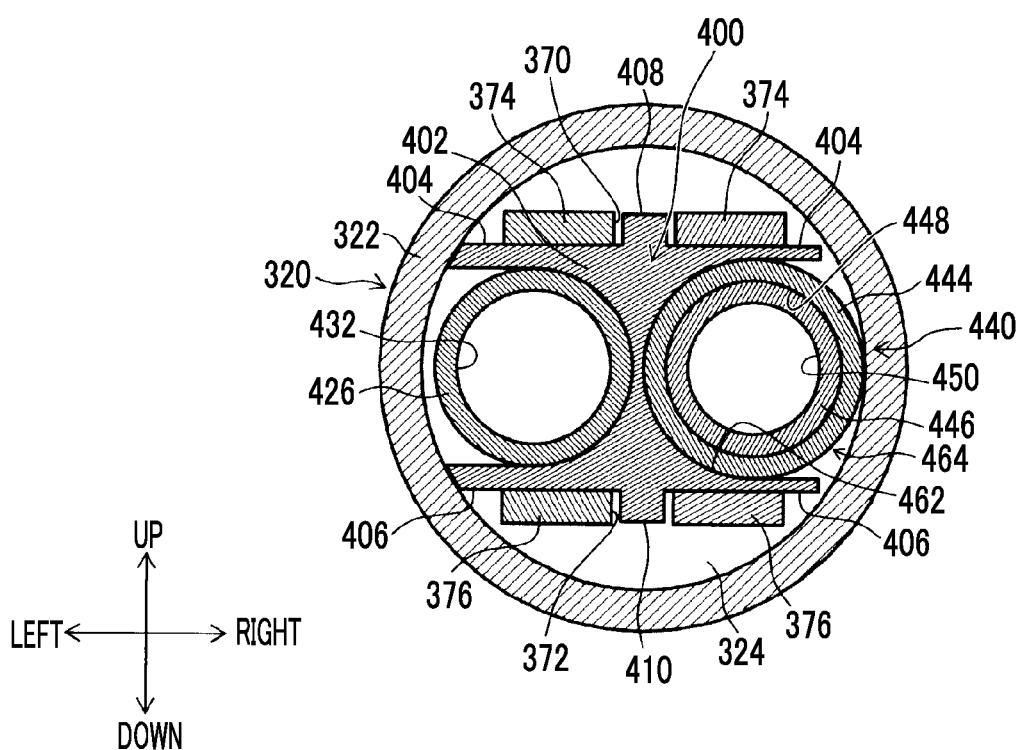
FIG. 7 is a sectional view as seen from arrow 7-7 in FIG. 6.

FIG. 7 is a sectional view as seen from arrow 7-7 in FIG. 6.

Figure 8:
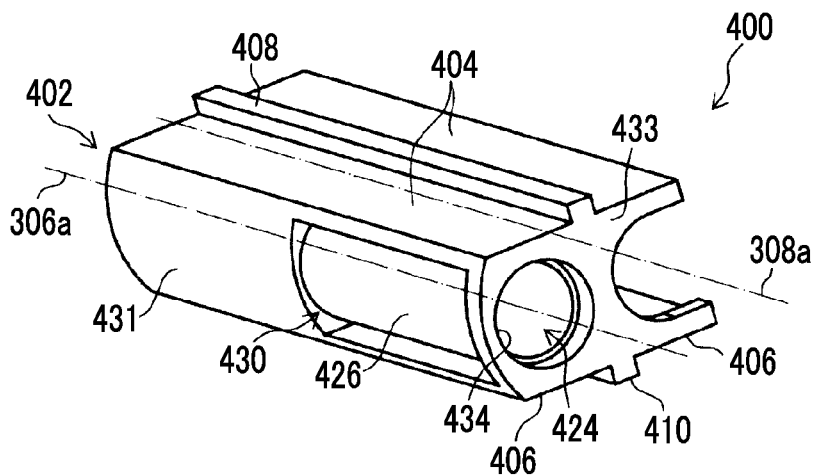
FIG. 8 is a perspective view illustrating a slider from the rear upper left.
Figure 9:
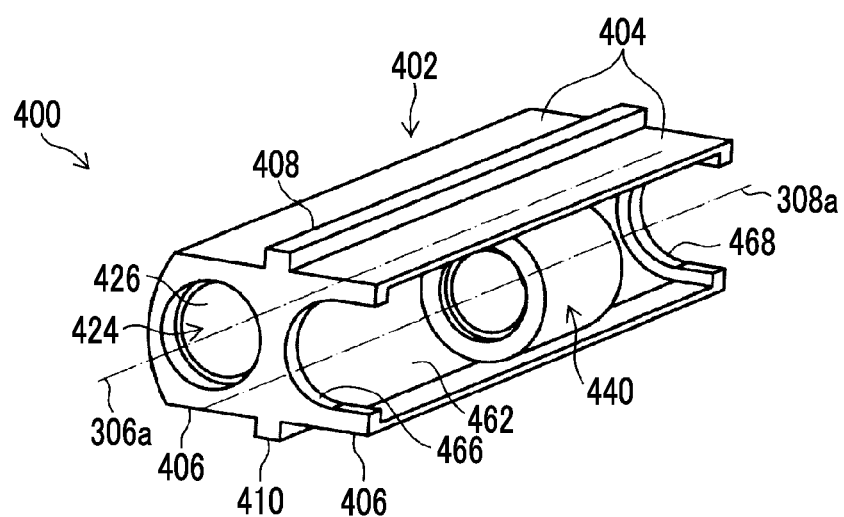
FIG. 9 is a perspective view illustrating the slider from the rear upper right.
Figure 10:
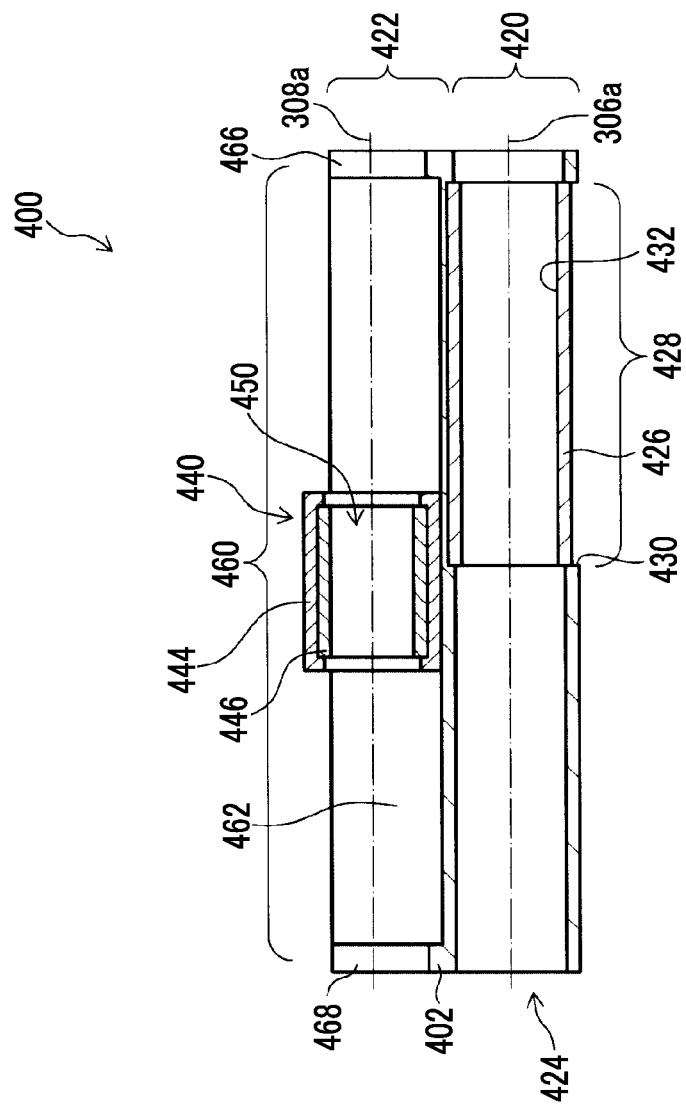
FIG. 10 is a sectional view of the slider.

Additionally, FIGS. 8 and 9 are respectively perspective views illustrating the slider 400 from the rear upper left and from the rear upper right and FIG. 10 is a sectional view of only the slider 400.

As illustrated in FIGS. 6 to 10, the slider 400 has a slider body 402 (slider member) that holds components of the slider 400. The slider body 402, as illustrated in FIGS. 7 to 9, has a flat upper surface 404 and a flat lower surface 406, and has protruding strips 408 and 410, respectively, on the upper surface 404 and the lower surface 406.

The protruding strips 408 and 410 respectively protrude in the upward-downward direction at substantially central parts of the upper surface 404 and the lower surface 406 in a leftward-rightward direction, extend in the direction (forward-rearward direction) of the reference axis 300*a* within the lumen 324 of the overtube body 320, and are fitted into guide grooves 370 and 372 provided in an upper part and a lower part within the lumen 324 of the overtube body 320 as illustrated in FIG. 7.

The guide grooves 370 and 372 are respectively formed by gaps between a pair of left and right guide plates 374 and 374 and a pair of left and right the guide plates 376 and 376 that are arranged at the upper part and the lower part within the lumen 324.

The guide plates 376 and 376 arranged at the lower part within the lumen 324 are illustrated in FIG. 4. As illustrated in this drawing, the guide plates 374 and 374 and the guide plates 376 and 376 are respectively formed in the shape of a long plate, and are installed along the direction of the reference axis 300*a* by being laid between the base end cap 340 and the distal end cap 360.

Accordingly, the guide grooves 370 and 372 are respectively arranged along the direction of the reference axis 300*a* from the base end cap 340 to the distal end cap 360 within the lumen 324.

As illustrated in FIG. 7, in a state where the slider 400 is housed and arranged within the lumen 324, the protruding strips 408 and 410 are respectively fitted into the guide grooves 370 and 372, and the upper surface 404 and the lower surface 406 respectively contact or approach the guide plates 374 and 374 and the guide plates 376 and 376. Accordingly, the slider 400 (slider body 402) is supported so as to be movable forward and backward in the forward-rearward direction within the lumen 324, and is supported in a state where the movement of the slider in the upward-downward direction and in the leftward-rightward direction and the rotation of the slider in all directions are restricted (a state where the rotation of the slider around at least the reference axis 300*a* is impossible).

In addition, the guide grooves 370 and 372 may not be formed by the guide plates 374 and 374 and the guide plates 376 and 376 arranged within the lumen 324 of the overtube body 320, and may be formed in the outer wall 322 of the overtube body 320 or may be formed by other configurations.

Additionally, a range (movable range) in which the slider 400 (slider body 402) moves forward and backward in the forward-rearward direction with respect to the overtube body 320 is a range having a position where the slider 400 abuts against the base end cap 340 as a rear end (a position closest to the base end) and having a position where the slider abuts against the distal end cap 360 as a front end (a position closest to the distal end). However, the rear end and the front end of the movable range of the slider 400 may not be restricted by the base end cap 340 and the distal end cap 360.

Additionally, the slider 400, as illustrated in FIG. 10, has an endoscope-coupled part 420 that is coupled (engaged) with the endoscope insertion part 102, and a treatment tool-coupled part 422 that is coupled (engaged) with the treatment tool insertion part 202.

(Description of Endoscope-Coupled Part)

The endoscope-coupled part 420 is provided on the left side of the slider body 402, and includes a through-hole 424 in which a space serving as the endoscope insertion passage 306 is secured within the lumen 324 of the overtube body 320 and through which, as illustrated in FIG. 6, the endoscope insertion part 102 is inserted, and a pressure-contact member 426 that is brought into pressure contact with the outer peripheral surface (side surface) of the endoscope insertion part 102 inserted through the endoscope insertion passage 306.

The through-hole 424 is formed to penetrate from a rear end of the slider body 402 to a front end thereof, and has a larger diameter than the external diameter of at least the endoscope insertion part 102. A central axis of the through-hole 424 is arranged coaxially with the endoscope insertion axis 306*a* within the lumen 324.

A pressure-contact member attachment part 428 for attaching the pressure-contact member 426 is provided on the rear end side of the through-hole 424.

The pressure-contact member attachment part 428 has an internal diameter that is made larger than other position ranges of the through-hole 424, and has formed therein an opening 430 (refer to FIG. 8) that penetrates up to an outer surface (left side surface 431) of the slider body 402 in a partial range thereof (a left side surface of the slider 400) in the circumferential direction. The pressure-contact member 426 is fitted into the through-hole 424 from the opening 430, and the pressure-contact member 426 is fixed to the slider body 402 in the pressure-contact member attachment part 428.

The pressure-contact member 426, as illustrated in FIG. 7, is annularly formed of an elastic material, such as elastic rubber or a spring, and a central axis of a through-hole 432 thereof is arranged coaxially with the endoscope insertion axis 306*a*.

Accordingly, when the endoscope insertion part 102 is inserted through the endoscope insertion passage 306, as illustrated in FIG. 6, the endoscope insertion part 102 is inserted through the through-hole 432 of the pressure-contact member 426.

In addition, the position of an outer peripheral surface of the pressure-contact member 426 in the opening 430 of the pressure-contact member attachment part 428 substantially coincides with the position of the left side surface 431 of the slider body 402 around the opening 430. That is, the opening 430 of the pressure-contact member attachment part 428 provides a space for arranging the pressure-contact member 426, and as compared to a configuration in which the pressure-contact member 426 is completely housed inside the slider body 402, the slider body 402 is miniaturized, and the external diameter of the overtube body 320 is also made smaller along with this miniaturization. However, a configuration in which the pressure-contact member 426 is completely housed inside the slider body 402 may be adopted.

Additionally, the internal diameter (the diameter of the through-hole 432) of the pressure-contact member 426 is slightly smaller than the external diameter of the endoscope insertion part 102.

Therefore, when the endoscope insertion part 102 is inserted through the through-hole 432 of the pressure-contact member 426, the through-hole 432 is pushed and widened and the pressure-contact member 426 is deformed. An elastic force is generated in the pressure-contact member 426 due to this deformation, and the pressure-contact member 426 is brought into pressure contact (engaged) with the endoscope insertion part 102 inserted through the through-hole 432.

Therefore, a frictional force acts on the relative movement between the endoscope insertion part 102 and the pressure-contact member 426. Then, unless a larger external force than the frictional force is applied between the endoscope insertion part 102 and the pressure-contact member 426, the relative movement does not occur between the endoscope insertion part 102 and the pressure-contact member 426, and the endoscope insertion part 102 and the slider 400 (slider body 402) are brought into a state where they are coupled (engaged) in an interlockable manner via the pressure-contact member 426.

Accordingly, the slider 400 (slider body 402) also integrally moves forward and backward in an interlocking manner with the forward and backward movement of the endoscope insertion part 102 in the forward-rearward direction (axial direction).

In addition, since the coupling here is based on the elastic force of the pressure-contact member 426, the engagement position (a position where the slider 400 is engaged in the endoscope insertion part 102) of the endoscope insertion part 102 coupled to the slider 400 (slider body 402) can be arbitrarily adjusted.

(Description of Treatment Tool-Coupled Part)

The treatment tool-coupled part 422, as illustrated in FIG. 10 is provided on the right side of the slider body 402, and includes a sleeve 440 (sleeve member) that is coupled to the treatment tool insertion part 202, and a guide part 460 that guides the sleeve 440 so as to be movable forward and backward in the direction (forward-rearward direction) of the treatment tool insertion axis 308a.

The sleeve 440 is housed in a sleeve housing space 464 of the guide part 460 to be described below in detail, is supported so as to be movable forward and backward in the forward-rearward direction, and as illustrated in FIG. 7, includes a sleeve body (frame body) 444 that surrounds the outside of the sleeve, and a pressure-contact member 446 that is arranged inside the sleeve.

The sleeve body 444 is formed in a cylindrical shape, and has a through-hole 448 with a larger diameter than the external diameter of at least the treatment tool insertion part 202. The central axis of the through-hole 448 is arranged coaxially with the treatment tool insertion axis 308a within the lumen 324 of the overtube body 320, and secures a space for the treatment tool insertion passage 308.

The pressure-contact member 446 is annularly formed of an elastic material, such as elastic rubber or a spring, and is fitted into the through-hole 448 of the sleeve body 444 and fixed to the sleeve body 444. A central axis of a through-hole 450 of the pressure-contact member 446 is arranged coaxially with the treatment tool insertion axis 308a within the lumen 324 of the overtube body 320.

Therefore, when the treatment tool insertion part 202 is inserted through the treatment tool insertion passage 308, as illustrated in FIG. 6, the treatment tool insertion part 202 is inserted through the through-hole 450 of the pressure-contact member 446.

Additionally, the internal diameter (the diameter of the through-hole 450) of the pressure-contact member 446 is slightly smaller than the external diameter of the treatment tool insertion part 202.

Therefore, when the treatment tool insertion part 202 is inserted through the through-hole 450 of the pressure-contact member 446, the through-hole 450 is pushed and widened and the pressure-contact member 446 is deformed. An elastic force is generated in the pressure-contact member 446 due to this deformation, and the pressure-contact member 446 is brought into pressure contact (engaged) with the treatment tool insertion part 202 inserted through the through-hole 450.

Therefore, a frictional force acts on the relative movement between the treatment tool insertion part 202 and the pressure-contact member 446. Then, unless a larger external force than the frictional force is applied between the treatment tool insertion part 202 and the pressure-contact member 446, the relative movement does not occur between the treatment tool insertion part 202 and the pressure-contact member 446, and the treatment tool insertion part 202 and the sleeve 440 are brought into a state where they are coupled (engaged) in an interlockable manner via the pressure-contact member 446.

Accordingly, the sleeve 440 also integrally moves forward and backward in an interlocking manner with the forward and backward movement of the treatment tool insertion part 202 in the forward-rearward direction (axial direction).

Additionally, the sleeve 440 also rotates with respect to the slider body 402 in an interlocking manner with the rotation around the axis of the treatment tool insertion part 202.

In addition, since the coupling between the treatment tool insertion part 202 and the sleeve 440 herein is based on the elastic force of the pressure-contact member 446, the engagement position (a position where the sleeve 440 is engaged in the treatment tool insertion part 202) of the treatment tool insertion part 202 coupled to the sleeve 440 can be arbitrarily adjusted.

Additionally, a region where the endoscope insertion part 102 is fixed to the endoscope-coupled part 420 of the slider 400 is referred to as an endoscope fixed region, and a region where the treatment tool insertion part 202 is fixed to the treatment tool-coupled part 422 of the slider 400 is referred to as a treatment tool fixed region. In the present form, the endoscope fixed region is equivalent to a region of an inner peripheral surface of the pressure-contact member 426 that is brought into pressure contact with the outer peripheral surface of the endoscope insertion part 102, and the treatment tool fixed region is equivalent to a region of an inner peripheral surface of the pressure-contact member 446 that is brought into pressure contact with the outer peripheral surface of the treatment tool insertion part 202. In this case, it is desirable that the endoscope fixed region is configured so as to become longer in the axial direction than the treatment tool fixed region.

Meanwhile, the guide part 460 of the treatment tool-coupled part 422, as illustrated in FIGS. 7 and 9, has a guide surface 462 that extends in the direction of the treatment tool insertion axis 308a (reference axis 300a) within the lumen 324 of the overtube body 320.

The guide surface 462 is curved in a U-shape toward an opening in a section orthogonal to the reference axis 300a, and as illustrated in FIG. 7, an inner peripheral surface of the overtube body 320 (outer wall 322) is arranged so as to face the opening of the guide surface 462, within the lumen 324 of the overtube body 320.

Accordingly, a space surrounded by the guide surface 462 and the inner peripheral surface of the overtube body 320 is formed as the sleeve housing space 464 of the guide part 460.

The sleeve housing space 464 is formed at a position where the treatment tool insertion axis 308a is inserted therethrough, and extends along the treatment tool insertion axis 308a.

The sleeve 440 is housed and arranged in the sleeve housing space 464 as described above, and a central axis of the sleeve 440 is arranged coaxially with the treatment tool insertion axis 308a.

In the sleeve housing space 464, an outer peripheral surface of the sleeve 440 comes in contact with or approaches the guide surface 462 and the inner peripheral surface of the overtube body 320.

Accordingly, in the sleeve housing space 464, the sleeve 440 is supported so as to be movable in the forward-rearward direction and rotatable around the axis, and is supported in a state where the movement of the sleeve in the upward-downward direction and in the leftward-rightward direction is restricted.

Additionally, the guide part 460 (slider body 402), as illustrated in FIGS. 9 and 10, has end edge parts 466 and 468, which are formed to protrude in a direction orthogonal to the guide surface 462 along an end edge of the guide surface 462, respectively, on the base end side and the distal end side thereof.

The end edge parts 466 and 468 abut against the end part of the sleeve 440 to restrict the movement of the sleeve 440, when the sleeve 440 arranged in the sleeve housing space 464 moves forward and backward in the forward-rearward direction.

Therefore, a range (movable range) where the sleeve 440 moves forward and backward in the forward-rearward direction with respect to the slider body 402 is limited with a position where the sleeve abuts against the end edge part 466 being defined as a rear end and a position where the sleeve abuts against the end edge part 468 being defined as a front end. However, the rear end and the front end of the movable range of the sleeve 440 may not be restricted by the end edge part 466 and the end edge part 468.

In addition, in the present embodiment, the sleeve housing space 464 of the guide part 460 is formed by the guide surface 462 of the slider body 402 and the inner peripheral surface of the overtube body 320. Therefore, as compared to a configuration in which the sleeve housing space 464 is formed only by the slider body 402 and the sleeve 440 is completely housed inside the slider body 402, the slider body 402 is miniaturized, and the external diameter of the overtube body 320 is also made smaller along with this miniaturization. However, a configuration in which the sleeve 440 is completely housed inside the slider body 402 may be adopted.

(Action of Slider when Endoscope and Treatment Tool are Coupled)

According to the slider 400 configured as described above, the endoscope insertion part 102 inserted through the endoscope insertion passage 306 of the overtube 300 and the slider body 402 are coupled, and the treatment tool insertion part 202 inserted through the treatment tool insertion passage 308 of the overtube 300 and the sleeve 440 are coupled.

Figure 11:
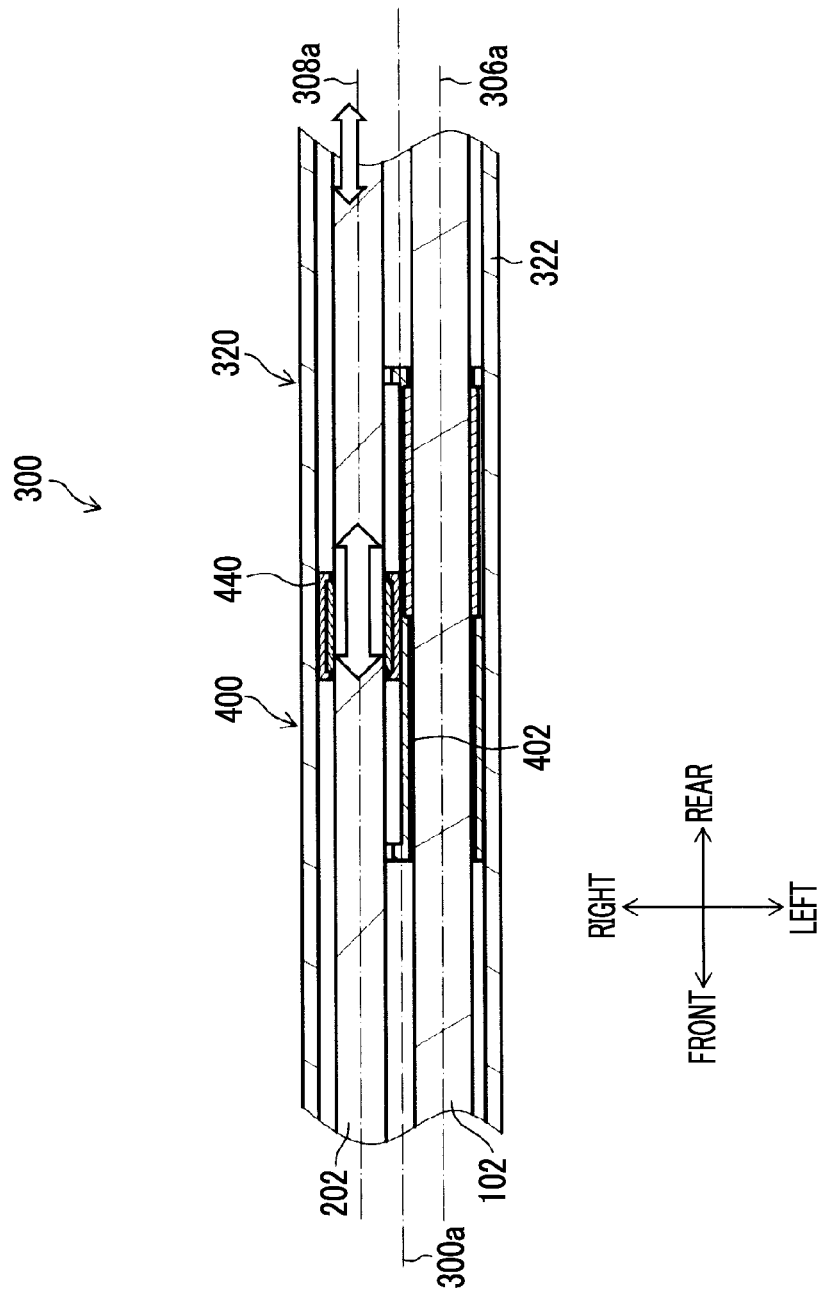
FIG. 11 is an explanatory view used for the description of the action of the slider.

As illustrated in FIG. 11, it is supposed that a surgeon performs a forward and backward movement for moving the treatment tool insertion part 202 forward and backward in the axial direction (forward-rearward direction) in a state where the sleeve 440 has not reached the rear end and the front end of the movable range thereof with respect to the slider body 402.

In this case, when the sleeve 440 has moved forward and backward within the movable range thereof with respect to the slider body 402, the slider body 402 does not move with respect to the forward and backward movement of the treatment tool insertion part 202. Therefore, the dead zone where the endoscope insertion part 102 does not interlock with the forward and backward movement of the treatment tool insertion part 202 is present.

Figure 12:
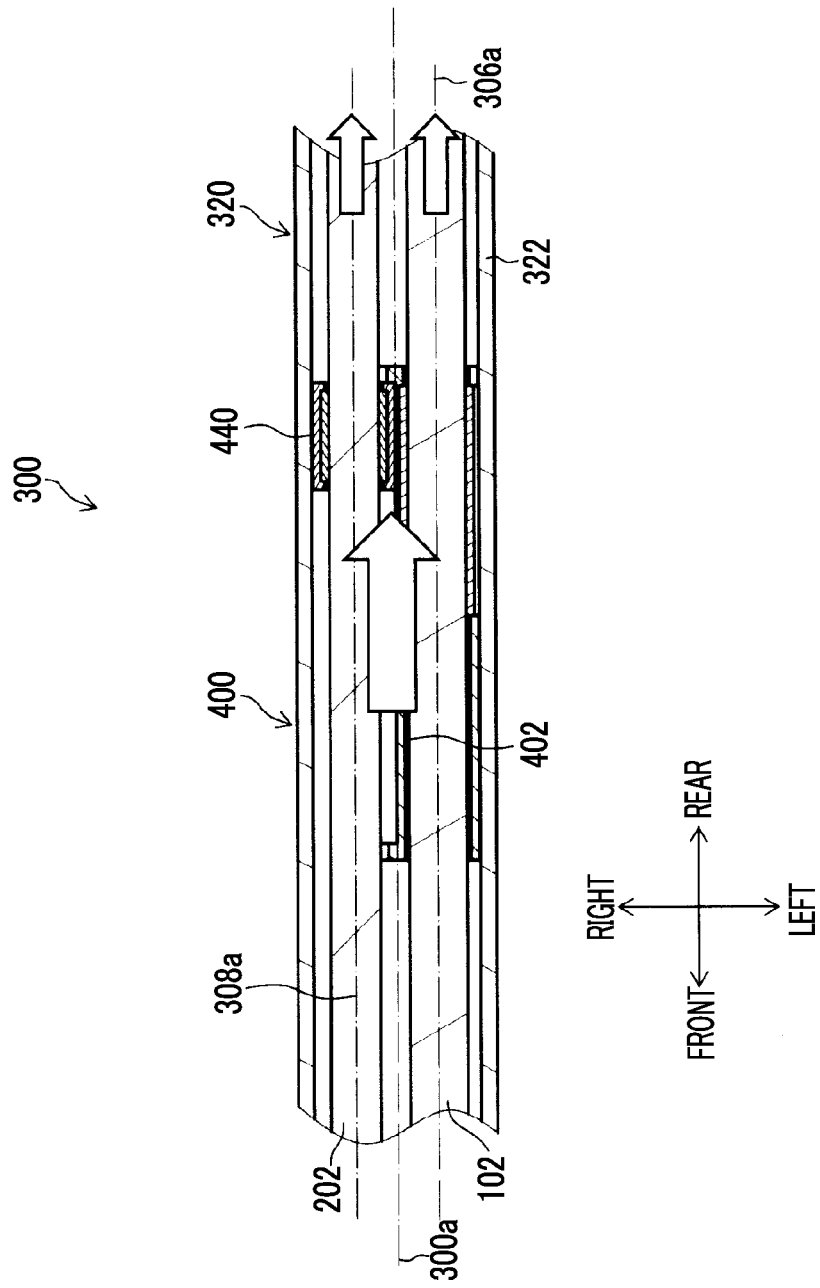
FIG. 12 is an explanatory view used for the description of the action of the slider.

On the other hand, as illustrated in FIG. 12, if the treatment tool insertion part 202 is moved backward in a state where the sleeve 440 reach the rear end of the movable range thereof with respect to the slider body 402, the sleeve 440 and the slider body 402 move backward with respect to the overtube body 320 together with the treatment tool insertion part 202. Accordingly, the endoscope insertion part 102 moves backward in an interlocking manner with the treatment tool insertion part 202.

Figure 13:
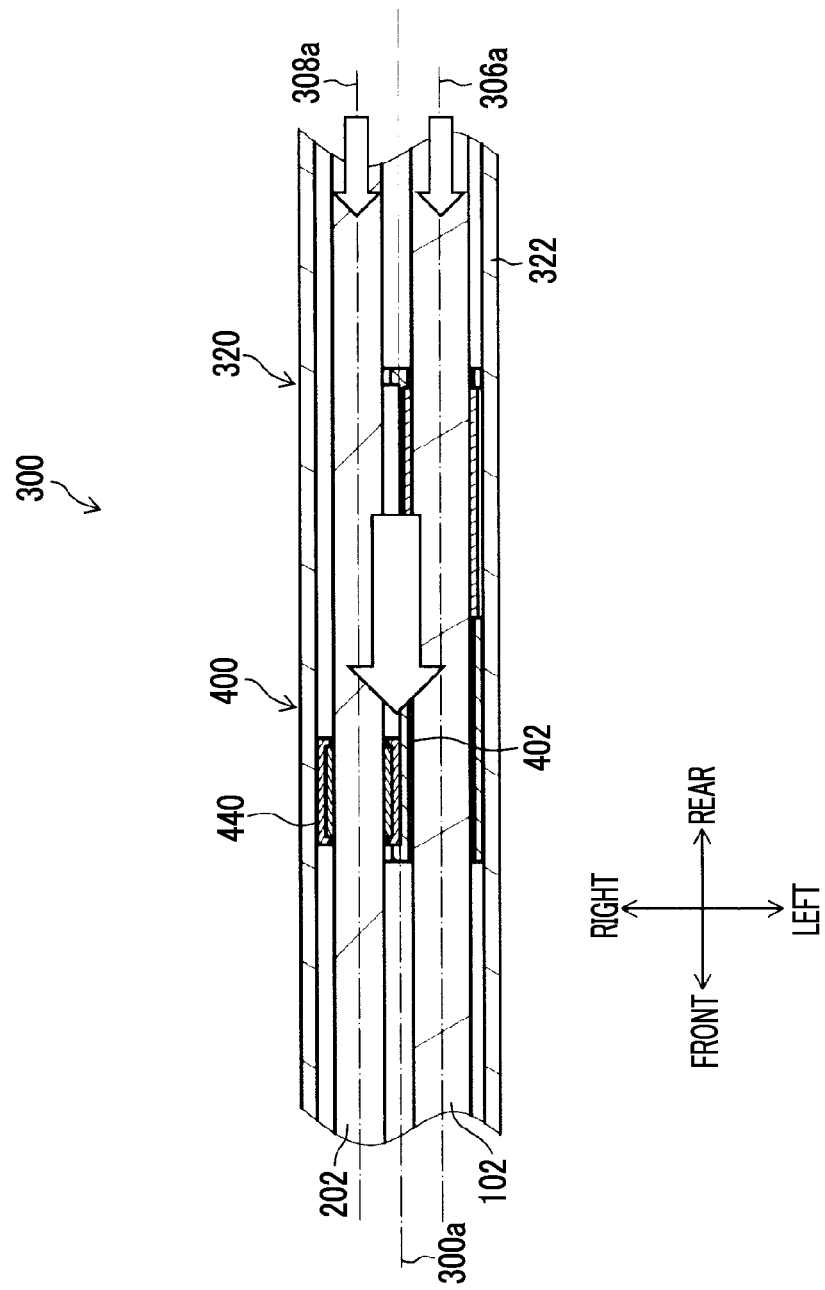
FIG. 13 is an explanatory view used for the description of the action of the slider.

Similarly, as illustrated in FIG. 13, if the treatment tool insertion part 202 is moved forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, the endoscope insertion part 102 moves forward in an interlocking manner with the treatment tool insertion part 202.

Therefore, when the treatment tool insertion part 202 has been largely displaced in the axial direction as described above (when the forward and backward movement of a large amplitude has been performed), the endoscope insertion part 102 is displaced in the axial direction in an interlocking manner with the treatment tool insertion part 202, and when the displacement of the treatment tool insertion part 202 in the axial direction is small (when the forward and backward movement of a small amplitude is performed), the endoscope insertion part 102 is not displaced in the axial direction.

Figure 14:
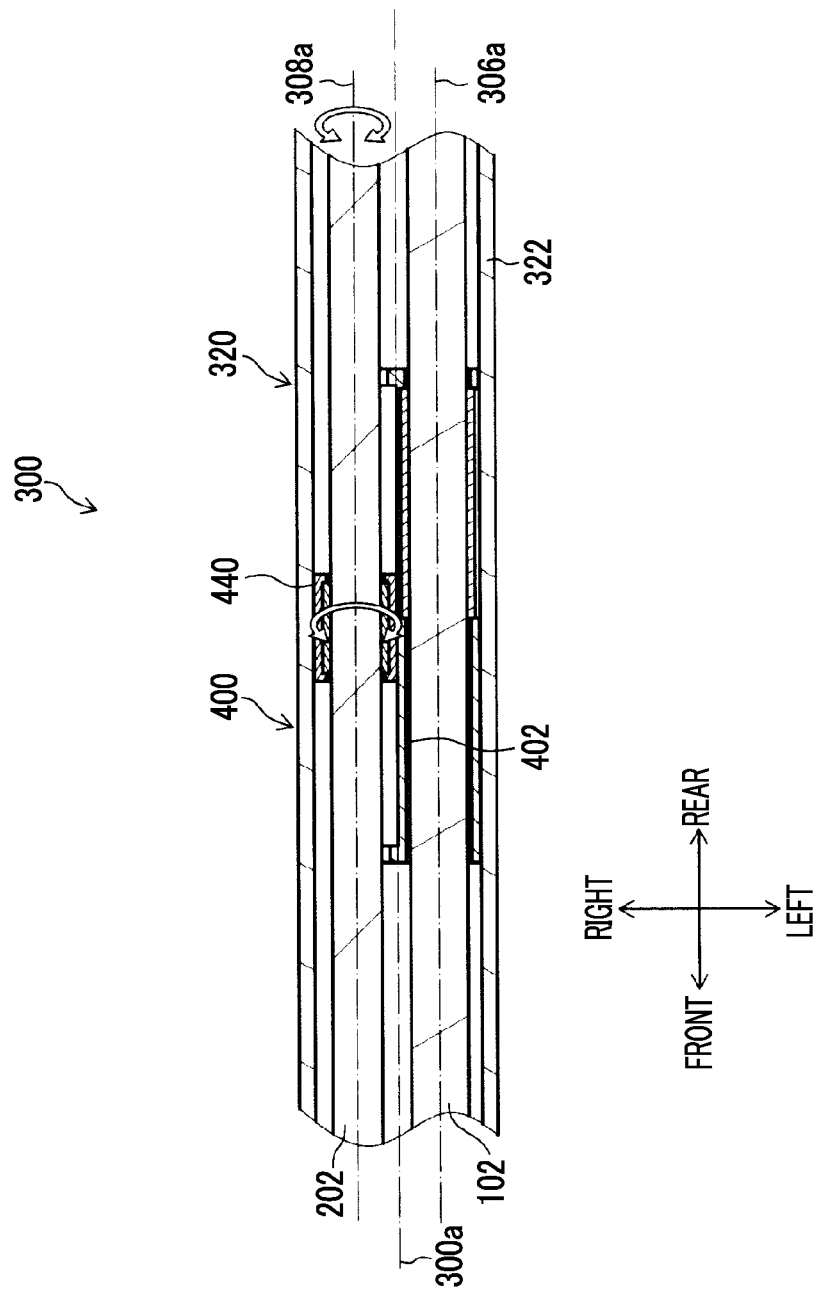
FIG. 14 is an explanatory view used for the description of the action of the slider.

Additionally, in the present embodiment, the slider body 402 is restricted only in forward and backward movement in the forward-rearward direction, whereas the sleeve 440 is supported so as to be rotatable around the axis with respect to the slider body 402. Therefore, as illustrated in FIG. 14, when the treatment tool insertion part 202 is operated to rotate around the axis, the slider body 402 does not rotate, and the treatment tool insertion part 202 and the sleeve 440 rotate around the axis.

Therefore, the rotational angle of the treatment tool insertion part 202 around the axis can be changed, without changing the positions of the endoscope insertion part 102 and the treatment tool insertion part 202 (the positions thereof within a body cavity) with respect to the overtube 300.

That is, when a treatment is performed on a predetermined affected part by inserting the endoscope insertion part 102 and the treatment tool insertion part 202 through the overtube 300 inserted into a body wall, in a general procedure, the endoscope 100 is used such that the position of the endoscope insertion part 102 in the upward-downward direction and in the leftward-rightward direction and the rotational angle thereof around the axis are fixed.

Meanwhile, the rotational operation of the treatment tool insertion part 202 around the axis is appropriately performed similar to the forward and backward movement so that the treatment tool 200 is easily operated by a surgeon.

In the overtube 300 of the present embodiment, the endoscope insertion part 102 and the treatment tool insertion part 202 are coupled by the slider 400. Thus, there is a concern that the positions of the endoscope insertion part 102 in the upward-downward direction and in the leftward-rightward direction and the rotational angle thereof around the axis may fluctuate due to the rotational operation or the like of the treatment tool insertion part 202.

However, since operations other than the forward and backward movement of the slider 400 are restricted as described above, the treatment tool insertion part 202 can be rotated around the axis without changing the positions of the endoscope insertion part 102 in the upward-downward direction and in the leftward-rightward direction and the rotational angle thereof around the axis, and the degree of freedom (five degrees of freedom) required for the operation of forceps operation is obtained. In addition, the five degrees of freedom of the operation of the forceps are the movement of the forceps with respect to an internal organ, and indicate five movements of the forceps including the movements of the forceps in the longitudinal direction, the transverse direction, and the forward and backward movement direction, the rotation of the forceps, and the opening/closing operation of the forceps.

(Operating Conditions of Slider)

Next, the operating conditions of the slider 400 will be described. Here, forces that act on the respective members related to the operation of the slider 400 are defined as follows.

A force with which the pressure-contact member 426 of the endoscope-coupled part 420 fixes the endoscope insertion part 102 at a fixed position of the outer peripheral surface thereof is referred to as a fixing force for fixing he slider body 402 to the endoscope insertion part 102, and the magnitude of the fixing force (the fixing force for fixing the endoscope insertion part 102 at the fixed position in the axial direction) with respect to the axial direction (forward-rearward direction) is defined as F1.

Similarly, a force with which the pressure-contact member 446 of the sleeve 440 in the treatment tool-coupled part 422 fixes the treatment tool insertion part 202 at a fixed position of the outer peripheral surface thereof is referred to as a fixing force for fixing the sleeve 440 to the treatment tool insertion part 202, and the magnitude of the fixing force with respect to the axial direction (forward-rearward direction) is defined as F2.

Meanwhile, a frictional force received from the valve member 346 when the endoscope insertion part 102 moves forward and backward is defined as F3, and a frictional force received from the valve member 348 when the treatment tool insertion part 202 moves forward and backward is defined as F4.

Additionally, a frictional force received from a peripheral member when the sleeve 440 moves forward and backward with respect to the slider body 402 is defined as F5, and a frictional force received from the peripheral member when the slider body 402 moves forward and backward with respect to the overtube body 320 is defined as F6.

(a) Conditions in which Endoscope and Treatment Tool are Interlocked with Each Other When Forward and Backward Movement Width of Treatment Tool is Large When the treatment tool insertion part 202 has been moved forward and backward (when the treatment tool insertion part has been markedly moved forward and backward), as conditions in which the endoscope insertion part 102 and the treatment tool insertion part 202 are integrally moved forward and backward via the slider 400, the fixing forces F1 and F2, and the frictional force F3 satisfy the following conditions (1) and (2).

$$F1 > F3 \quad (1)$$

$$F2 > F3 \quad (2)$$

Accordingly, if the sleeve 440 reaches the rear end or the front end of the movable range thereof with respect to the slider body 402 as illustrated in FIG. 12 or 13 when the treatment tool insertion part 202 has been moved forward and backward, the sleeve 440 receives the frictional force F3 of the valve member 346 via the slider body 402 and the endoscope insertion part 102. In this case, since the endoscope insertion part 102 and the slider body 402 are coupled by a larger fixing force F1 than the frictional force F3 and the treatment tool insertion part 202 and the sleeve 440 are coupled by a larger fixing force F2 than the frictional force F3, the slider body 402 moves forward and backward in an interlocking manner with the forward and backward movement of the treatment tool insertion part 202, and the endoscope insertion part 102 moves forward and backward in an interlocking manner with the forward and backward movement of the slider body 402.

Therefore, when the treatment tool insertion part 202 has been moved forward and backward, there is no case where, due to the frictional force of the valve member 346, the engagement position of the endoscope insertion part 102 engaged with the slider body 402 shifts and the engagement position of the treatment tool insertion part 202 engaged with the sleeve 440 also shifts.

In addition, when the treatment tool insertion part 202 has been moved forward and backward, as a condition for moving the slider body 402 forward and backward with respect to the overtube body 320 in an interlocking manner with this operation, the fixing force F2 and the frictional force F6 satisfy the following condition (3).

$$F2 > F6 \quad (3)$$

Similarly, when the endoscope insertion part 102 has been moved forward and backward, in order to move the endoscope insertion part 102 and the treatment tool insertion part 202 forward and backward integrally via the slider 400, the fixing forces F1 and F2, and the frictional force F4 satisfy the following conditions (4) and (5).

$$F1 > F4 \quad (4)$$

$$F2 > F4 \quad (5)$$

Additionally, when the endoscope insertion part 102 has been moved forward and backward, as a condition for moving the slider body 402 forward and backward with respect to the overtube body 320 in an interlocking manner with this operation, the fixing force F1 and the frictional force F6 satisfy the following condition (6).

$$F1 > F6 \quad (6)$$

(b) Conditions in Which Endoscope and Treatment Tool are not Interlocked with Each Other When Forward and Backward Movement Width of Treatment Tool is Small When the treatment tool insertion part 202 has been moved forward and backward with a small width, as a condition for moving only the treatment tool insertion part 202 forward and backward without moving the endoscope insertion part 102 forward and backward as illustrated in FIG. 11, the frictional forces F3, F5, and F6 satisfy the following condition (7).

$$F3+F6>F5 \quad (7)$$

As a result, as illustrated in FIG. 11, when the movement width of the treatment tool insertion part 202 is small, the endoscope insertion part 102 does not move, and when the forward and backward movement width of the treatment tool insertion part 202 is large, the endoscope insertion part 102 moves. That is, when the forward and backward movement width of the treatment tool insertion part 202 is small, the sleeve 440 moves forward and backward only within the slider body 402, and the slider body 402 itself does not move with respect to the overtube body 320. Thus, the endoscope insertion part 102 does not move forward and backward in the axial direction (forward-rearward direction).

In addition, since F6 is considered to be substantially 0 when the frictional resistance of the slider body 402 with respect to the overtube body 320 is small enough to be ignored compared to the frictional force between the endoscope insertion part 102 and the valve member 346, the condition (7) becomes F3>F5.

On the other hand, when the forward and backward movement width of the treatment tool insertion part 202 is large, the sleeve 440 moves forward and backward within the slider body 402, is struck against the distal end side or the base end side of the slider body 402 and moves the slider body 402 itself with respect to the overtube body 320. Thus, the endoscope insertion part 102 coupled to the slider body 402 also moves forward and backward.

(c) Conditions for Adjustment of Length of Treatment Tool Insertion Part 202

As a condition for adjusting the length of the treatment tool insertion part 202 while gripping the endoscope 100 and the treatment tool 200, it is preferable that the fixing force F1 and F2 satisfy the following condition (8).

$$F1>F2 \quad (8)$$

Accordingly, even when the treatment tool insertion part 202 has been moved forward and backward using the overtube body 320 or even when the treatment tool insertion part 202 has been moved forward and backward using the endoscope insertion part 102, the engagement position of the treatment tool insertion part 202 using the slider body 402 can be changed without changing the engagement position of the endoscope insertion part 102 engaged with the slider body 402.

When the length of the treatment tool insertion part 202 is adjusted by moving the treatment tool insertion part 202 forward and backward using the overtube body 320, frictional forces are generated between the sleeve 440 and the treatment tool insertion part 202 and between the valve member 348 and the treatment tool insertion part 202. Thus, the operating force required for the forward and backward movement of the treatment tool insertion part 202 is F2+F4. Therefore, in order to allow a surgeon to perform such an adjustment operation without feeling stress, it is desirable that the fixing force F2 and the frictional force F4 satisfy the following condition (9).

$$F2+F4<10 \text{ N (N is Newtons)} \quad (9)$$

Meanwhile, when the length of the treatment tool insertion part 202 is adjusted by moving the treatment tool insertion part 202 forward and backward using the endoscope insertion part 102, if F4>F3 is satisfied, the same frictional forces as above are generated. Thus, it is desirable to satisfy Expression (9). If F3<F4 is satisfied, frictional forces are generated between the sleeve 440 and the treatment tool insertion part 202 and between the valve member 346 and the endoscope insertion part 102. Thus the operating force required for the forward and backward movement of the treatment tool insertion part 202 is F2+F3. Therefore, in order to allow a surgeon to perform such an adjustment operation without feeling stress, it is desirable that the fixing force F2 and the frictional force F3 satisfy the following condition (10).

$$F2+F3<10 \text{ N (N is Newtons)} \quad (10)$$

The invention is effective not only when both of the condition (9) and the condition (10) are satisfied but also when only any one of these conditions is satisfied.

In addition, even when the fixing forces F1 and F2 satisfy the following Expression (11), the length of the treatment tool insertion part 202 can be adjusted. In this case, however, the engagement position between the endoscope insertion part 102 and the slider body 402 may move, and the positional adjustment between the slider body 402 and the endoscope insertion part 102 may be separately required.

$$F1<F2 \quad (11)$$

In order to allow a surgeon to perform such an adjustment operation without feeling stress, it is desirable that the fixing force F1 and the frictional force F3 or F4 satisfy the following condition (12) or (13).

$$F1+F4<10 \text{ N (N is Newtons)} \quad (12)$$

$$F1+F3<10 \text{ N (N is Newtons)} \quad (13)$$

(d) Conditions for Securing Excellent Operability

As a condition in which a surgeon can perform the forward and backward movement of the treatment tool insertion part 202 without feeling stress, it is preferable that the frictional forces F3, F4, and F6 satisfy the following condition (14).

$$F3+F4+F6<10 \text{ N (N is Newtons)} \quad (14)$$

In this way, by setting the required operating force (F3+F4+F6) when a surgeon moves the treatment tool insertion part 202 forward and backward markedly, a surgeon can secure excellent operability without feeling stress.

(e) Conditions for Preventing Overtube from Shifting with Respect to Body Wall

As a condition in which the overtube 300 (overtube body 320) is prevented from shifting due to the forward and backward movement of the treatment tool insertion part 202, if the fixing force of the overtube 300 in the forward-rearward direction (axial direction) with respect to a body wall is defined as Ft, the fixing force Ft and the frictional forces F3 and F4 satisfy the following condition (15).

$$Ft>F3+F4 \quad (15)$$

Accordingly, even if the treatment tool insertion part 202 has been moved forward and backward, the overtube 300 (overtube body 320) inserted into a body wall is fixed in a stable state without shifting. Thus, it is possible to secure excellent operability.

(Other Forms of Slider)

In the above overtube 300, a supporting mechanism of the slider 400 adapted to be capable of moving the slider 400 forward and backward only in the forward-rearward direction with respect to the overtube body 320 is not limited to the above form.

Figure 15:
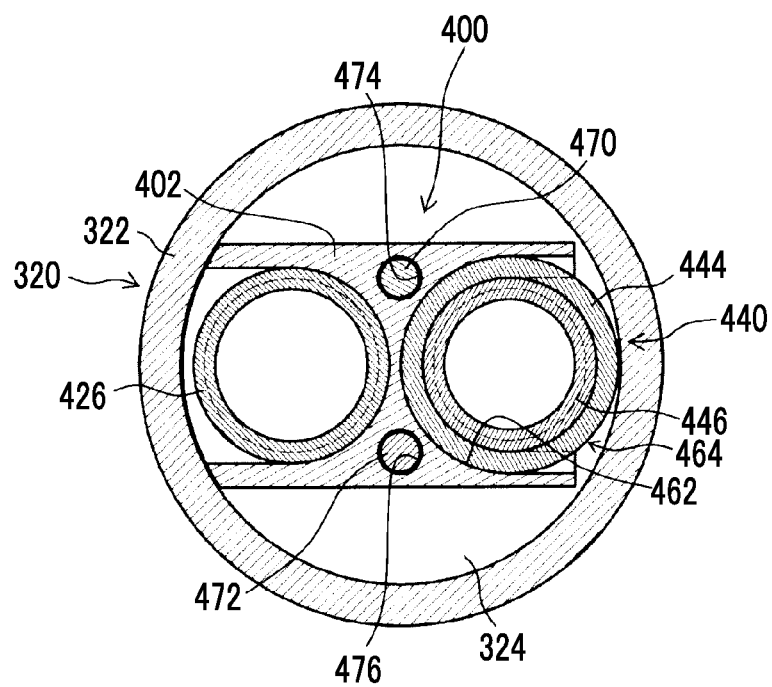
FIG. 15 is a sectional view illustrating another embodiment of the supporting mechanism of the slider in the overtube.

FIG. 15 is a sectional view illustrating another form of the overtube 300 by the section orthogonal to the reference axis 300a. In addition, the same reference signs will be given to constituent elements of the same or similar actions as those of the above form, and the description thereof will be omitted.

In the form illustrated in this drawing, guide rods 470 and 472, which are laid from the base end (base end cap 340) to the distal end (distal end cap 360), are arranged along the direction of the reference axis 300a at the upper part and the lower part within the lumen 324 of the overtube body 320.

Meanwhile, guide holes 474 and 476, which penetrate from the base end to the front end, are formed at the upper part and the lower part of the slider body 402 of the slider 400.

The guide rods 470 and 472 are respectively inserted through the guide holes 474 and 476, and the slider 400 is supported within the lumen 324.

Accordingly, the slider 400 is supported so as to be movable forward and backward only in the forward-rearward direction with respect to the overtube body 320.

Figure 16:
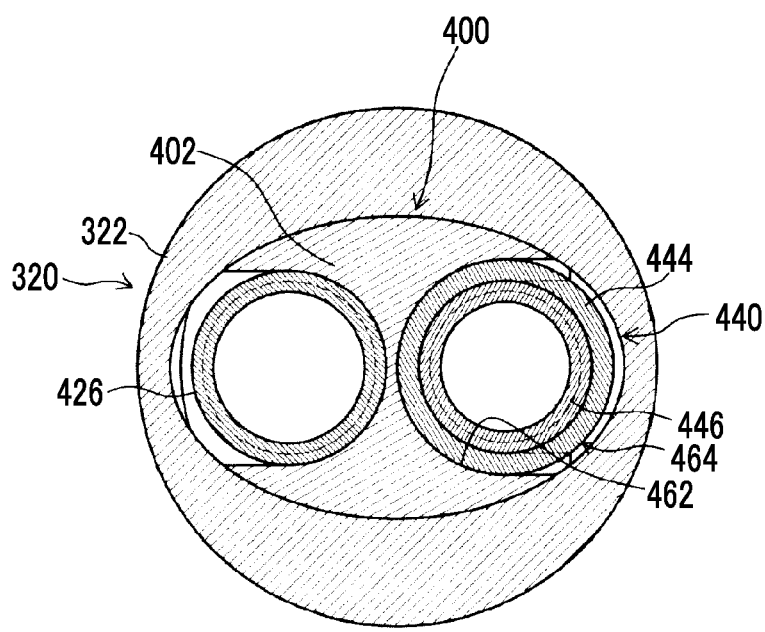
FIG. 16 is a sectional view illustrating another embodiment of the supporting mechanism of the slider in the overtube.

FIG. 16 is a sectional view illustrating another form of the overtube 300 by the section orthogonal to the reference axis 300a. In addition, the same reference signs will be given to constituent elements of the same or similar actions as those of the above form, and the description thereof will be omitted.

As illustrated in this drawing, the inner peripheral surface of the overtube body 320 (outer wall 322), that is, the outer shape of the lumen 324, is formed in an elliptical shape in the section orthogonal to the reference axis 300a.

Meanwhile, the slider 400 is formed so that the outer peripheral surface of the slider body 402 that is a frame body has a shape along an ellipse of the same shape as the lumen 324 in the section orthogonal to the reference axis 300a and the outer peripheral surface of the slider body 402 comes in contact with or approaches the inner peripheral surface of the overtube body 320.

Accordingly, the slider 400 is supported so as to be movable forward and backward only in the forward-rearward direction with respect to the overtube body 320.

In addition, the shape of the slider is not limited to this, and the shape of the inner peripheral surface of the overtube body 320 and the shape of the slider body 402 in the section orthogonal to the reference axis 300a only has to be a combination of non-rotatable shapes. For example, in the forms illustrated in FIGS. 7 and 15, if the shape of the inner peripheral surface of the overtube body 320 is formed in an elliptical shape as illustrated in FIG. 16 and the inner peripheral surface of the overtube body 320 is circumscribed on the slider body 402, similar to the form of FIG. 16, special guide means, such as the form of the protruding strips 408 and 410, the guide plates 374 and 376 in the form of FIG. 7 and the guide rods 470 and 472 and the guide holes 474 and 476 in the form of FIG. 15, can be made unnecessary.

(Description of Inner Needle)

Next, an inner needle 500 to be used after being mounted on the overtube 300 when the overtube 300 is inserted into a body wall will be described.

Figure 17:
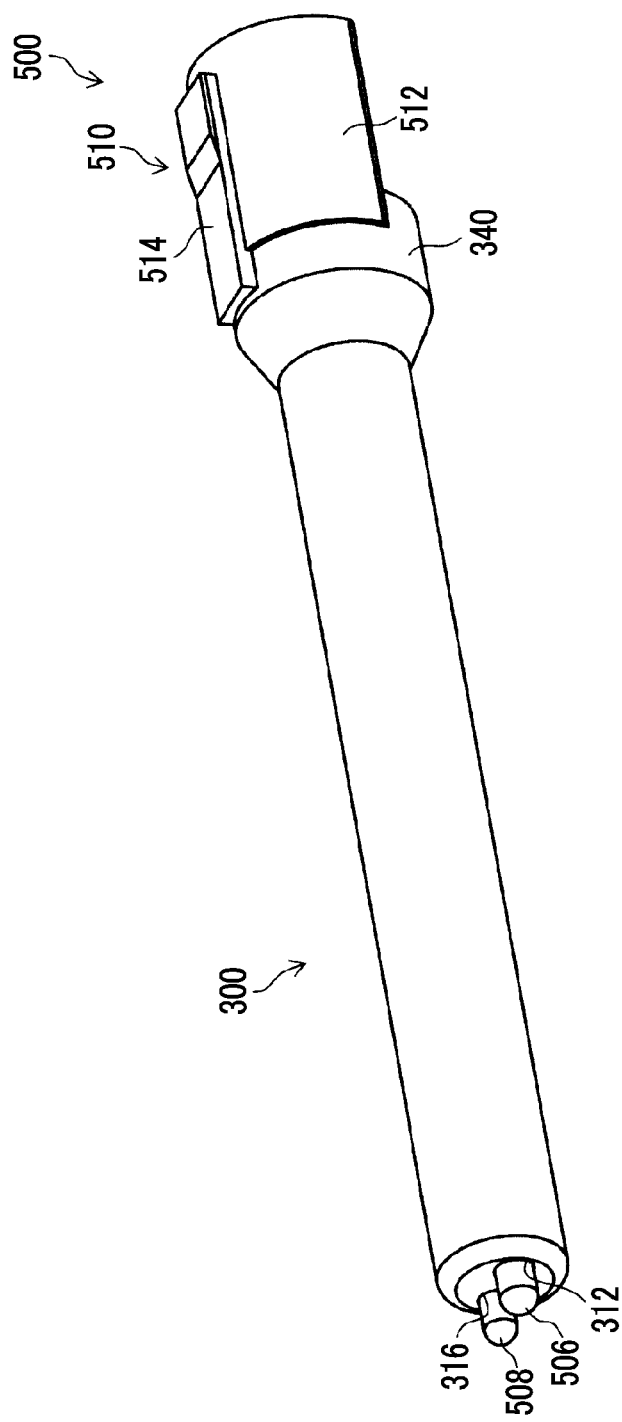
FIG. 17 is a perspective view illustrating a state where an inner needle has been mounted on the overtube, from the front upper left.
Figure 18:
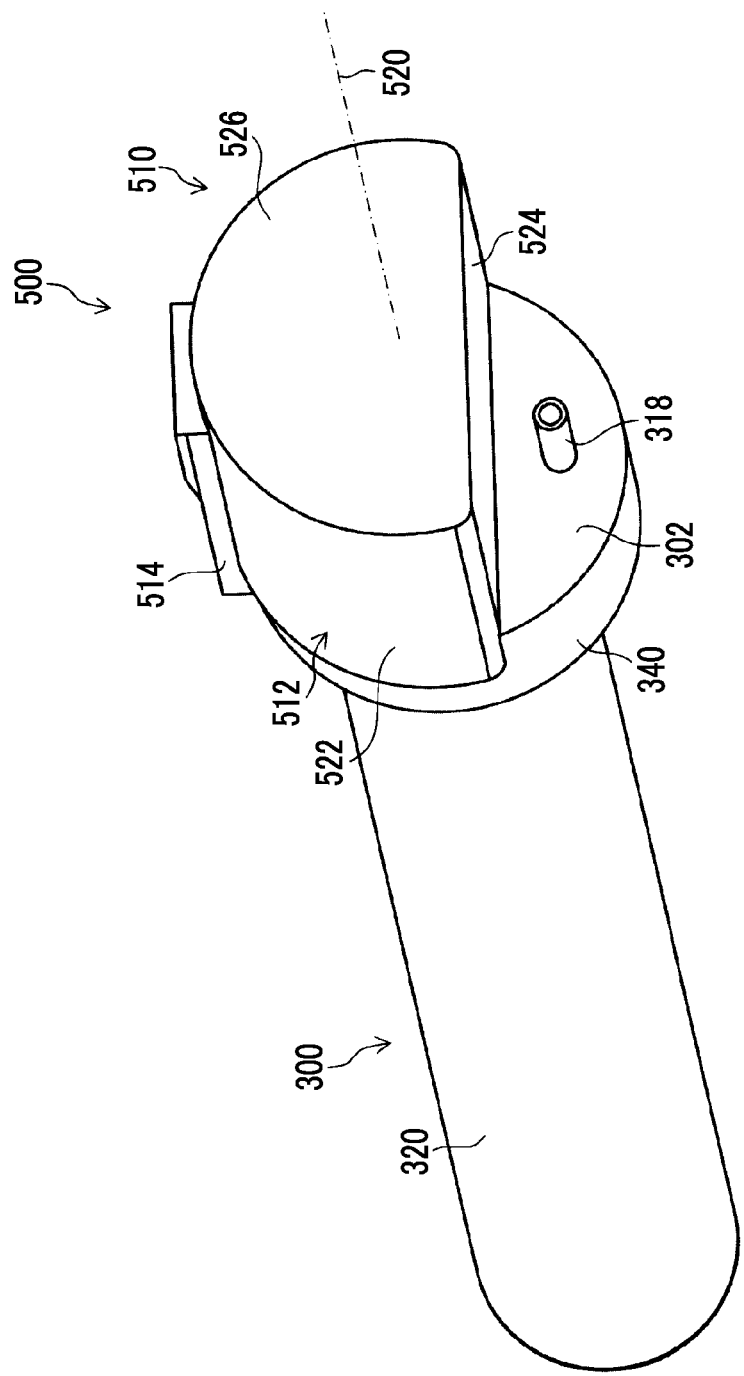
FIG. 18 is a perspective view illustrating a state where the inner needle has been mounted on the overtube, from the rear lower left.
Figure 19:
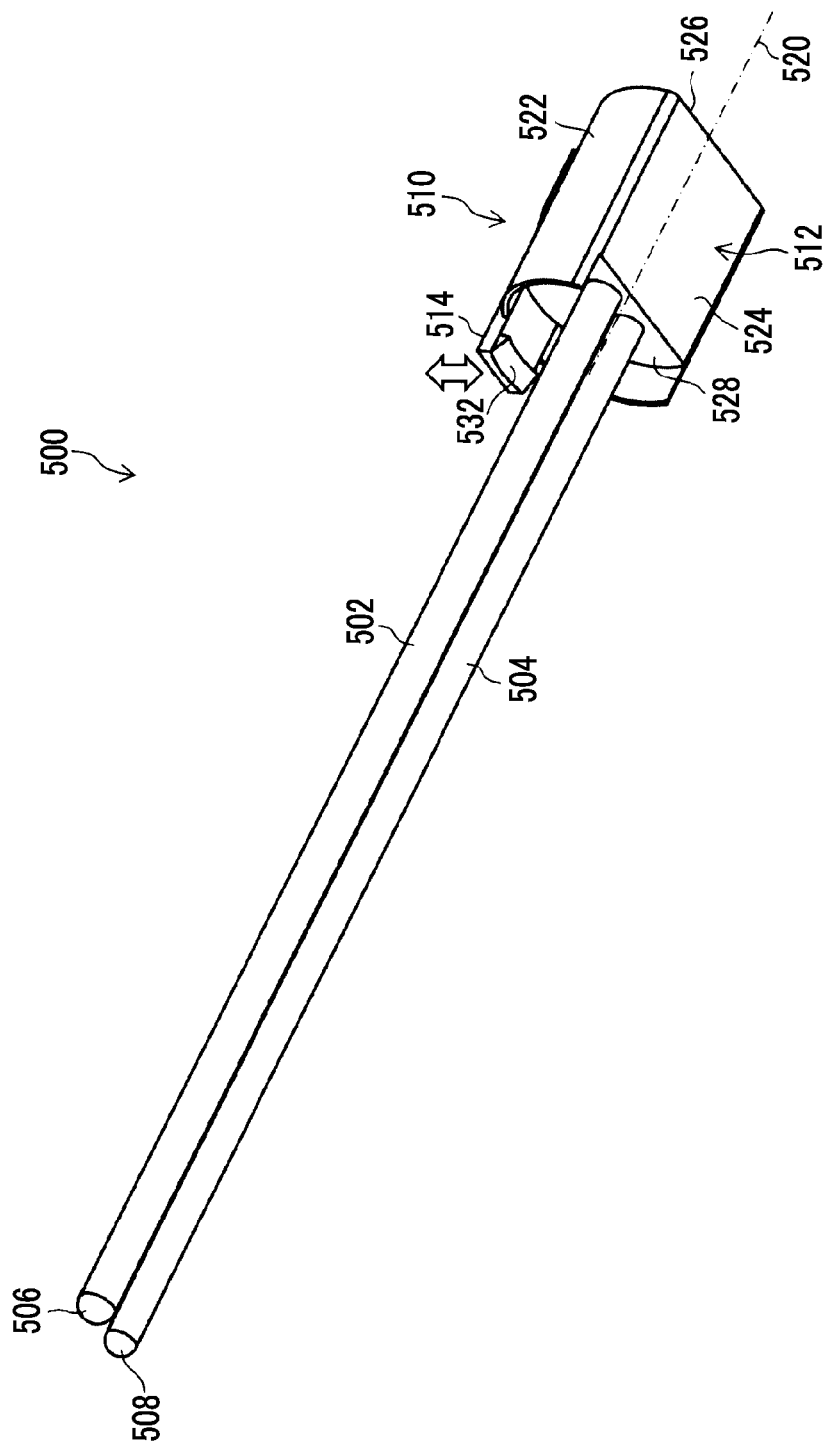
FIG. 19 is a perspective view illustrating the inner needle from the front lower left.

FIGS. 17 and 18 are respectively perspective views illustrating a state where the inner needle 500 has been mounted on the overtube 300 from the front upper left and from the rear lower left, and FIG. 19 is a perspective view illustrating only the inner needle 500 from the front lower left. In addition, the relationship of front and rear, left and right, and up and down of the inner needle 500 follows the relationship of front and rear, left and right, and up and down of the overtube 300 when being mounted on the overtube 300 as illustrated in FIG. 17.

As illustrated in these drawings, the inner needle 500 is constituted of two shaft parts 502 and 504 that are formed in an elongated shape, distal end parts 506 and 508 that are respectively formed at the distal ends of the shaft parts 502 and 504, and a head part 510 that is provided on the base end sides of the shaft parts 502 and 504.

The shaft part 502 (first shaft part) has a diameter equal to or smaller than the external diameter of the above-described endoscope insertion part 102, and is formed with a size such that the shaft part is insertable through the endoscope insertion passage 306. As illustrated in FIGS. 17 and 18, when the inner needle 500 is mounted on (incorporated into) the overtube 300, the shaft part 502 is arranged so as to be inserted through the endoscope insertion passage 306 of the overtube 300.

Additionally, the shaft part 502 is formed to be slightly longer than the length of the overtube 300 (endoscope insertion passage 306) in the forward-rearward direction, and when the inner needle 500 has been mounted on the overtube 300, the distal end part 506 of the shaft part 502 protrudes by a predetermined length from the endoscope delivery opening 312.

The shaft part 504 (second shaft part) has a diameter equal to or smaller than the external diameter of the above-described treatment tool insertion part 202, and is formed with a size such that the shaft part is insertable through the treatment tool insertion passage 308. As illustrated in FIGS. 17 and 18, when the inner needle 500 has been mounted on the overtube 300, the shaft part 504 is arranged so as to be inserted through the treatment tool insertion passage 308 of the overtube 300.

Additionally, the shaft part 504 is formed to be slightly longer than the length of the overtube 300 (treatment tool insertion passage 308) in the forward-rearward direction, and when the inner needle 500 has been mounted on the overtube 300, the distal end part 508 of the shaft part 504 protrudes by a predetermined length from the treatment tool delivery opening 316.

Although the distal end parts 506 and 508 are formed in a curved surface shape and are configured to be dull so that no edge is formed (that is, in a rounded non-edge shape), the distal end parts are adapted to be capable of penetrating a body wall easily.

The head part 510 has a head part body 512 and a locking lever 514.

The head part body 512, as illustrated in FIGS. 18 and 19, has a shape surrounded by a side surface 522 along a column surface having an axis 520 extending in the forward-rearward direction in parallel with the shaft parts 502 and 504 as a center having a diameter that approximately coincides with the external diameter of the base end cap 340 of the overtube 300, a lower surface 524 along a plane which is parallel to the axis 520 (parallel to the forward-rearward direction and the leftward-rightward direction) and which intersects the column surface along which the side surface 522 runs, and a rear end surface 526 and a front end surface 528 along a plane orthogonal to the axis 520.

In addition, the axis 520 is arranged coaxially with the reference axis 300a (not illustrated) of the overtube 300 in a state where the inner needle 500 has been mounted on the overtube 300.

The front end surface 528 of the head part body 512 has the base end sides of the shaft parts 502 and 504 fixed thereto, and the side surface 522 of the head part body 512 has the locking lever 514 provided along the direction (forward-rearward direction) of the axis 520 at a central part (topmost part) thereof in the circumferential direction.

The locking lever 514 is a constituent element of a fixing mechanism that detachably fixes the head part 510 of the inner needle 500 to the overtube 300, is formed in an elongated plate shape extending along the direction of the axis 520 (refer to FIG. 17), and is supported by the head part body 512 so as to be turnable in such an orientation that a front end part and a rear end part are opposite to each other in the upward-downward direction with the vicinity of the center in the direction of the axis 520 as a fulcrum.

A locking claw 532 (refer to FIG. 19) is provided to protrude from a lower surface side of a distal end part of the locking lever 514, and the locking claw 532, as illustrated in FIGS. 3 and 5, has such a shape that the locking claw is fitted to a locking hole 534 provided in the base end cap 340.

Additionally, a biasing member, such as a coil spring, is arranged at the head part body 512 at a position on a lower surface side of a base end part of the locking lever 514, and the locking lever 514 is biased so that the rear end part faces up and the front end part faces down.

(Action when Inner Needle is Mounted)

Figure 20:
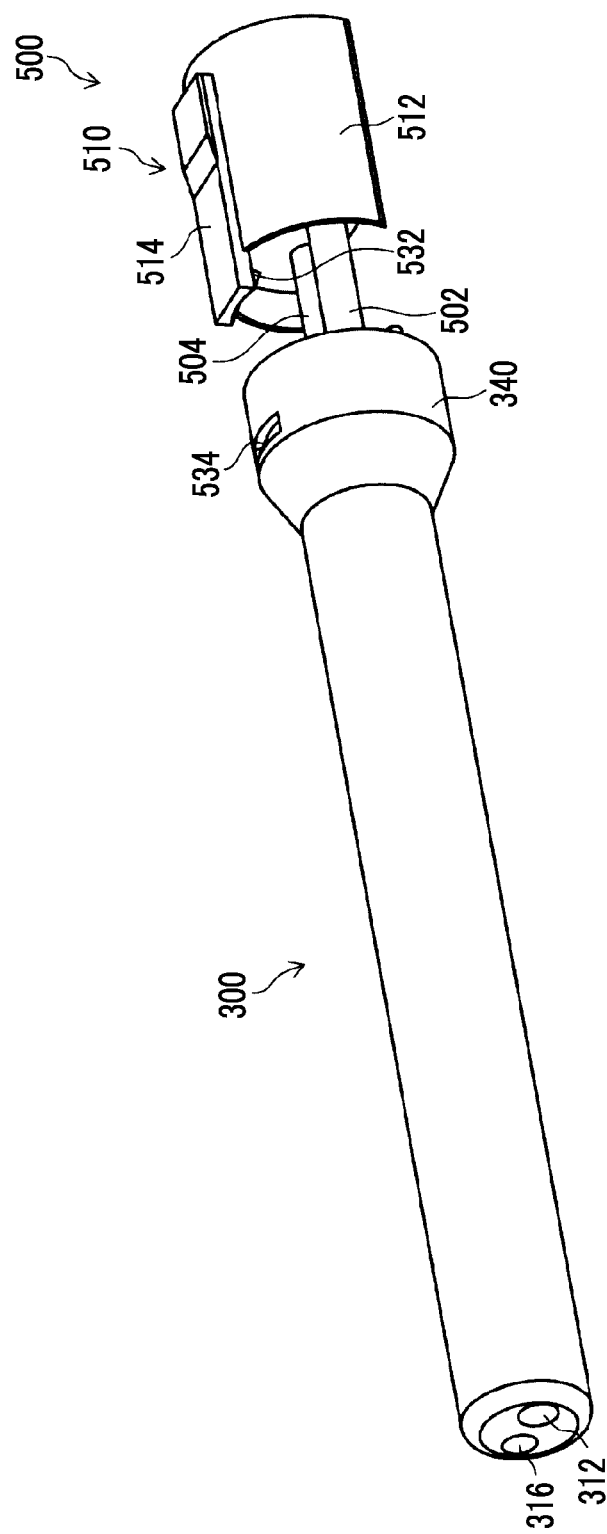
FIG. 20 is a perspective view illustrating a situation in which the inner needle is mounted on the overtube.

According to the inner needle 500 configured as above, if the shaft parts 502 and 504 of the inner needle 500 are respectively inserted into the endoscope insertion passage 306 and the treatment tool insertion passage 308 from the endoscope insertion opening 310 and the treatment tool insertion opening 314, respectively, of the overtube 300, as illustrated in FIG. 20, the head part 510 of the inner needle 500 approaches the base end cap 340 of the overtube 300.

Then, if the inner needle 500 is further inserted, as illustrated in FIGS. 17 and 18, the front end surface 528 of the head part body 512 abuts against the base end surface 302 of the overtube 300 (base end cap 340), and the locking claw 532 of the locking lever 514 is fitted to the locking hole 534 of the base end cap 340 and is brought into a state where the inner needle 500 has been mounted on (fixed to) the overtube 300.

In this case, the distal end parts 506 and 508 of the shaft parts 502 and 504 of the inner needle 500 are arranged so as to protrude by a predetermined length from the distal end of the overtube 300.

Meanwhile, if the base end part of the locking lever 514 is pressed in a state where the inner needle 500 has been mounted on the overtube 300, the locking claw 532 can be removed from the locking hole 534 of the base end cap 340, and if the inner needle 500 is pulled out to the hand side in that state, the inner needle 500 can be detached from the overtube 300.

Additionally, as described above, the head part body 512 of the inner needle 500 has such a shape that a lower side of a columnar member is cut out by the lower surface 524. That is, the head part body 512 is provided with a cutout part formed by cutting out a portion that interferes with the air supply connector 318 when the inner needle 500 has been mounted on the overtube 300.

Accordingly, the front end surface 528 of the head part body 512 can be made to abut against the base end surface 302 without interfering with the air supply connector 318 provided to protrude from the base end surface 302 of the overtube 300 (base end cap 340) as illustrated in FIG. 18 when the inner needle 500 has been mounted on the overtube 300, and the inner needle 500 can be mounted on the overtube 300 in a stable state.

In addition, the invention is not limited to the above form, and the head part body 512 only has to have the cutout part formed by cutting out the portion of the head part body 512 that interferes with at least the air supply connector 318 when the inner needle 500 has been mounted on the overtube 300. Additionally, since the rotation of the head part body 512 is restricted with respect to the overtube 300 by the shaft parts 502 and 504, the head part body does not interfere with the air supply connector 318.

(Description of Side Hole Openable and Closable by Slider)

Next, the characteristic parts of the invention will be described. In addition, in the following, the same reference signs will be used for constituent elements of the same or similar actions as the constituent elements in the above basic configuration, and the description thereof will be omitted, and only differences from the above basic configuration will be described.

In the overtube 300 illustrated in FIGS. 3 to 10 in the basic configuration of the above-described endoscopic surgical device 10, the pneumoperitoneum gas sent into the overtube 300 from the air supply connector 318 is delivered from the endoscope delivery opening 312 or the treatment tool delivery opening 316 of the distal end surface 304 of the overtube 300 to the outside (the inside of a body cavity).

In this case, the pneumoperitoneum gas is not easily delivered from the endoscope delivery opening 312 or the treatment tool delivery opening 316 in a state where the endoscope insertion part 102 and the treatment tool insertion part 202 are respectively inserted through both the endoscope insertion passage 306 and the treatment tool insertion passage 308 of the overtube 300.

Thus, the overtube 300 in the present embodiment described below has a configuration in which the pneumoperitoneum gas sent into the overtube 300 from the air supply connector 318 can be easily delivered to a body cavity, even in a state where the endoscope insertion part 102 and the treatment tool insertion part 202 are respectively inserted through the endoscope insertion passage 306 and the treatment tool insertion passage 308 of the overtube 300.

Figure 21:
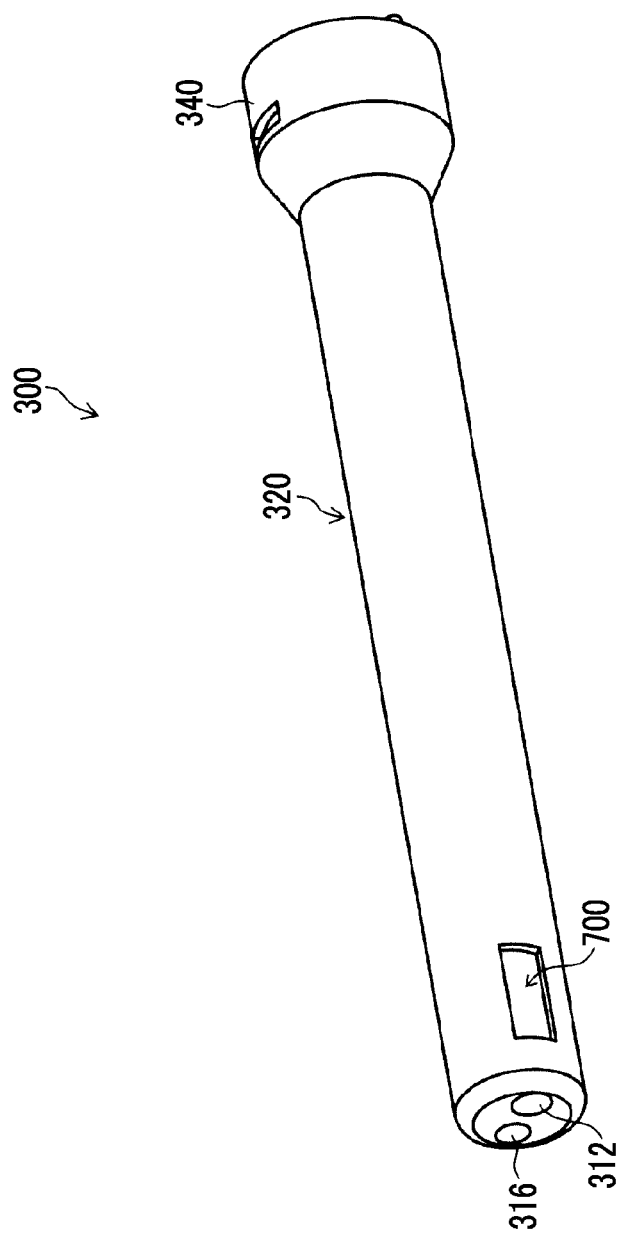
FIG. 21 is an external appearance perspective view illustrating the overtube in the endoscopic surgical device to which the present invention is applied.
Figure 22:
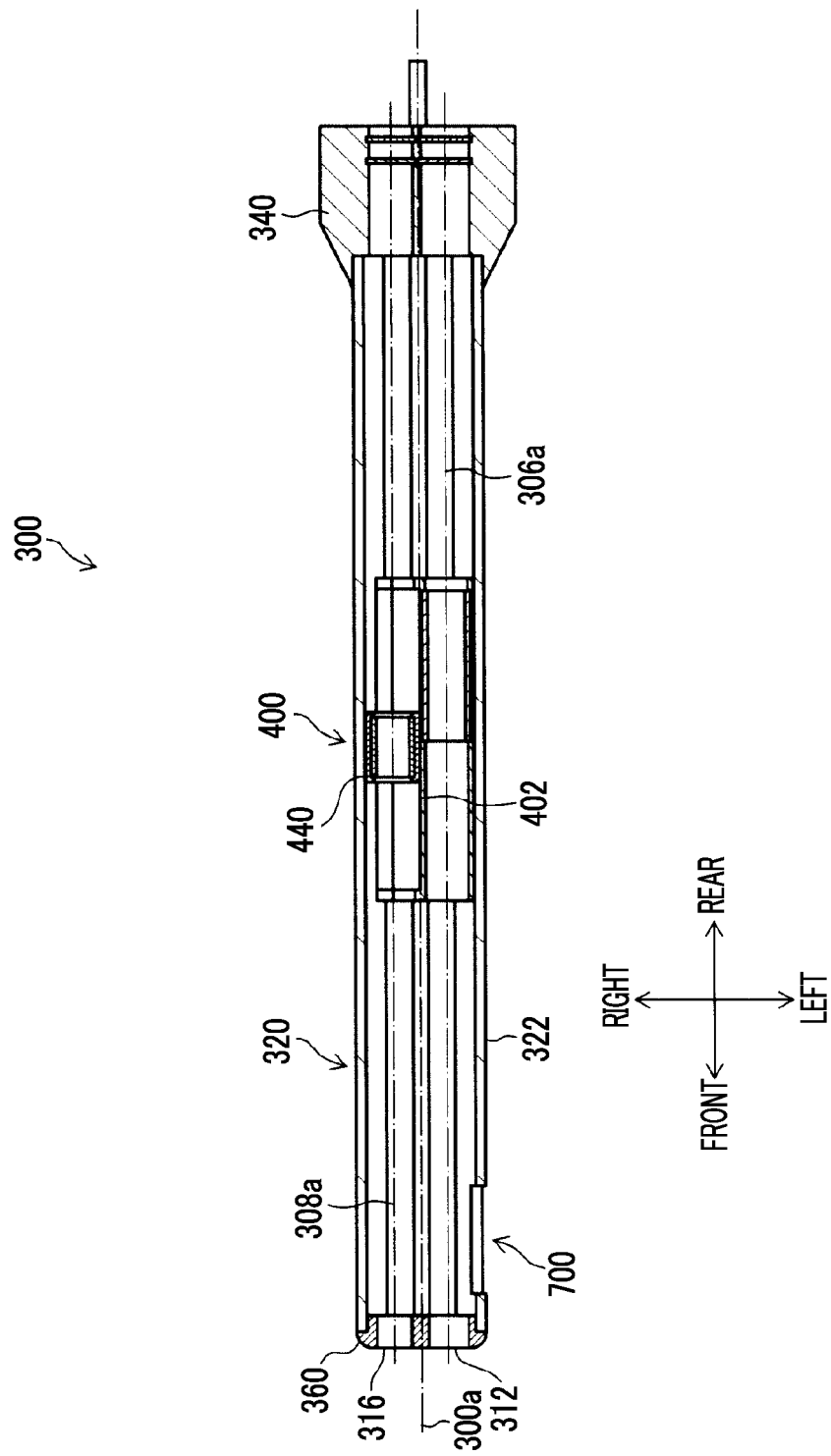
FIG. 22 is a sectional view illustrating the overtube in the endoscopic surgical device to which the present invention is applied.

FIGS. 21 and 22 are an external appearance perspective view and a sectional view illustrating the overtube 300 in the present embodiment.

As illustrated in these drawings, a side hole 700 (side surface opening) is provided in a side wall in the vicinity of the distal end of the overtube body 320 of the overtube 300.

The side hole 700 is a hole that is formed to penetrate from an outer peripheral surface to an inner peripheral surface in an outer wall 322 of the overtube body 320, and is formed in a rectangular shape. However, the side hole 700 may not have a rectangular shape, or may have other shapes, such as a round shape or an elliptical shape.

According to the side hole 700, a space (an inner cavity of the overtube 300) within the lumen 324 of the overtube body 320 and a space outside (body cavity) the overtube 300 communicate with each other.

Therefore, even in a state where the endoscope insertion part 102 and the treatment tool insertion part 202 are inserted through the endoscope insertion passage 306 and the treatment tool insertion passage 308 of the overtube 300, the pneumoperitoneum gas sent into the lumen 324 of the overtube body 320 from the air supply connector 318 of the base end cap 340 passes through the side hole 700 and is excellently delivered to the outside (the inside of a body cavity).

Meanwhile, as illustrated in FIGS. 21 and 22, in a case where when the side hole 700 is provided in the overtube body 320, tissue or blood in a body wall may enter the lumen 324 from the side hole 700 when the overtube 300 is inserted into the body wall. If tissue or blood in a body wall enters the lumen 324, there is a concern that dirt may adhere to the endoscope 100 or the movement of the slider 400 within the overtube 300 may be harmfully affected.

Thus, in order to prevent this, in the present embodiment, the side hole 700 is closed in an openable and closable manner by the slider 400 when the overtube 300 is inserted into a body wall.

That is, as illustrated in FIG. 8, the slider body 402 has a left side surface 431, which is one wall surface that contacts or approaches the inner peripheral surface of the overtube body 320 (outer wall 322), on the left side where the endoscope-coupled part 420 is provided.

In addition, the left side surface 431 shows the range of a surface that is arranged to approach or contact the inner peripheral surface of the overtube body 320, and shows a range closer to the front side than a front end position of the opening 430 of the slider body 402 in the present embodiment. However, the pressure-contact member attachment part 428 in which the opening 430 is provided may not necessarily be located at a position near the rear end side of the slider body 402, or may be located in the vicinity of the front end side or center of the slider body 402. In that case, a continuous surface, which is a side surface that is provided closer to the front side or the rear side than the opening 430 of the pressure-contact member attachment part 428 and is arranged to approach or contact the inner peripheral surface of the overtube body 320, is equivalent to the left side surface 431.

Figure 23:
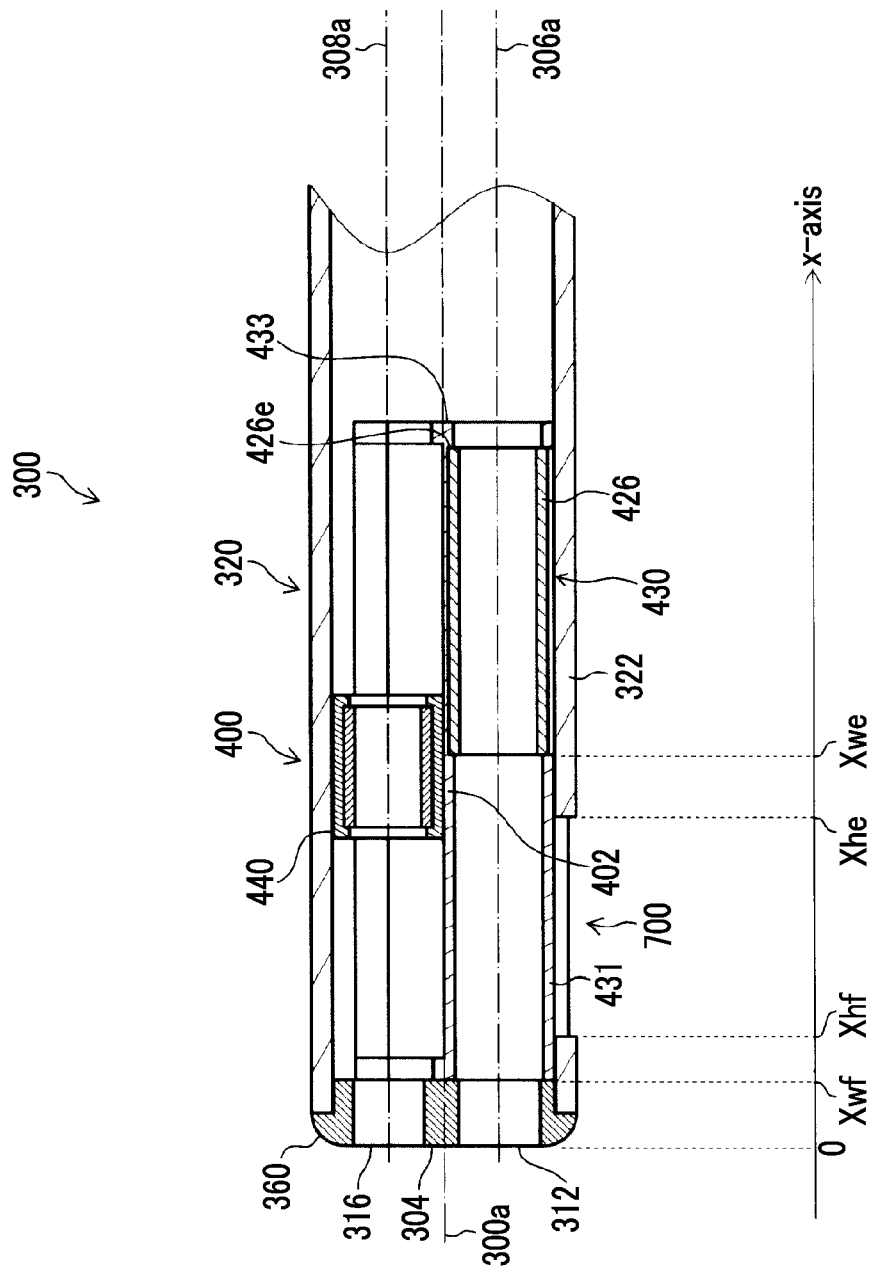
FIG. 23 is a partial cross-sectional view illustrating the vicinity of the distal end of the overtube in the endoscopic surgical device, to which the invention is applied, in an enlarged manner.

FIG. 23 is a partial cross-sectional view illustrating the vicinity of the distal end of the overtube 300 in an enlarged manner. As illustrated in this drawing, the left side surface 431 of the slider body 402 is arranged on the left side in the vicinity of the distal end of the overtube body 320 in a state where the slider body 402 has been arranged at the front end of the movable range thereof with respect to the overtube body 320.

The side hole 700 is provided with a position and a size included in a range that faces the left side surface 431 of the overtube body 320 in a state where the slider body 402 has been arranged at the front end of the movable range thereof.

Meanwhile, the shaft part 502 of the inner needle 500 illustrated in FIG. 19 and the like is formed with a diameter of a size such that the shaft part is brought into pressure contact with the pressure-contact member 426 of the slider body 402 and is connected (engaged with) to the slider body 402.

Figure 24:
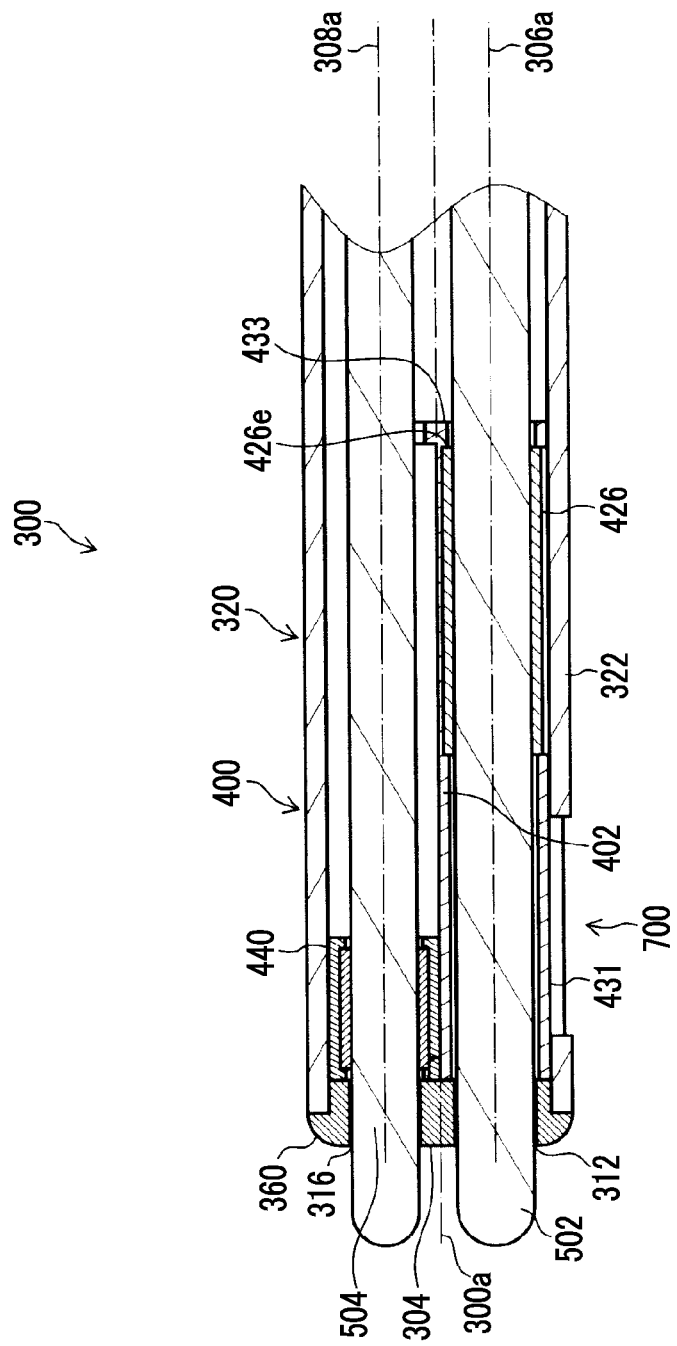
FIG. 24 is a partial cross-sectional view illustrating the vicinity of the distal end of the overtube in a state where an inner needle has been mounted on the overtube in the endoscopic surgical device, to which the invention is applied, in an enlarged manner.

Therefore, when the inner needle 500 is mounted on the overtube 300, the shaft part 502 of the inner needle 500 is coupled as an engagement part (frictional engagement part) that frictionally engages with the slider body 402. As illustrated in FIG. 24, the slider body 402 moves to the front end of the movable range thereof and is positioned at a position that faces the side hole 700, and the side hole 700 is closed by the left side surface 431 of the slider body 402.

Accordingly, when the inner needle 500 is mounted on the overtube 300 and the overtube 300 is inserted into a body wall, the side hole 700 is closed and tissue or blood in the body wall is prevented from entering the lumen 324 from the side hole 700.

Additionally, when the endoscope insertion part 102 and the treatment tool insertion part 202 are inserted through the endoscope insertion passage 306 and the treatment tool insertion passage 308 of the overtube 300 and treatment or the like is performed, supply of the pneumoperitoneum gas into a body cavity may be required. In that case, when the side hole 700 is closed by the slider 400, the side hole 700 can be opened by moving the slider 400 backward through the backward movement of the endoscope insertion part 102 or the treatment tool insertion part 202 in the axial direction. Then, the pneumoperitoneum gas can be favorably sent into a body cavity through the side hole 700 by sending the pneumoperitoneum gas into the overtube 300 from the pneumoperitoneum device 120 in that state.

(Other Configuration Examples of Inner Needle)

Next, another embodiment of the inner needle 500, which is suitable when the slider body 402 is moved to the front end of the movable range thereof by the inner needle 500 mounted on the overtube 300 as described above and the side hole 700 is closed, will be described.

Figure 25:
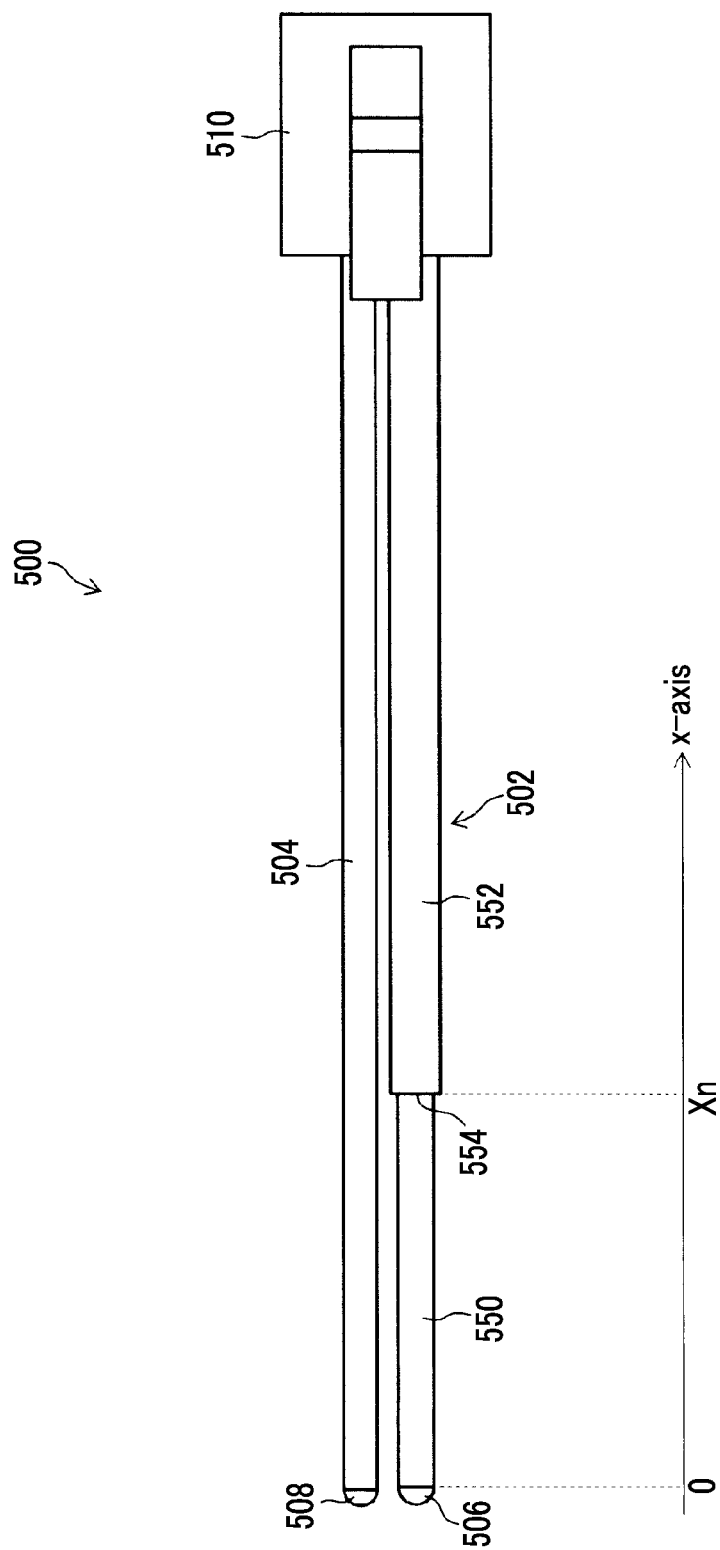
FIG. 25 is a plan view illustrating another embodiment of an inner needle adapted in order to close a side hole of the overtube in the endoscopic surgical device to which the invention is applied.

FIG. 25 is a plan view illustrating the other embodiment of the inner needle 500.

As illustrated in this drawing, the shaft part 502 of the inner needle 500 inserted through the endoscope insertion passage 306 of the overtube 300 has a stepped part 554 at a predetermined position, a smaller-diameter part 550 located closer to the distal end side than the stepped part 554, and a larger-diameter part 552 located closer to the base end side than the stepped part 554.

The larger-diameter part 550 has a thickness such that the larger-diameter part is not coupled to (engaged with) the slider 400 when being inserted through the endoscope insertion passage 306 of the overtube 300, and has a diameter of a size such that the larger-diameter part is insertable through at least the endoscope insertion passage 306 (the endoscope-coupled part 420 of the slider body 402).

The larger-diameter part 552 is thicker than the smaller-diameter part 550, and has a diameter of a size such that the larger-diameter part is not insertable through the endoscope-coupled part 420 of the slider body 402 when the shaft part 502 is inserted through the endoscope insertion passage 306 of the overtube 300. Accordingly, the larger-diameter part 552 interferes with the slider 400.

The stepped part 554 is formed at a boundary position between the smaller-diameter part 550 and the larger-diameter part 552, and has a coupling surface that is an annular surface orthogonal to the axial direction and couples an outer peripheral surface of the smaller-diameter part 550 and an outer peripheral surface of the larger-diameter part 552.

Figure 26:
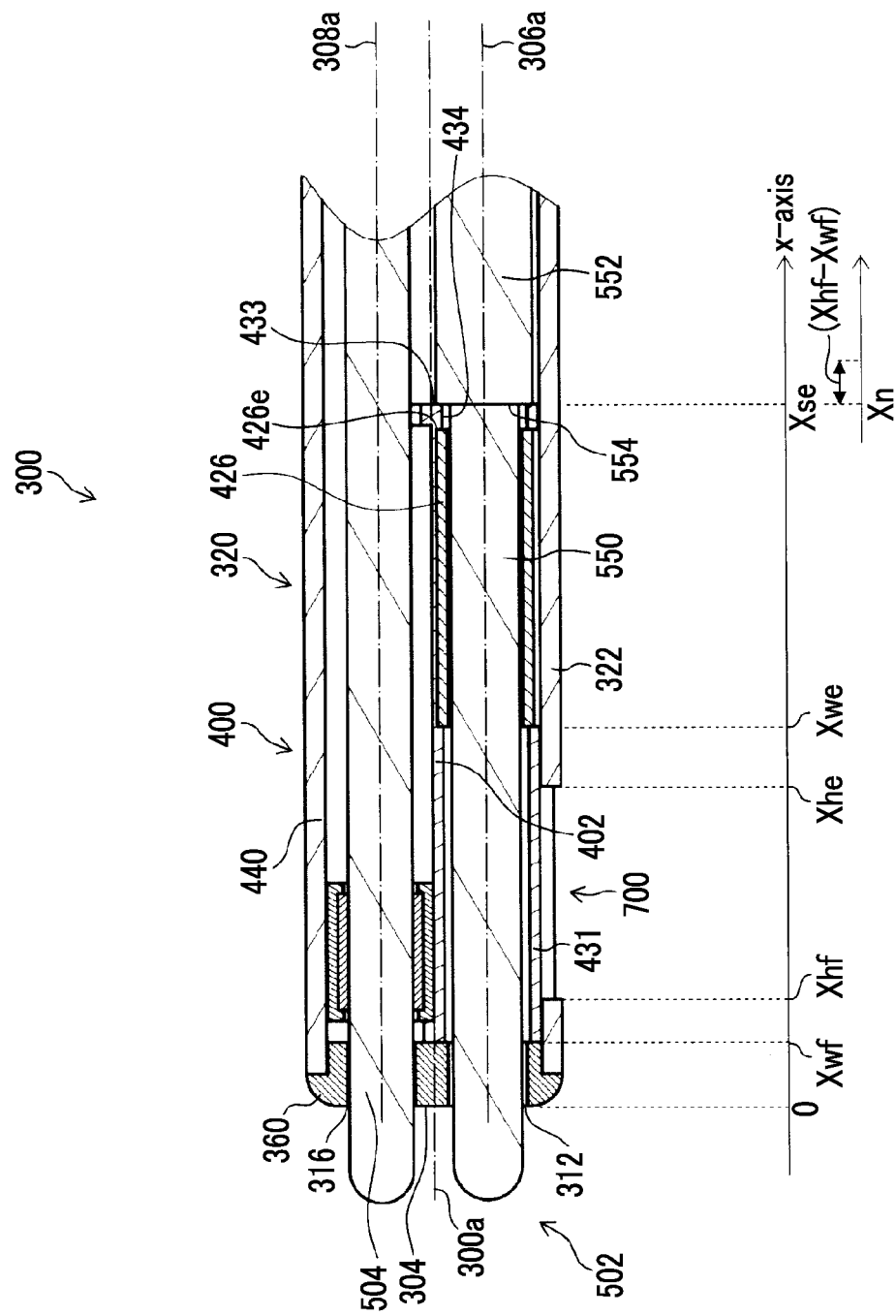
FIG. 26 is a sectional view illustrating the vicinity of the distal end of the overtube in a state where the inner needle of FIG. 25 has been mounted on the overtube, in an enlarged manner.

FIG. 26 is a sectional view illustrating a state in the vicinity of the distal end when the inner needle 500 of FIG. 25 has been mounted on the overtube 300.

As illustrated in this drawing, the larger-diameter part 552 of the shaft part 502 is thicker than the opening 434 (refer to FIG. 8) of the rear end surface 433, through which the endoscope insertion part 102 is inserted, in the slider body 402, and the stepped part 554 interferes with (abuts against) the rear end surface 433 (abutment part).

Accordingly, when the inner needle 500 is mounted on the overtube 300, the stepped part 554 of the shaft part 502 acts as an engagement part that engages with the slider 400, and the slider 400 is reliably pushed into the distal end side of the overtube 300.

Additionally, the stepped part 554 is formed at a position that substantially coincides with the rear end surface 433 of the slider body 402 arranged at the front end of the movable range thereof with respect to the overtube body 320, in a state where the inner needle 500 has been mounted on the overtube 300.

Accordingly, if the inner needle 500 is mounted on the overtube 300, the slider 400 is arranged at the front end of the movable range thereof, and the side hole 700 is closed.

In addition, the position of the slider body 402 with which the stepped part 554 of the shaft part 502 interferes can be arbitrary positions other than the rear end surface 433 of the slider body 402. For example, the larger-diameter part 552 has a diameter of a size such that the larger-diameter part is insertable through the opening 434 of the rear end surface 433 of the slider body 402, and has a diameter of a size such that the larger-diameter part is not insertable through the pressure-contact member 426. Accordingly, the stepped part 554 may interfere with a rear end 426e of the pressure-contact member 426.

(Arrangement Conditions of Slider Body and Side Hole)

Next, the arrangement conditions of the left side surface 431 of the slider body 402 and the side hole 700 in the direction of the reference axis 300a will be described.

As illustrated in FIG. 23, the position of the distal end surface 304 of the overtube 300 regarding positions in the direction of the reference axis 300a is defined as an origin, and an X-axis parallel to the reference axis 300a with the sense of the overtube 300 on the base end side as a positive sense is assumed.

The x-coordinate value of a rear end of the side hole 700 is defined as Xhf, and the x-coordinate value of a front end thereof is defined as Xhe.

Additionally, the x-coordinate value of a front end of the left side surface 431 of the slider body 402 arranged at the front end of the movable range thereof with respect to the overtube body 320 is defined as Xwf, and the x-coordinate value of a rear end thereof is defined as Xwe.

In this case, the side hole 700 and the left side surface 431 are designed so as to satisfy the following condition (16).

$$Xwf < Xhf < Xhe < Xwe \quad (16)$$

By satisfying this condition, in a state where the slider 400 has been arranged at the front end of the movable range, the side hole 700 is arranged within the range that faces the left side surface 431 of the slider body 402 and the side hole 700 is closed.

Additionally, if the arrangement conditions of the stepped part 554 of the inner needle 500 illustrated in FIG. 25 in the axial direction are described, the x-coordinate value of the stepped part 554 is defined as Xn, assuming the X-axis similar to FIG. 23 in a state where the inner needle 500 has been mounted on the overtube 300 as illustrated in FIG. 26.

The origin of the x-coordinate and the x-coordinate value Xn of the stepped part 554 in a state where the inner needle 500 has been mounted on the overtube 300 are illustrated in FIG. 25.

Meanwhile, the x-coordinate value (in the above form, the x-coordinate value of the rear end surface 433) of an interference position, which is a position (interference position) where the stepped part 554 interferes with the slider body 402 and is present in the slider body 402 arranged at the front end of the movable range with respect to the overtube body 320, is defined as Xse.

In this case, design is made so as to satisfy the following condition (17).

$$Xse \leq Xn \leq Xse + (Xhf - Xwf) \quad (17)$$

Although FIG. 26 illustrates a case where the stepped part 554 of the inner needle 500 is made to satisfy Xse=Xn, the condition (9) shows that it is possible to provide the position of the stepped part 554 at arbitrary positions between a position that coincides with Xse and a position moved back by a distance (Xhf−Xwf) from the coincidence position to the base end side.

The distance (Xhf−Xwf) represents the distance between the front end of the side hole 700 and the front end of the left side surface 431 in a state where the slider 400 has been arranged at the front end of the movable range thereof.

By satisfying this condition (9), the slider 400 is arranged between the position of the front end of the movable range and the position moved back by the distance (Xhf−Xwf) from the position of the front end, in a state where the inner needle 500 has been mounted on the overtube 300.

Therefore, the entire side hole 700 is closed by the left side surface 431 of the slider body 402.

As described above, in the inner needle 500 illustrated in FIG. 25, the shaft part 502 inserted through the endoscope insertion passage 306 is provided with the stepped part 554 that interferes with the slider 400. However, the invention is not limited to this, and the shaft part 504 inserted through the treatment tool insertion passage 308 of the overtube 300 may be provided with the stepped part 554 that interferes with the slider 400.

Additionally, in the above embodiment, the side hole 700 is formed at a position where the side hole is capable of being closed by the left side surface 431 of the slider body 402. However, the invention is not limited to this. A surface that approaches or contacts the inner peripheral surface of the overtube body 320 may be formed at arbitrary positions of the slider body 402, and the side hole may be provided at the position of the overtube body 320 that becomes closable by the surface. Accordingly, the side hole can be provided at the arbitrary positions of the overtube body 320.

However, the above slider 400 has a configuration that is suitable for reduction in the size of the slider 400 and reduction in the diameter of the overtube body 320 as described above, and providing the surface that closes the side hole at positions other than the left side surface 431 of the slider body 402 causes the enlargement of the slider body 402 in the forward-rearward direction or the radial direction. Therefore, reduction of the movable range of the slider body 402, an increase in the size of the overtube body 320 resulting from the enlargement of the slider body 402 in the radial direction, or the like is caused. Therefore, as in the above embodiment, it is desirable to form the side hole 700 at a position where the side hole is capable of being closed by the left side surface 431 of the slider body 402.

Additionally, in the above embodiment, the side hole 700 is closed by the slider body 402. However, the invention is not limited to this. It is also possible to adopt a form in which a shutter member, which is separate from the slider body 402 and is movable between an open position where the side hole 700 is open and a closed position where the side hole 700 is closed, is arranged inside the overtube body 320 (inside the lumen 324). In this case, the shutter member is moved in engagement with the inner needle 500 inserted into the overtube 300. A mechanism, which is located at the closed position where the shutter member closes the side hole 700 when the inner needle 500 has been mounted on the overtube 300, that is, when the head part body 512 of the inner needle 500 has been fixed to the overtube 300 by a fixing mechanism (locking lever 514) of the inner needle 500 and which is located at the open position where the shutter member opens the side hole 700 is open when the inner needle 500 has been detached from the overtube 300, may be provided.

Operation Method of Endoscopic Surgical Device

Next, an example of operation methods using the endoscopic surgical device 10 of the present embodiment will be described.

FIGS. 27A to 32B are explanatory views illustrating a situation in which the endoscopic surgical device 10 of the present embodiment is operated.

Figure 27A:
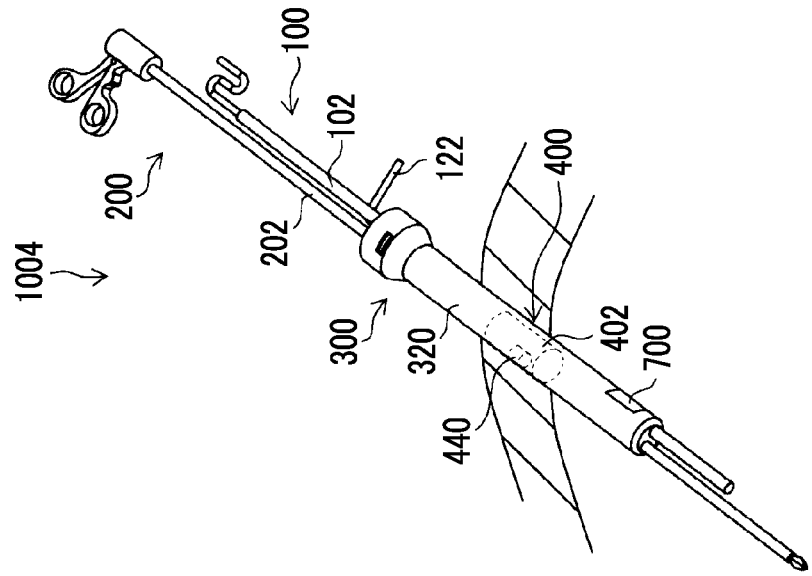
FIGS. 27A to 27C are views illustrating a situation in which the overtube is inserted into a body wall.
Figure 27B:
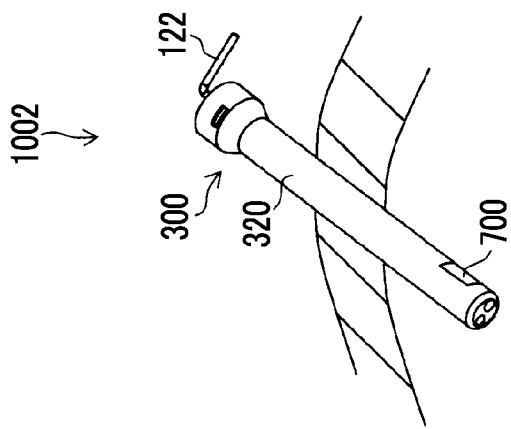
Figure 27C:
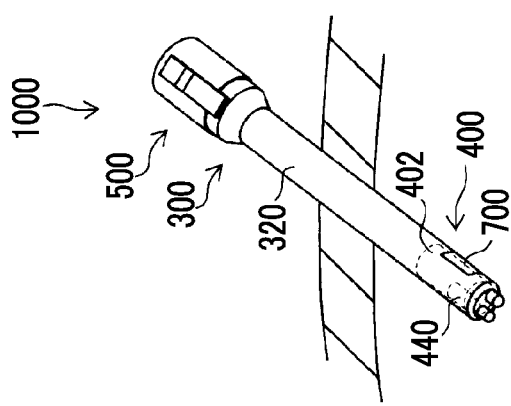

FIGS. 27A to 27C are views illustrating a situation in which the overtube 300 is inserted into a body wall.

FIGS. 28A to 29B are views illustrating a situation in which the treatment tool insertion part 202 is pushed into an affected part side within a body cavity from the hand side.

FIGS. 30A to 31B are views illustrating a situation in which the treatment tool insertion part 202 is pulled to the hand side from the affected part side within the body cavity.

Figure 32A:
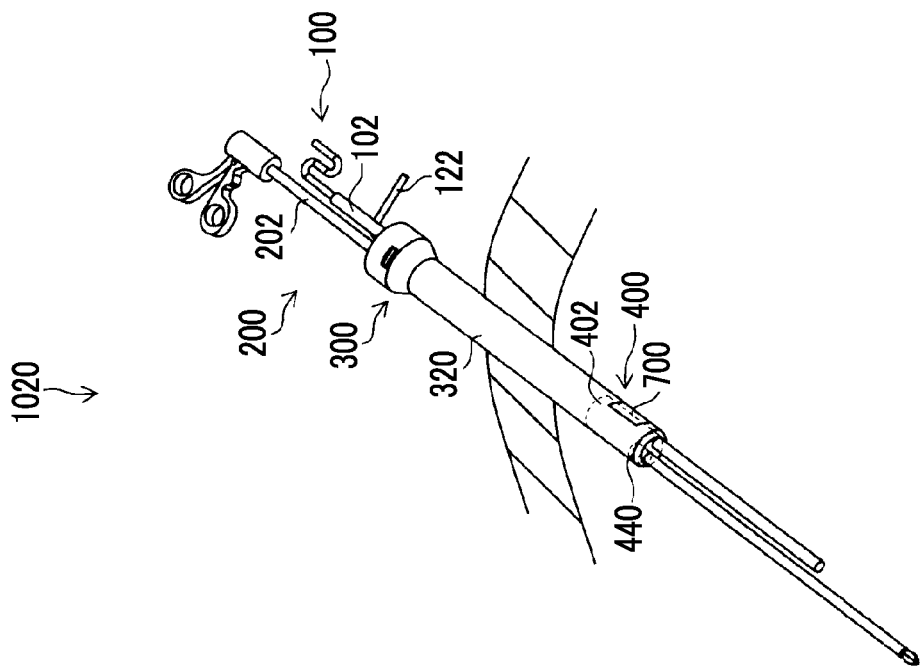
FIGS. 32A and 32B are views illustrating a situation in which pneumoperitoneum gas is injected into a body cavity in a state where an endoscope insertion part and a treatment tool insertion part are inserted through the overtube.
Figure 32B:
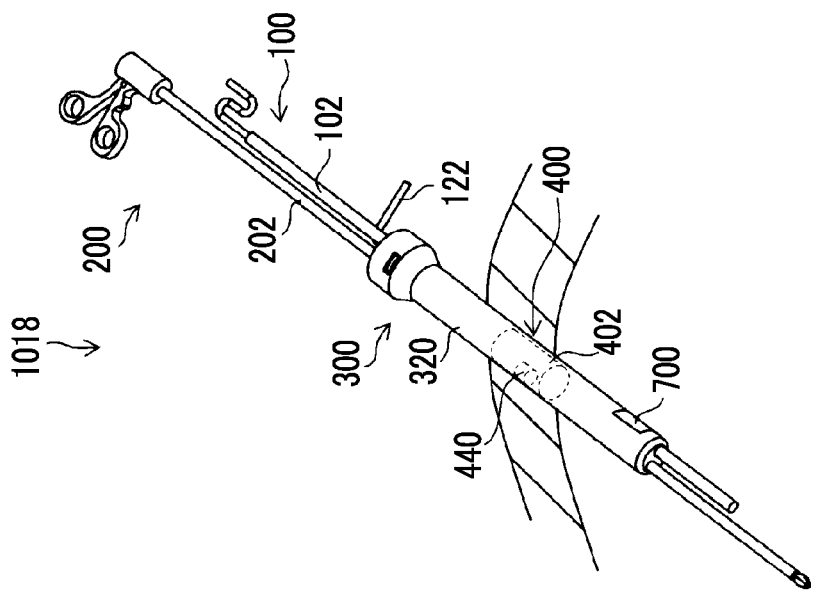

FIGS. 32A and 32B are views illustrating a situation in which the pneumoperitoneum gas is injected into the body cavity in a state where the endoscope insertion part 102 and the treatment tool insertion part 202 are inserted through the overtube 300.

First, as a preparation process for starting the operation of the endoscopic surgical device 10, the overtube 300 is inserted into a skin incision part (incised wound) formed in a body wall in a state where the inner needle 500 has been mounted on the overtube 300, and the overtube 300 is inserted into the body cavity like a state designated by reference sign 1000 of FIG. 27A. In this case, since the side hole 700 formed in the vicinity of the distal end of the overtube body 320 is closed by the slider 400, tissue or blood in a body wall is prevented from entering the overtube 300 from the side hole 700. Additionally, the side hole 700 is arranged within a body cavity.

Next, the inner needle 500 is extracted from the endoscope insertion passage 306 and the treatment tool insertion passage 308 (the inner needle 500 is removed from the overtube 300), and one end part of the air supply tube 122 is connected to the air supply connector 318 of the overtube 300 like a state designated by reference sign 1002 of FIG. 27B. The other end part is connected to the pneumoperitoneum device 120. Then, pneumoperitoneum gas is delivered from the pneumoperitoneum device 120, and the pneumoperitoneum gas is injected into the body cavity through the air supply tube 122 and the overtube 300. In this case, since the position within the overtube body 320 of the slider 400 is indefinite, whether the side hole 700 is open or closed depends on the circumstances. However, since the overtube 300 is in a state where the endoscope insertion part 102 and the treatment tool insertion part 202 are not inserted into the endoscope insertion passage 306 and the treatment tool insertion passage 308, the pneumoperitoneum gas sent into the overtube 300 from the pneumoperitoneum device 120 is excellently sent into a body cavity at least from the endoscope delivery opening 312 and the treatment tool delivery opening 316 at the distal end of the overtube 300. If the side hole 700 is in an open state, the pneumoperitoneum gas is also sent into a body cavity from the side hole 700.

If the injection of the pneumoperitoneum gas into a body cavity is completed, next, the endoscope insertion part 102 is inserted into the endoscope insertion passage 306 from the endoscope insertion opening 310 of the overtube 300, and the distal end of the endoscope insertion part 102 is led out from the endoscope delivery opening 312.

In this case, the endoscope insertion part 102 has the endoscope-coupled part 420 of the slider 400 inserted therethrough, and is coupled to the slider body 402 as described above. Accordingly, the endoscope insertion part 102 and the slider 400 are brought into a state where they move integrally.

Subsequently, the treatment tool insertion part 202 is inserted into the treatment tool insertion passage 308 from the treatment tool insertion opening 314 of the overtube 300, and the distal end (treatment part 206) of the treatment tool insertion part 202 is led out from the treatment tool delivery opening 316.

In this case, the treatment tool insertion part 202 has the sleeve 440 of the treatment tool-coupled part 422 of the slider 400 inserted therethrough, and is coupled to the sleeve 440 as described above. Accordingly, the treatment tool insertion part 202 and the sleeve 440 are brought into a state where they move integrally.

If the preparation step is performed in this way, a state where the operation of the endoscopic surgical device 10 is operable is brought about like a state designated by reference sign 1004 of FIG. 27C.

In addition, the distal end position of the endoscope insertion part 102 is arranged behind at least the distal end position of the treatment tool insertion part 202 so that the situation of the treatment part 206 at the distal end of the treatment tool insertion part 202 can be observed by the endoscope 100. Additionally, the procedure of inserting the endoscope insertion part 102 and the treatment tool insertion part 202 into the overtube 300 is not limited to the above-described order, and the endoscope insertion part 102 may be inserted after the treatment tool insertion part 202 is inserted.

Next, a case where the treatment tool insertion part 202 is pushed into the affected part side within the body cavity from the hand side (a case where the treatment tool insertion part moves forward) will be described with reference to FIGS. 28A to 29B.

First, when the treatment tool insertion part 202 has been minutely displaced in the axial direction like a state designated by reference sign 1008 of FIG. 28B from a state designated by reference sign 1006 of FIG. 28A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

In contrast, when the treatment tool insertion part 202 has been largely displaced in the axial direction like a state designated by reference sign 1006 of FIG. 29B from a state designated by reference sign 1006 of FIG. 29A that is the same state as reference sign 1010 of FIG. 28A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

Additionally, the same applies to a case where the treatment tool insertion part 202 is pulled to the hand side from the affected part side within the body cavity (when the treatment tool insertion part moves backward).

That is, when the treatment tool insertion part 202 has been minutely displaced in the axial direction like a state designated by reference sign 1014 of FIG. 30B from a state designated by reference sign 1012 of FIG. 30A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

In contrast, when the treatment tool insertion part 202 has been largely displaced in the axial direction like a state designated by reference sign 1012 of FIG. 31B from a state designated by reference sign 1012 of FIG. 31A that is the same state as reference sign 1016 of FIG. 30A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

Next, during treatment or the like, a case where the pneumoperitoneum gas is not injected into a body cavity in a state where the endoscope insertion part 102 and the treatment tool insertion part 202 are respectively inserted through the endoscope insertion passage 306 and the treatment tool insertion passage 308 of the overtube 300 will be described with reference to FIGS. 32A and 32B.

As in a state indicated by reference sign 1018 of FIG. 32A, the side hole 700 is open when the slider 400 is not arranged in the vicinity of the distal end of the overtube body 320. In this case, the state is maintained and the pneumoperitoneum gas is sent into the overtube 300 via the air supply tube 122 from the pneumoperitoneum device 120. Accordingly, the pneumoperitoneum gas sent into the overtube 300 is mainly sent into a body cavity through the side hole 700.

Meanwhile, as in a state indicated by reference sign 1020 of FIG. 32B, the side hole 700 is closed when the slider 400 is arranged in the vicinity of the distal end of the overtube body 320. In this case, the treatment tool insertion part 202 or the endoscope insertion part 102 is moved back and the slider 400 is moved back to the base end side. Accordingly, the side hole 700 is made to open as in a state indicated by reference sign 1018 of FIG. 32A. Then, as described above, the state is maintained and the pneumoperitoneum gas is sent into the overtube 300 via the air supply tube 122 from the pneumoperitoneum device 120. Accordingly, the pneu-moperitoneum gas sent into the overtube 300 is mainly sent into a body cavity through the side hole 700.

In this way, according to the endoscopic surgical device 10 of the present embodiment, the side hole 700 (side surface opening) is configured to be openable and closable by the forward and backward movement of the slider 400. Thus, the pneumoperitoneum gas can be efficiently sent into a body cavity with a compact structure without causing an increase in cost and an increase in size, and it is possible to effectively prevent tissue or blood in a body wall from entering the overtube body 320 through the side hole 700.

Although the endoscopic surgical device and the overtube related to the invention have been described above in detail, the invention is not limited to the above embodiments, and various improvements and modifications may be made without departing from the scope of the invention.

EXPLANATION OF REFERENCES

10: endoscopic surgical device
100: endoscope
102: endoscope insertion part
104: operating part
108: processor device
110: light source device
112: monitor
120: pneumoperitoneum device
122: air supply tube
200: treatment tool
202: treatment tool insertion part
204: operating part
206: treatment part
300: overtube
302: base end surface
304: distal end surface
306: endoscope insertion passage
306a: endoscope insertion axis
308: treatment tool insertion passage
308a: treatment tool insertion axis
310: endoscope insertion opening
312: endoscope delivery opening
314: treatment tool insertion opening
316: treatment tool delivery opening
318: air supply connector
320: overtube body
322: outer wall
324: lumen
340: base end cap
342, 344, 350: through-hole
346, 348: valve member
360: distal end cap
362, 364: through-hole
370, 372: guide groove
374, 376: guide plate
400: slider
402: slider body
408, 410: protruding strip
420: endoscope-coupled part
422: treatment tool-coupled part
424: through-hole
426: pressure-contact member
428: pressure-contact member attachment part
431: left side surface
440: sleeve
444: sleeve body
446: pressure-contact member
448, 450: through-hole 460: guide part
500: inner needle
502, 504: shaft part
506, 508: distal end part
510: head part
512: head part body
514: locking lever
520: axis
532: locking claw
534: locking hole
550: smaller-diameter part
552: larger-diameter part
554: stepped part
700: side hole

What is claimed is:

1. An endoscopic surgical device comprising:
an endoscope that is configured to observe an inside of a body cavity;
a treatment tool that is configured to inspect or treat an affected part within the body cavity; and
an overtube that is configured to guide the endoscope and the treatment tool into the body cavity,
wherein the overtube includes
an overtube body that is configured to pass through a body wall and is configured to be inserted into the body cavity,
an endoscope insertion passage that is provided inside the overtube body and allows the endoscope to be inserted therethrough so as to be movable forward and backward,
a treatment tool insertion passage that is provided inside the overtube body and allows the treatment tool to be inserted therethrough so as to be movable forward and backward,
a slider which is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, wherein the endoscope-coupled part comprises a through-hole, and the treatment tool-coupled part comprises a sleeve that is coupled to the treatment tool, and
a side surface opening that is formed to pass through a side wall of the overtube body, in communication with a passage in the overtube body, and is configured to send a fluid into the body cavity, and
wherein the side surface opening is configured to be openable and closable by the forward and backward movement of the slider.

2. The endoscopic surgical device according to claim 1, further comprising:
an inner needle that includes a first elongated shaft part inserted through the endoscope insertion passage and a second elongated shaft part inserted through the treatment tool insertion passage, and that is assembled into the overtube body in a state where respective distal end parts of the first shaft part and the second shaft part are made to protrude from the overtube body when being inserted into the body cavity,
wherein the slider is positioned at a position that faces the side surface opening in a state where the inner needle has been assembled into the overtube body, and the side surface opening is closed by one wall surface of the slider.

3. The endoscopic surgical device according to claim 2,
wherein the first shaft part or the second shaft part is provided with an engagement part that engages with the slider, and
wherein the slider is positioned at a position that faces the side surface opening by the engagement part of the first shaft part or the second shaft part being engaged therewith, in a state where the inner needle has been assembled into the overtube body,
wherein the engagement part of the first shaft part or the second shaft part is a wall surface of the first shaft part or the second shaft part.

4. The endoscopic surgical device according to claim 3,
wherein the inner needle includes a head part that links a base end of the first shaft part and a base end of the second shaft part, and a locking lever that is provided at the head part and detachably fixes the head part to the overtube, and
wherein the slider is arranged at a position that faces the side surface opening when the head part has been fixed to the overtube by the locking lever.

5. The endoscopic surgical device according to claim 3,
wherein the first shaft part or the second shaft part includes a smaller-diameter part that is arranged on a distal end side of the first shaft part or the second shaft part, and a larger-diameter part that is connected to a base end side of the smaller-diameter part,
wherein the engagement part is constituted by a stepped part formed at a boundary position between the smaller-diameter part and the larger-diameter part, and
wherein the slider includes a hole that is larger than the external diameter of the smaller-diameter part and is smaller than the external diameter of the larger-diameter part, and an abutment part that is a peripheral part of the hole and against which the stepped part abuts.

6. The endoscopic surgical device according to claim 3,
wherein the engagement part frictionally engages with the slider.

7. The endoscopic surgical device according to claim 1,
wherein the side surface opening is provided on a distal end side of the overtube body, and is closed by one wall surface of the slider when the slider has moved to a foremost position of a movable range thereof.

8. The endoscopic surgical device according to claim 1,
wherein the slider includes a slider body that is coupled to the endoscope and moves forward and backward integrally with the endoscope, and the sleeve that is coupled to the treatment tool and moves forward and backward integrally with the treatment tool, and
wherein a range where the sleeve is movable forward and backward with respect to the slider body is limited,
wherein the slider body comprises the endoscope-coupled part.

9. The endoscopic surgical device according to claim 1,
wherein a following formula is satisfied when a fixing force for fixing the endoscope-coupled part to the endoscope is defined as F1 and a fixing force for the treatment tool-coupled part to the treatment tool is defined as F2

$F1 > F2$

10. The endoscopic surgical device according to claim 1, further comprising:
a first valve member that is provided in the endoscope insertion passage and secures airtightness within the body cavity; and a second valve member that is provided in the treatment tool insertion passage and secures airtightness within the body cavity, wherein following formulas are satisfied when a fixing force for fixing the endoscope-coupled part to the endoscope is defined as F1, a fixing force for fixing the treatment tool-coupled part to the treatment tool is defined as F2, and a frictional force that the endoscope receives from the first valve member when the endoscope moves forward and backward is defined as F3

$F1>F3$ $F2>F3$

11. An endoscopic surgical device comprising:

an inner needle; and an overtube that is configured to guide the inner needle into the body cavity, wherein the inner needle that includes a first elongated shaft part and a second elongated shaft part, and that is assembled into the overtube body in a state where respective distal end parts of the first shaft part and the second shaft part are made to protrude from the overtube body when being inserted into the body cavity, and wherein the overtube includes an overtube body that is configured to pass through a body wall and is configured to be inserted into the body cavity, a first insertion passage that is provided inside the overtube body and allows the first shaft part to be inserted therethrough so as to be movable forward and backward, a second insertion passage that is provided inside the overtube body and allows the second shaft part to be inserted therethrough so as to be movable forward and backward, a slider which is configured to be movable forward and backward inside the overtube body, couplable to the first shaft part inserted through the first insertion passage and the second shaft part inserted through the second insertion passage, a side surface opening that is formed to pass through a side wall of the overtube body, in communication with a passage in the overtube body, and is configured to send a fluid into the body cavity, and a shutter member that is arranged inside the overtube body, is movable in engagement with the inner needle, and is movable between an open position where the side surface opening is open and a closed position where the side surface opening is closed.

12. The endoscopic surgical device according to claim 11, wherein the inner needle includes a head part that links a base end of the first shaft part and a base end of the second shaft part, and a locking lever that is provided at the head part and detachably fixes the head part to the overtube, and wherein the shutter member is located at the closed position when the head part has been fixed to the overtube by the locking lever.

13. An overtube comprising:

an overtube body that is configured to pass through a body wall and is configured to be inserted into a body cavity;

an endoscope insertion passage that is provided inside the overtube body and allows an endoscope for observing the inside of the body cavity to be inserted therethrough so as to be movable forward and backward;

a treatment tool insertion passage that is provided inside the overtube body and allows a treatment tool for inspecting or treating an affected part within the body cavity to be inserted therethrough so as to be movable forward and backward;

a slider which is configured to be movable forward and backward inside the overtube body, has an endoscope-coupled part to be coupled to the endoscope inserted through the endoscope insertion passage and a treatment tool-coupled part to be coupled to the treatment tool inserted through the treatment tool insertion passage, wherein the endoscope-coupled part comprises a through-hole, and the treatment tool-coupled part comprises a sleeve that is coupled to the treatment tool; and a side surface opening that is formed to pass through a side wall of the overtube body, in communication with a passage in the overtube body, and is configured to send a fluid into the body cavity, wherein the side surface opening is configured to be openable and closable by the forward and backward movement of the slider.

14. The overtube according to claim 13, further comprising:

an inner needle that includes a first elongated shaft part inserted through the endoscope insertion passage and a second elongated shaft part inserted through the treatment tool insertion passage, and that is assembled into the overtube body in a state where respective distal end parts of the first shaft part and the second shaft part are made to protrude from the overtube body when being inserted into the body cavity, wherein the slider is positioned at a position that faces the side surface opening in a state where the inner needle has been assembled into the overtube body, and the side surface opening is closed by one wall surface of the slider.

15. The overtube according to claim 14, wherein the first shaft part or the second shaft part is provided with an engagement part that engages with the slider, and wherein the slider is positioned at a position that faces the side surface opening by the engagement part of the first shaft part or the second shaft part being engaged therewith, in a state where the inner needle has been assembled into the overtube body, wherein the engagement part of the first shaft part or the second shaft part is a wall surface of the first shaft part or the second shaft part.

16. The overtube according to claim 15, wherein the inner needle includes a head part that links a base end of the first shaft part and a base end of the second shaft part, and a locking lever that is provided at the head part and detachably fixes the head part to the overtube, and wherein the slider is arranged at a position that faces the side surface opening when the head part has been fixed to the overtube by the locking lever.

17. The overtube according to claim 15, wherein the first shaft part or the second shaft part includes a smaller-diameter part that is arranged on a distal end side of the first shaft part or the second shaft part, and a larger-diameter part that is connected to a base end side of the smaller-diameter part, wherein the engagement part is constituted by a stepped part formed at a boundary position between the smaller-diameter part and the larger-diameter part, and wherein the slider includes a hole that is larger than the external diameter of the smaller-diameter part and is smaller than the external diameter of the larger-diameter part, and an abutment part that is a peripheral part of the hole and against which the stepped part abuts.

18. The overtube according to claim 15,
wherein the engagement part frictionally engages with the slider.

19. The overtube according to claim 13,
wherein the side surface opening is provided on a distal end side of the overtube body, and is closed by one wall surface of the slider when the slider has moved to a foremost position of a movable range thereof.

* * * * *